(12) United States Patent
Zwirkoski et al.

(10) Patent No.: US 9,168,188 B2
(45) Date of Patent: Oct. 27, 2015

(54) CAST REMOVAL SYSTEM

(75) Inventors: Paul A. Zwirkoski, Brighton, MI (US);
Joseph T. Adams, Howell, MI (US);
Nick A. Deeter, Warsaw, IN (US); Gary D. Barnett, Wabash, IN (US); Bob von Seggern, Columbia City, IN (US);
Michael C. Jones, North Webster, IN (US)

(73) Assignee: OrthoPediatrics Corporation, Warsaw, IN (US)

( * ) Notice: Subject to any disclaimer, the term of this patent is extended or adjusted under 35 U.S.C. 154(b) by 1102 days.

(21) Appl. No.: 12/742,874

(22) PCT Filed: Nov. 13, 2008

(86) PCT No.: PCT/US2008/083453
§ 371 (c)(1),
(2), (4) Date: Aug. 10, 2011

(87) PCT Pub. No.: WO2009/064925
PCT Pub. Date: May 22, 2009

(65) Prior Publication Data
US 2012/0005904 A1    Jan. 12, 2012

Related U.S. Application Data

(60) Provisional application No. 61/002,842, filed on Nov. 13, 2007, provisional application No. 61/010,551, filed on Jan. 9, 2008, provisional application No. 61/072,996, filed on Apr. 4, 2008, provisional application No. 61/104,061, filed on Oct. 9, 2008.

(51) Int. Cl.
*A61F 15/02*    (2006.01)
*B26D 7/22*    (2006.01)
(Continued)

(52) U.S. Cl.
CPC ............... *A61F 15/02* (2013.01); *B23D 61/02* (2013.01); *B23D 61/12* (2013.01); *B23D 61/18* (2013.01); *B26B 25/00* (2013.01)

(58) Field of Classification Search
CPC ......... A61F 15/02; B27B 5/38; B27B 19/006; B23D 59/006; B23D 61/21; B23D 61/02; B23D 61/18; B23D 59/00; B23D 59/02; B26B 25/00
USPC ........ 30/370, 166.3, 390, 373, 388, 516, 396, 30/398, 41.5, 43.7, 43.9, 394, 272.1, 30/277.4, 123.3, 389, 276, 347; 83/602; 125/11.22
See application file for complete search history.

(56) References Cited

U.S. PATENT DOCUMENTS 576,610 A    2/1897    Pohlsen
590,163 A    9/1897    Pearson
(Continued)

FOREIGN PATENT DOCUMENTS

CH    116910    10/1926
DE    437169    11/1926
(Continued)

OTHER PUBLICATIONS

Authorized Officer Blaine R. Copenheaver, WIPO, Serial No. PCT/US2008/083453, Search Report & Written Opinion, Mar. 13, 2009, 12 pages.
(Continued)

*Primary Examiner* — Ghassem Alie
(74) *Attorney, Agent, or Firm* — Douglas G. Gallagher; John V. Danilick; Bingham Greenebaum Doll LLP

(57) ABSTRACT

Apparatus and methods for cutting a material, especially with low material speed and high cutting torque. In some embodiments, the apparatus is a hand-held device for quietly cutting through an orthopedic cast with little or no generation of debris. In yet other embodiments, there is a method for automatically advancing material past a shearing surface, such that the shearing action occurs at about the same velocity as the advancement. In yet other embodiments, there is a device for cutting material between a foot and a sharp edge, with the bottom of the foot being under the sharp edge to protect the skin of the patient.

24 Claims, 76 Drawing Sheets

(51) Int. Cl.
    *B23D 61/02*    (2006.01)
    *B23D 61/12*    (2006.01)
    *B23D 61/18*    (2006.01)
    *B26B 25/00*    (2006.01)

(56) References Cited

U.S. PATENT DOCUMENTS

| | | |
|---|---|---|
| 1,269,373 A | 6/1918 | Brinck |
| 1,530,023 A | 3/1925 | Walton |
| 1,641,505 A | 9/1927 | Sayre |
| 1,649,957 A | 11/1927 | Holtzman |
| 1,744,597 A | 1/1930 | Vasconcellos |
| 1,763,730 A | 6/1930 | Von Lackum |
| 1,858,459 A | 5/1932 | Ramey |
| 1,876,337 A * | 9/1932 | Mead ............... 30/124 |
| 2,015,535 A | 9/1935 | Sacrey |
| 2,042,097 A | 5/1936 | Havanas |
| 2,070,358 A | 2/1937 | Hengstenberg |
| 2,084,488 A | 6/1937 | Heller |
| 2,217,923 A | 10/1940 | Silverman |
| 2,232,733 A | 2/1941 | Scarboro |
| 2,330,952 A | 10/1943 | Gottfried |
| 2,344,262 A | 3/1944 | Odierna |
| 2,366,017 A | 12/1944 | Fortune |
| 2,369,925 A | 2/1945 | Smith |
| 2,617,186 A | 4/1947 | Pickles |
| 2,427,580 A | 9/1947 | Stryker |
| 2,502,656 A | 4/1950 | Koett |
| 2,522,006 A * | 9/1950 | Wilcox ............... 30/124 |
| 2,557,364 A | 6/1951 | Tillson |
| 2,570,195 A | 10/1951 | Bird |
| 2,571,527 A | 10/1951 | Boyer |
| 2,642,658 A | 6/1953 | Johnson |
| 2,679,199 A | 5/1954 | Strehlow |
| 2,702,550 A | 2/1955 | Rowe |
| 2,728,985 A | 1/1956 | Quackenbush |
| 2,795,247 A | 6/1957 | Topolinski |
| 2,898,957 A | 1/1958 | Demarkis |
| 2,868,306 A | 1/1959 | Monroe |
| 2,901,051 A | 8/1959 | Thibodeau |
| 3,042,118 A | 7/1962 | Norris |
| 3,044,171 A | 7/1962 | Emil |
| 3,091,851 A | 6/1963 | Cummins |
| 3,103,069 A | 9/1963 | Gary |
| 3,137,192 A | 6/1964 | McNeill |
| 3,199,194 A | 8/1965 | Shaheen |
| 3,269,010 A | 8/1966 | Bettcher |
| 3,277,760 A | 10/1966 | Keene |
| 3,353,266 A | 11/1967 | Goolsby |
| 3,364,710 A | 1/1968 | Georges |
| 3,365,798 A | 1/1968 | Cunningham |
| 3,425,467 A | 2/1969 | Willis |
| 3,456,696 A | 7/1969 | Gregory |
| 3,468,350 A | 9/1969 | Logan |
| 3,468,351 A | 9/1969 | Ehlen |
| 3,469,313 A | 9/1969 | Martin |
| 3,481,036 A | 12/1969 | Slaughter |
| 3,675,526 A | 7/1972 | Bush |
| 3,710,445 A | 1/1973 | Roth |
| 3,852,881 A | 12/1974 | Treace |
| 3,857,177 A | 12/1974 | Karubian |
| 3,869,795 A | 3/1975 | Treace |
| 3,905,374 A | 9/1975 | Winter |
| 3,906,629 A | 9/1975 | Fuchs, Jr. |
| 3,952,412 A | 4/1976 | Rhodes |
| 4,036,236 A | 7/1977 | Rhodes, Jr. |
| 4,069,824 A | 1/1978 | Weinstock |
| 4,081,906 A | 4/1978 | Sigler |
| 4,106,181 A | 8/1978 | Mattchen |
| 4,150,598 A | 4/1979 | Berends |
| 4,213,364 A | 7/1980 | Sahlin |
| 4,221,051 A | 9/1980 | Glass |
| 4,224,855 A | 9/1980 | Des Roches |
| 4,229,963 A | 10/1980 | Savinov |
| 4,233,738 A | 11/1980 | Dedrick |
| 4,241,505 A | 12/1980 | Bodycomb, Jr. |
| 4,249,313 A | 2/1981 | Bates |
| 4,252,121 A | 2/1981 | Arnegger |
| 4,252,239 A | 2/1981 | Snyder |
| 4,257,294 A | 3/1981 | Stoveken |
| 4,257,297 A | 3/1981 | Nidbella |
| 4,275,500 A | 6/1981 | Speer, Jr. |
| 4,281,457 A | 8/1981 | Walton, II |
| 4,290,424 A | 9/1981 | Wahl |
| D262,823 S | 1/1982 | House, II |
| 4,319,433 A | 3/1982 | Nolen |
| D263,744 S | 4/1982 | Straub |
| 4,353,165 A | 10/1982 | Albery |
| 4,372,047 A | 2/1983 | Marttinen |
| 4,381,605 A | 5/1983 | Holm |
| 4,386,609 A | 6/1983 | Mongeon |
| 4,406,064 A | 9/1983 | Goss |
| 4,409,973 A | 10/1983 | Neufeld |
| 4,411,067 A | 10/1983 | Kirk |
| 4,412,381 A | 11/1983 | Kirk |
| 4,421,111 A | 12/1983 | Rothman |
| 4,422,239 A | 12/1983 | Maier |
| 4,450,627 A | 5/1984 | Morimoto |
| 4,511,334 A | 4/1985 | Grafelmann |
| 4,513,742 A | 4/1985 | Arnegger |
| 4,543,718 A | 10/1985 | Duescher |
| 4,545,121 A | 10/1985 | Armbruster |
| 4,574,480 A | 3/1986 | Dunn |
| 4,584,999 A | 4/1986 | Arnegger |
| 4,602,435 A | 7/1986 | Nishioka |
| 4,604,804 A | 8/1986 | Sparks |
| 4,609,578 A | 9/1986 | Reed |
| 4,611,585 A | 9/1986 | Steidle |
| 4,619,170 A | 10/1986 | Maier |
| 4,620,367 A | 11/1986 | Tubesing |
| 4,625,405 A * | 12/1986 | Hudnutt et al. ............ 30/370 |
| 4,628,604 A | 12/1986 | Fuchs |
| 4,637,391 A | 1/1987 | Schlein |
| 4,644,835 A | 2/1987 | Bleicher |
| 4,646,607 A | 3/1987 | Johansson |
| 4,658,506 A | 4/1987 | Nilsson |
| 4,677,750 A | 7/1987 | Maier |
| 4,687,192 A | 8/1987 | Hunt |
| 4,705,840 A | 11/1987 | Buckanin |
| 4,730,396 A | 3/1988 | Nishioka |
| 4,736,742 A | 4/1988 | Alexson |
| 4,744,148 A | 5/1988 | Brown |
| 4,774,937 A | 10/1988 | Scholz |
| 4,793,065 A | 12/1988 | Johansson |
| 4,809,438 A | 3/1989 | Nagashima |
| 4,819,334 A | 4/1989 | Mongeon |
| 4,821,415 A | 4/1989 | Kress |
| 4,827,617 A | 5/1989 | Shepherd |
| 4,870,758 A | 10/1989 | Fushiya |
| 4,873,766 A | 10/1989 | Johnston |
| 4,895,336 A | 1/1990 | Lieberman |
| 4,922,612 A | 5/1990 | Greenwood |
| 4,939,843 A | 7/1990 | Rogers |
| 4,959,907 A | 10/1990 | Buratty |
| 4,972,588 A | 11/1990 | Briach, Sr. |
| 4,976,034 A | 12/1990 | Whitman |
| 4,979,307 A | 12/1990 | Ste. Marie |
| 4,999,916 A | 3/1991 | Sistare |
| 5,005,295 A | 4/1991 | Fushiya |
| 5,009,011 A | 4/1991 | Johansson |
| 5,010,651 A | 4/1991 | Techter |
| 5,012,582 A | 5/1991 | Bristol et al. |
| 5,020,226 A | 6/1991 | Chabbert |
| 5,023,999 A | 6/1991 | Looper |
| 5,036,740 A | 8/1991 | Tsai |
| 5,038,474 A | 8/1991 | Larsson et al. |
| 5,074,044 A | 12/1991 | Duncan |
| 5,090,839 A | 2/1992 | Naslund |
| 5,115,567 A | 5/1992 | Yang |
| 5,135,332 A | 8/1992 | Hellwig |
| 5,136,469 A | 8/1992 | Carusillo |
| 5,136,910 A | 8/1992 | Kuhn |
| D329,092 S | 9/1992 | Carusillo |
| 5,146,682 A | 9/1992 | Blochle |

(56) References Cited

U.S. PATENT DOCUMENTS

| | | |
|---|---|---|
| 5,163,674 A | 11/1992 | Parks |
| 5,205,422 A | 4/1993 | Morris |
| 5,207,697 A | 5/1993 | Carusillo |
| D337,160 S | 7/1993 | Evans |
| 5,235,261 A | 8/1993 | Philipp |
| 5,239,756 A | 8/1993 | Matzo |
| 5,259,428 A | 11/1993 | Matthews |
| 5,265,340 A | 11/1993 | Nitz |
| 5,271,155 A | 12/1993 | Fuchs |
| D343,247 S | 1/1994 | Walen |
| 5,287,786 A | 2/1994 | Fiala |
| D346,318 S | 4/1994 | Evans |
| 5,303,471 A | 4/1994 | Liberatoscioli |
| 5,306,285 A | 4/1994 | Miller |
| 5,307,566 A | 5/1994 | Matzo |
| D348,194 S | 6/1994 | Tanis |
| 5,321,892 A | 6/1994 | Sasada |
| 5,341,822 A | 8/1994 | Farr et al. |
| 5,350,317 A | 9/1994 | Weaver |
| D351,907 S | 10/1994 | Matthai |
| D353,888 S | 12/1994 | Raines |
| 5,381,602 A | 1/1995 | Matzo |
| D355,344 S | 2/1995 | Matthai |
| 5,396,706 A | 3/1995 | Fajnsztajn |
| 5,404,779 A | 4/1995 | Break |
| 5,406,710 A | 4/1995 | Zaiser |
| 5,414,935 A | 5/1995 | Braunbach |
| 5,421,231 A | 6/1995 | Break |
| 5,435,066 A | 7/1995 | Bare |
| 5,439,472 A | 8/1995 | Evans |
| 5,454,167 A | 10/1995 | Albery |
| D364,463 S | 11/1995 | Pitzen |
| 5,496,316 A | 3/1996 | Goris |
| 5,505,738 A | 4/1996 | Hempel |
| 5,507,764 A | 4/1996 | Muller |
| 5,540,129 A | 7/1996 | Kalber |
| 5,554,165 A | 9/1996 | Raitt |
| 5,591,170 A | 1/1997 | Spievack |
| 5,628,748 A | 5/1997 | Vicari |
| D379,795 S | 6/1997 | Pitzen |
| 5,637,417 A | 6/1997 | Engmark |
| 5,653,033 A | 8/1997 | McDowell |
| 5,674,119 A | 10/1997 | DesRosiers |
| 5,697,158 A | 12/1997 | Klinzing |
| 5,702,415 A | 12/1997 | Matthai |
| 5,724,740 A | 3/1998 | Bishop |
| 5,758,425 A | 6/1998 | Gallagher |
| 5,792,573 A | 8/1998 | Pitzen |
| 5,846,244 A | 12/1998 | Cripe |
| 5,856,715 A | 1/1999 | Peot |
| 5,878,607 A * | 3/1999 | Nunes et al. .................. 30/124 |
| 5,887,355 A | 3/1999 | Wolff |
| 5,908,424 A | 6/1999 | Bertin |
| 5,933,969 A | 8/1999 | Houben |
| 5,974,674 A | 11/1999 | Kelly |
| 5,979,525 A | 11/1999 | Durney |
| 6,044,559 A | 4/2000 | Holst |
| 6,055,734 A | 5/2000 | McCurry |
| D427,085 S | 6/2000 | Steinhagen |
| 6,106,535 A | 8/2000 | Dross |
| 6,113,618 A | 9/2000 | Nic |
| 6,135,567 A | 10/2000 | Cochran |
| 6,167,626 B1 | 1/2001 | Doumani |
| 6,202,311 B1 | 3/2001 | Nickels, Jr. |
| 6,363,617 B1 | 4/2002 | Frost |
| 6,375,557 B1 | 4/2002 | Spangenberg |
| 6,412,179 B1 | 7/2002 | Ende |
| 6,484,410 B1 | 11/2002 | Meastas |
| 6,488,256 B1 | 12/2002 | Chang |
| 6,488,279 B1 | 12/2002 | Fukuda et al. |
| 6,526,924 B2 | 3/2003 | Soderqvist |
| 6,536,120 B1 | 3/2003 | Langis |
| 6,540,760 B2 | 4/2003 | Austring |
| 6,557,261 B1 | 5/2003 | Buser |
| 6,558,394 B2 | 5/2003 | Lee |
| 6,568,088 B1 | 5/2003 | Ende |
| 6,574,867 B1 | 6/2003 | Bradshaw |
| 6,591,509 B2 | 7/2003 | LeBlanc |
| 6,623,342 B1 | 9/2003 | McDonald |
| 6,678,960 B2 | 1/2004 | Williams |
| 6,681,493 B2 | 1/2004 | Mori |
| 6,682,272 B2 | 1/2004 | Stanfield |
| 6,691,418 B1 | 2/2004 | Lewin |
| 6,723,101 B2 | 4/2004 | Fletcher |
| 6,735,875 B1 | 5/2004 | Eslambolchi |
| 6,739,060 B1 | 5/2004 | Huang |
| 6,775,913 B2 | 8/2004 | Fey |
| 6,785,971 B2 | 9/2004 | McDonnell |
| 6,842,988 B2 | 1/2005 | Johansson |
| 6,865,813 B2 | 3/2005 | Pollak |
| 6,875,222 B2 | 4/2005 | Long |
| 6,890,336 B2 | 5/2005 | Nordman |
| 6,925,917 B2 | 8/2005 | Tilley |
| 6,926,168 B2 | 8/2005 | Duesterhus et al. |
| 6,926,241 B2 | 8/2005 | Garrett |
| 6,932,075 B1 | 8/2005 | Tsao |
| 6,938,532 B2 | 9/2005 | Hofmann |
| 6,953,197 B2 | 10/2005 | Hartmann |
| 6,990,882 B2 | 1/2006 | Schonfelder |
| D519,808 S | 5/2006 | Otsuka et al. |
| D520,834 S | 5/2006 | Furuta et al. |
| 7,043,845 B2 | 5/2006 | Lukens |
| 7,047,650 B2 | 5/2006 | Chen |
| 7,063,000 B2 | 6/2006 | Molburg |
| 7,066,069 B2 | 6/2006 | Ku |
| 7,131,205 B2 | 11/2006 | McDonnell |
| 7,159,323 B2 | 1/2007 | Petrenko |
| 7,207,115 B2 | 4/2007 | Otake |
| 7,219,434 B2 | 5/2007 | Moore |
| 7,225,545 B2 | 6/2007 | Blatz |
| 7,290,342 B2 | 11/2007 | Hartmann |
| 7,328,512 B2 | 2/2008 | Martin |
| 7,346,992 B2 | 3/2008 | Hunger |
| 7,350,517 B2 | 4/2008 | Perez |
| D581,762 S | 12/2008 | Aglassinger |
| D605,488 S | 12/2009 | Aglassinger |
| D606,376 S | 12/2009 | Okuda et al. |
| D611,795 S | 3/2010 | Misaki |
| 7,704,254 B2 | 4/2010 | Walen |
| D619,437 S | 7/2010 | Hattori |
| 2008/0058846 A1 | 3/2008 | Vosough |

FOREIGN PATENT DOCUMENTS

| | | |
|---|---|---|
| DE | 478354 | 6/1929 |
| DE | 505274 | 8/1930 |
| DE | 719969 | 4/1942 |
| DE | 888595 | 9/1953 |
| DE | 3101363 | 12/1981 |
| DE | 3342918 | 6/1985 |
| DE | 48159 | 8/1989 |
| FR | 2283663 | 9/1974 |
| GB | 531802 | 1/1941 |
| GB | 731182 | 6/1955 |
| GB | 2003391 | 3/1979 |
| GB | 2068829 | 8/1981 |
| IT | 322599 | 7/1934 |
| WO | 2005092267 | 10/2005 |
| WO | 2007041794 | 4/2007 |

OTHER PUBLICATIONS

Applicant Response to Written Opinion, Serial No. PCT/US2008/083453, Jun. 29, 2009, 20 pages.
Authorized Officer Ghassem Alie, WIPO, Serial No. PCT/US2008/083453, IPRP, Apr. 15, 2011, 22 pages.
European Patent Office, Application No. 08849444.8, Search Report, Mar. 28, 2012, 5 pages.
Applicant Response to European Search Report, Application No. 08849444.8, Oct. 29, 2012.
European Patent Office, Application No. 08849444.8, Examination Report, Mar. 31, 2013.
Applicant Response to Examination Report, Application No. 08849444.8, May 10, 2013.

(56) References Cited

OTHER PUBLICATIONS

Authorized Officer Lee W. Young, WIPO, Serial No. PCT/US2010/023866, Search Report & Written Opinion, Apr. 5, 2010, 9 pages.
Applicant Response to Written Opinion, Serial No. PCT/US2010/023866, Amendment Under Article 34 & Demand, Dec. 13, 2010.
Authorized Officer Ghassem Alie, WIPO, Serial No. PCT/US2010/023866, IPRP, Nov. 7, 2011, 22 pages.
Non-Final Office Action issued in U.S. Appl. No. 13/201,090. Jun. 18, 2014.
European Patent Office Action issued in Application No. 08849444.8. Jun. 2, 2014.
Response to European Patent Office Action filed in Application No. 08849444.8. Oct. 10, 2014.
Response After Non-Final Action in U.S. Appl. No. 13/201,090. Dec. 1, 2014.
Final Office Action issued in U.S. Appl. No. 13/201,090 Dec. 18, 2014.
Canadian Patent Office Action issued in Application No. 2,705,732. Nov. 3, 2014.

* cited by examiner

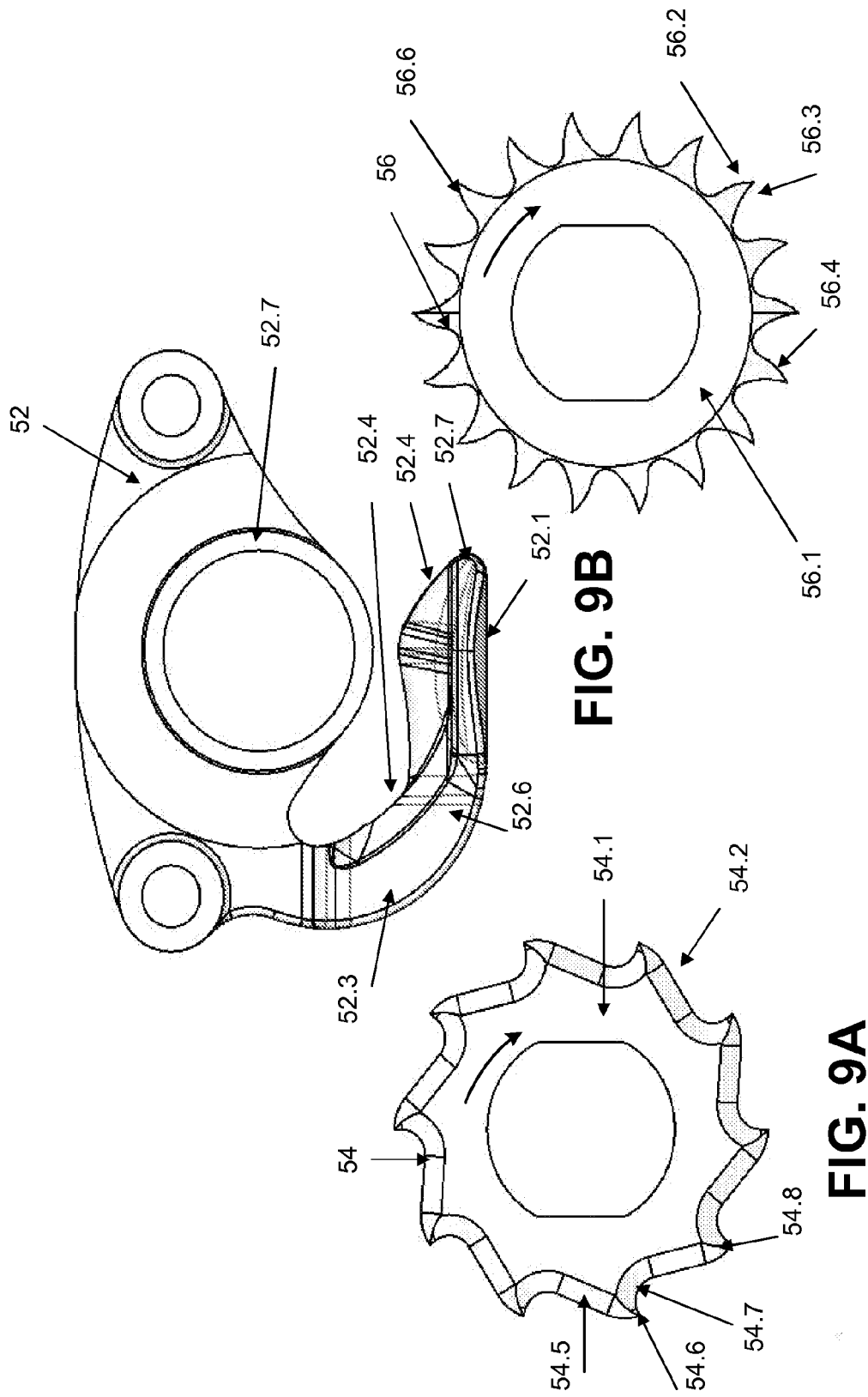

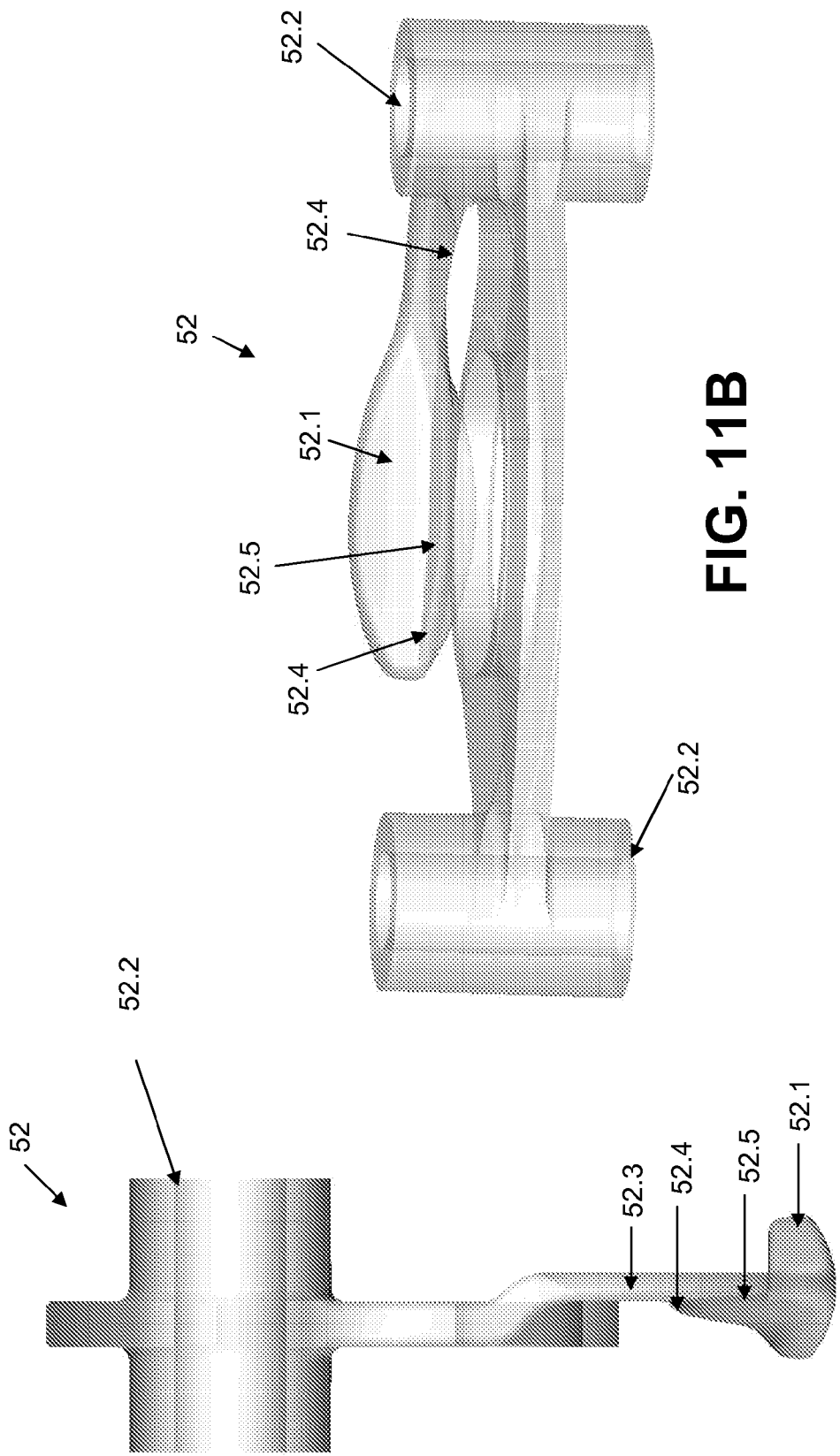

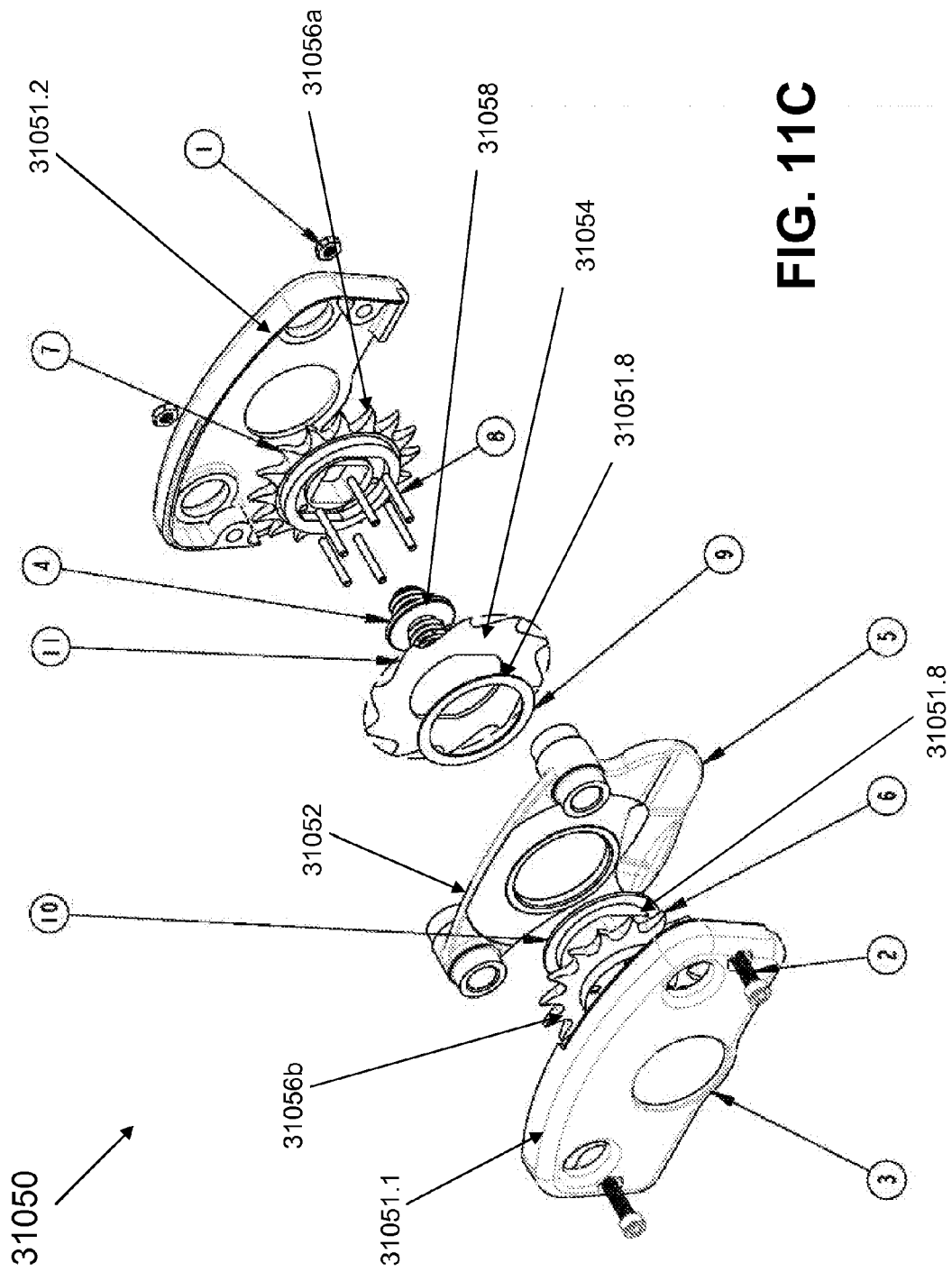

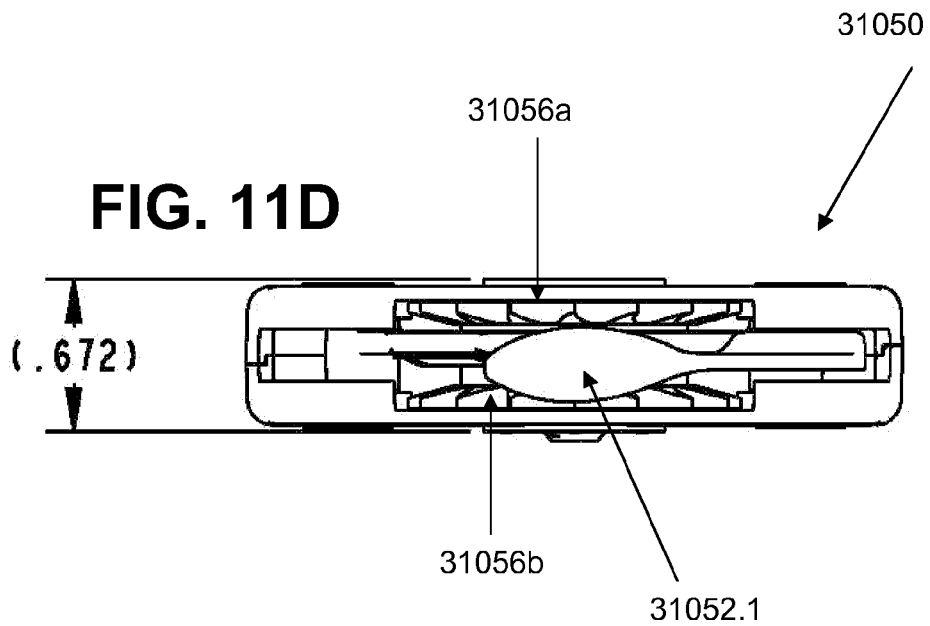
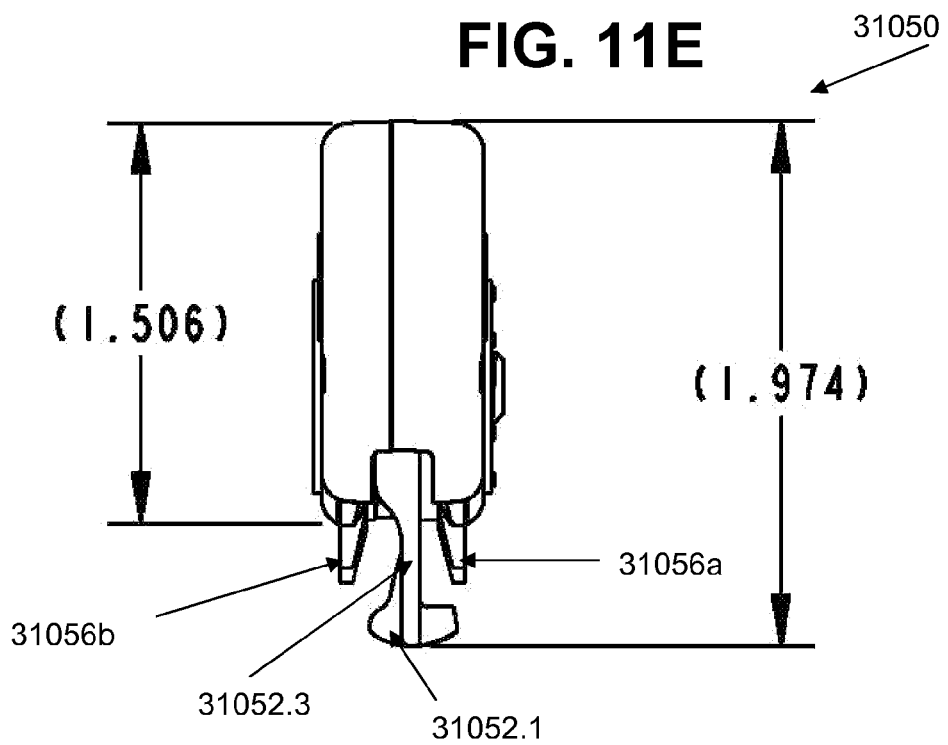

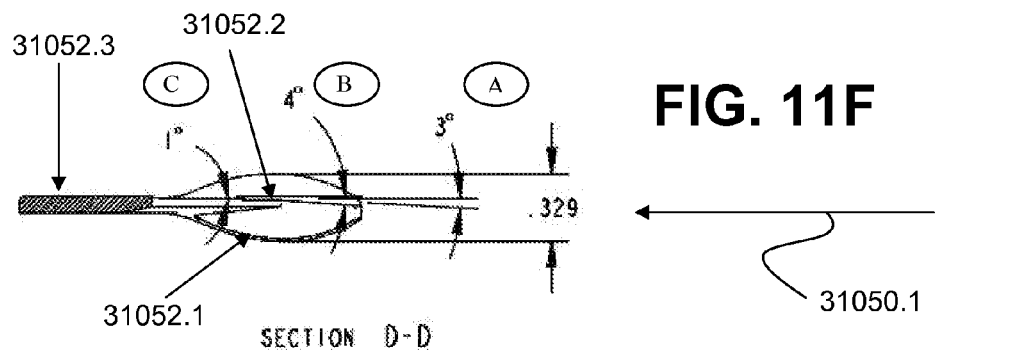
FIG. 11F
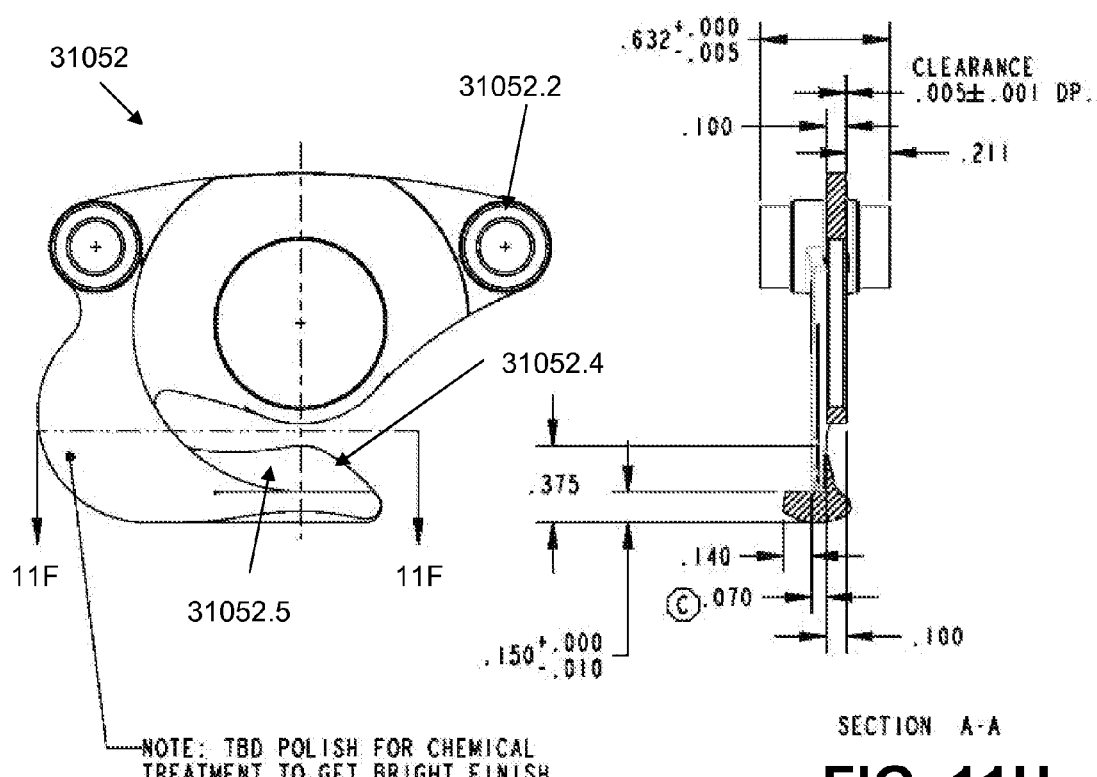
FIG. 11G
FIG. 11H

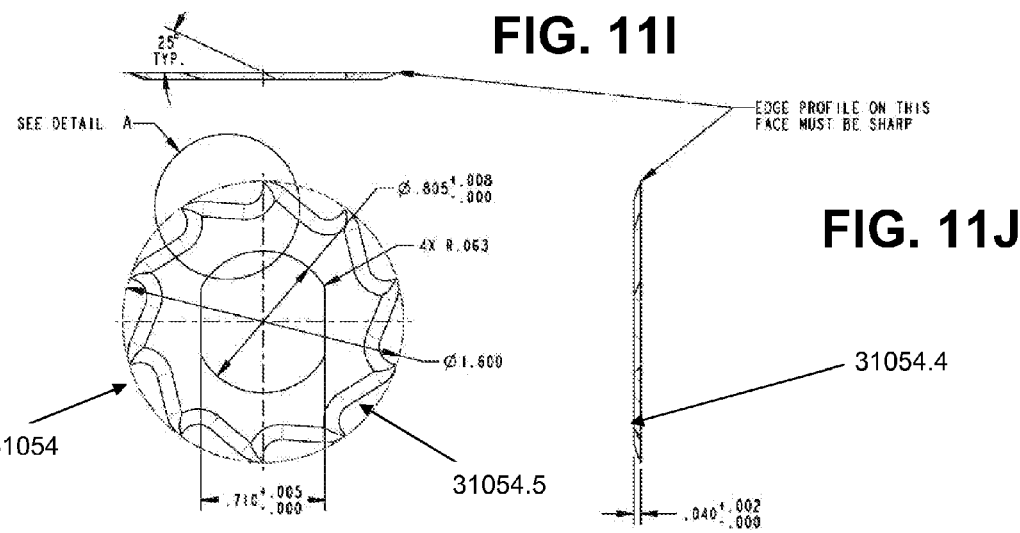
FIG. 11I
FIG. 11J
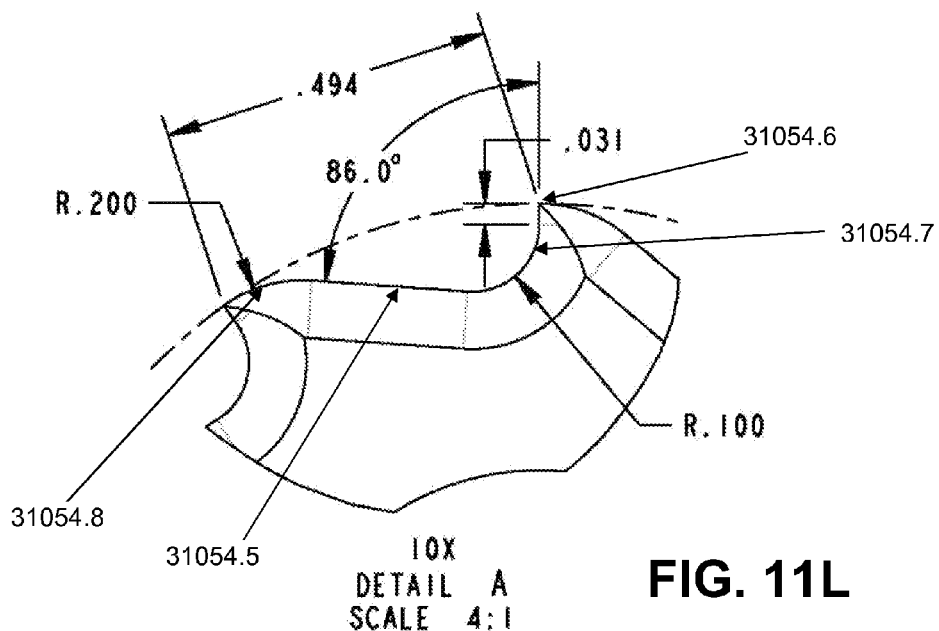
FIG. 11K
FIG. 11L

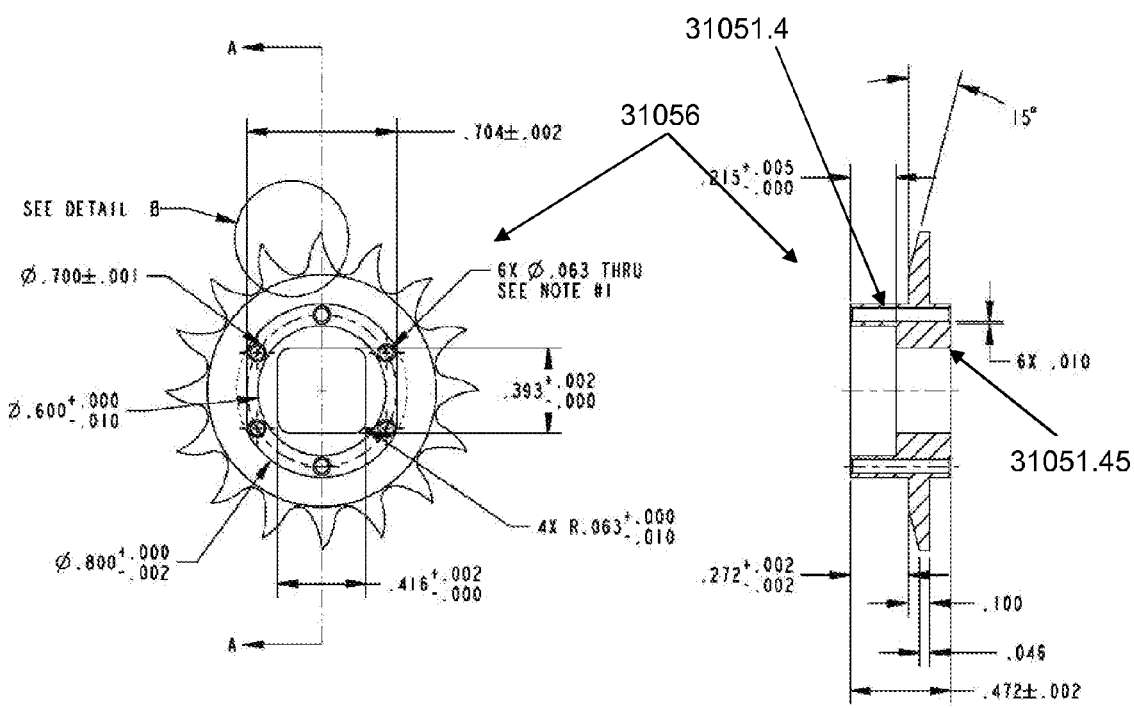
FIG. 11M
FIG. 11N
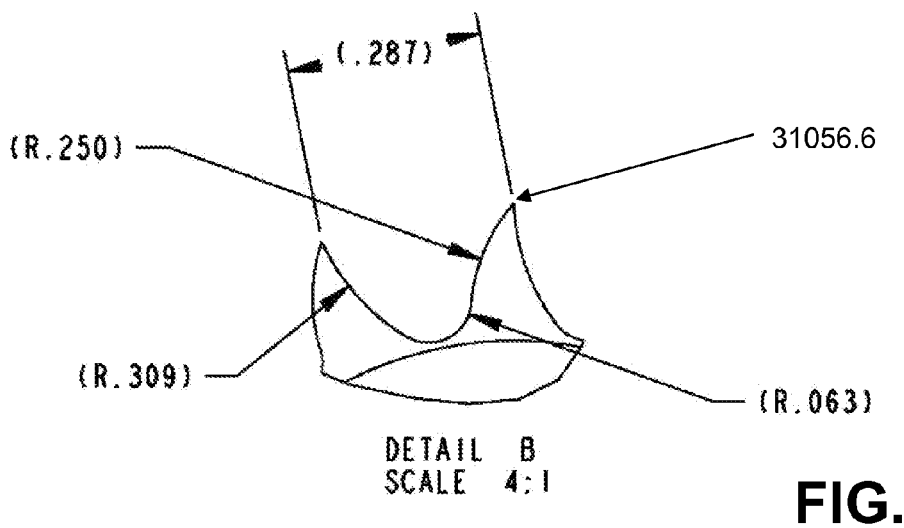
FIG. 11 O

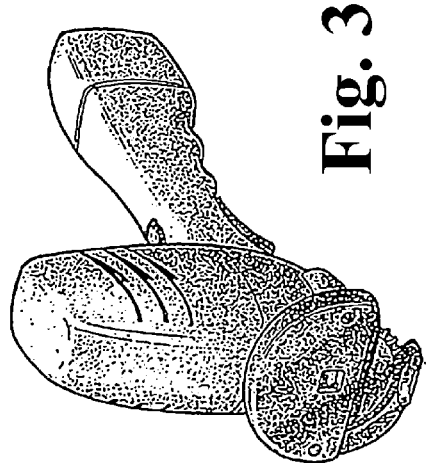
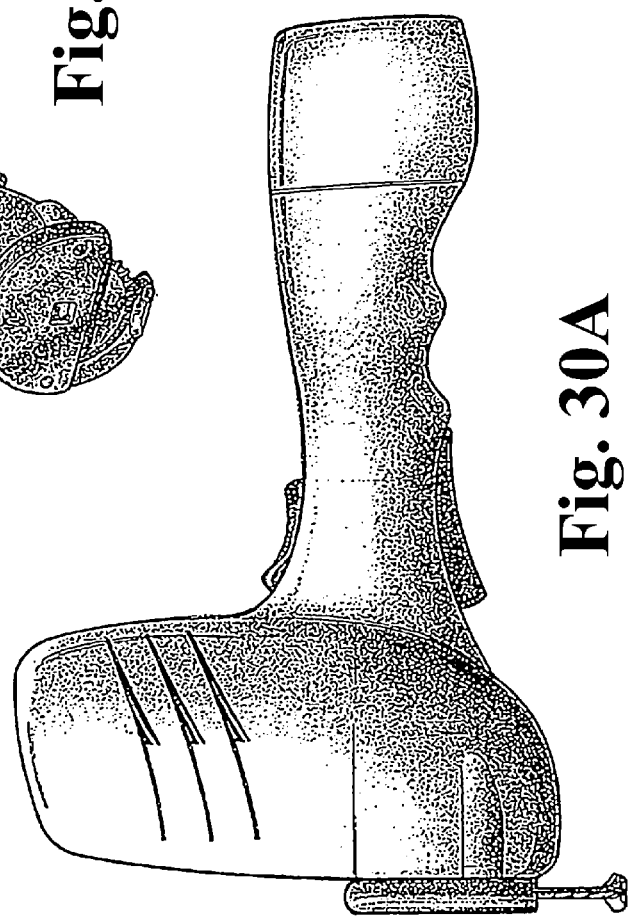

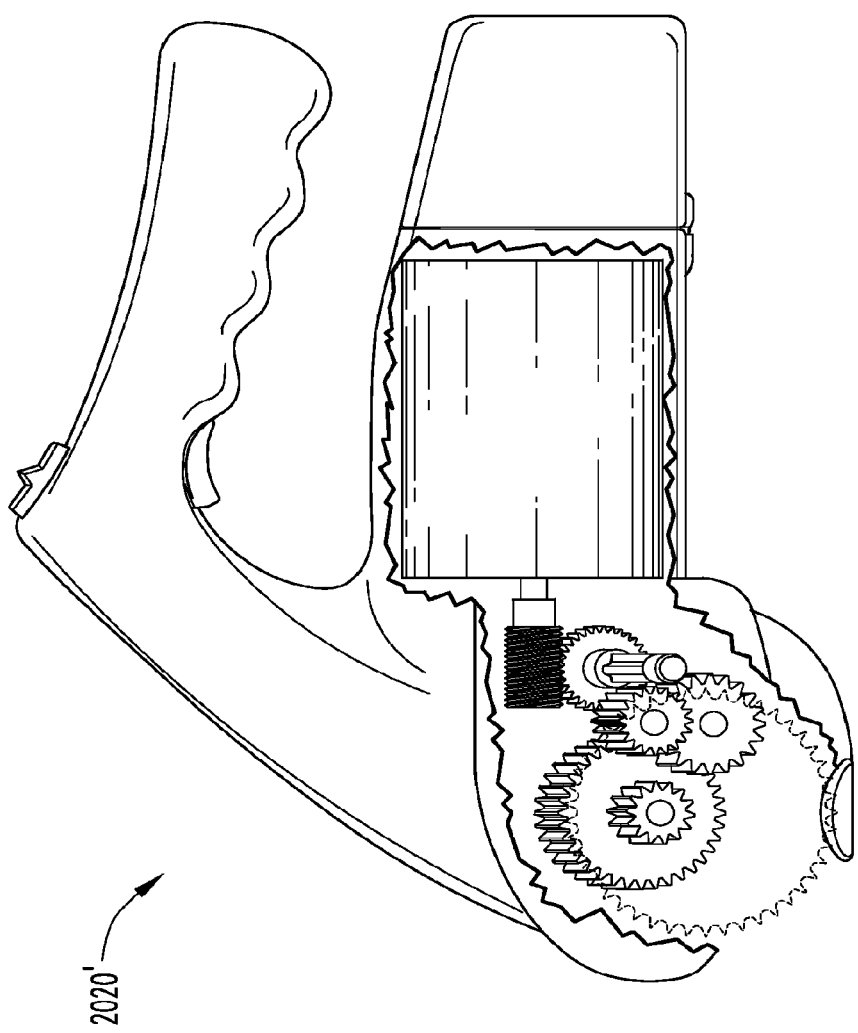

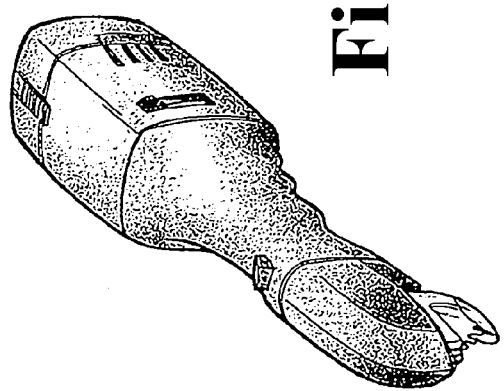
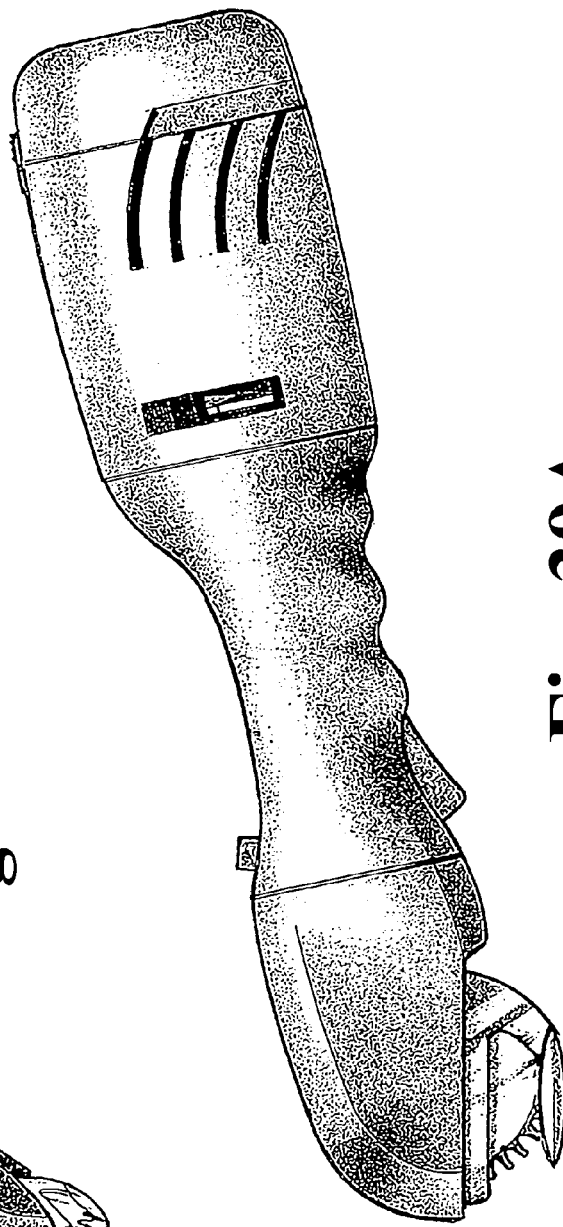
Fig. 39B
Fig. 39A

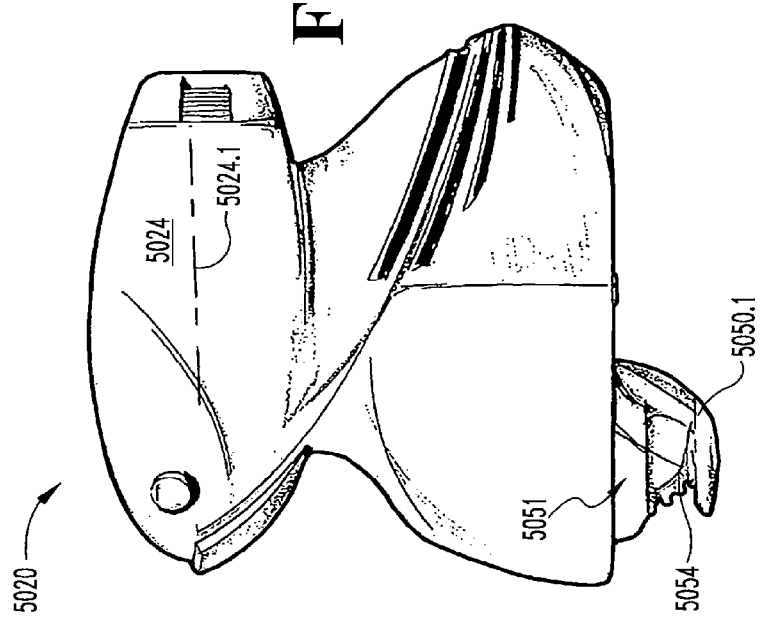
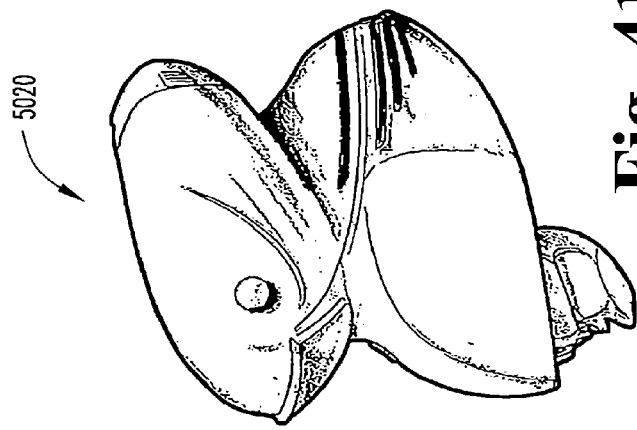
Fig. 41A
Fig. 41B

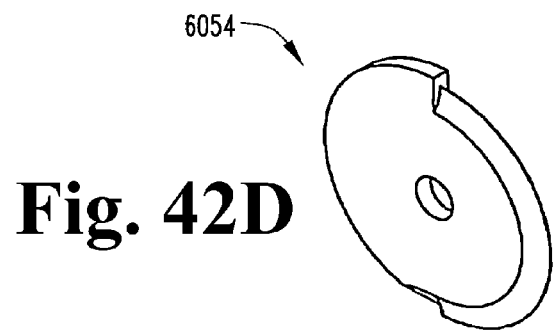
Fig. 42D
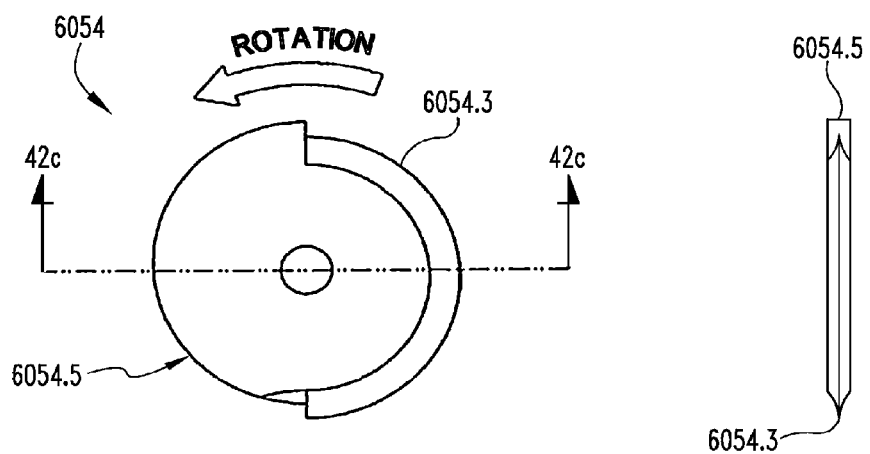
Fig. 42A  Fig. 42B
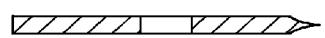
Fig. 42C

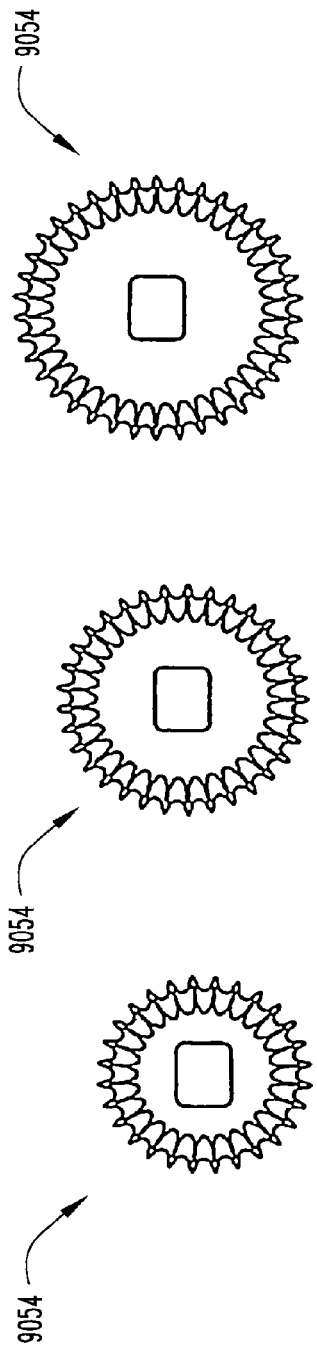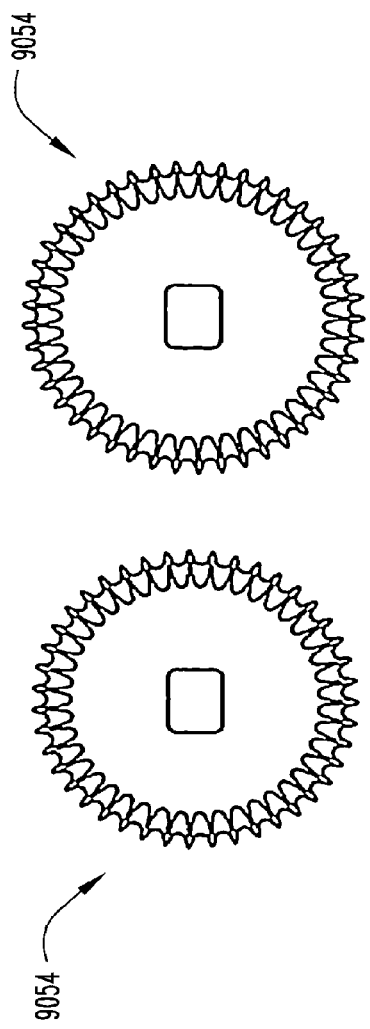
Fig. 48A  Fig. 48B  Fig. 48C  Fig. 48D  Fig. 48E

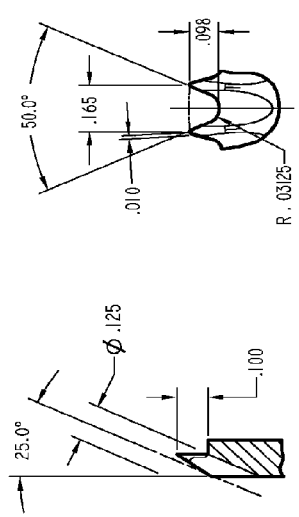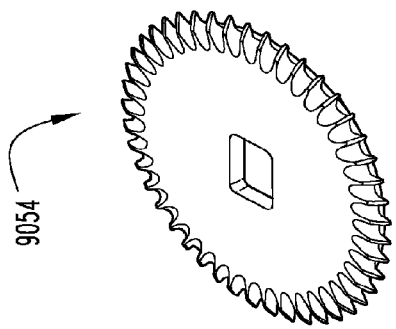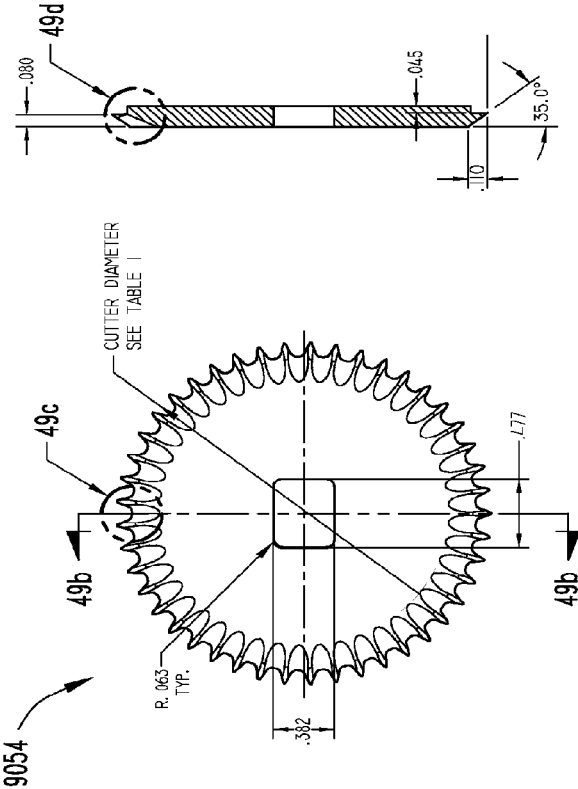
Fig. 49A Fig. 49B Fig. 49C Fig. 49D Fig. 49E

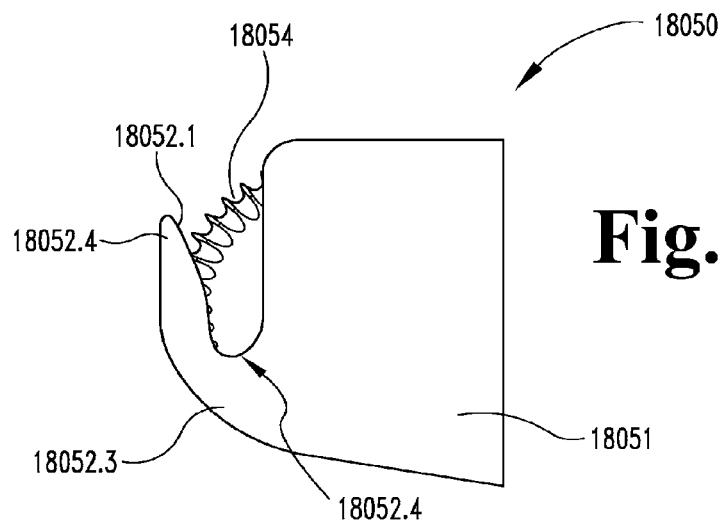
Fig. 61A
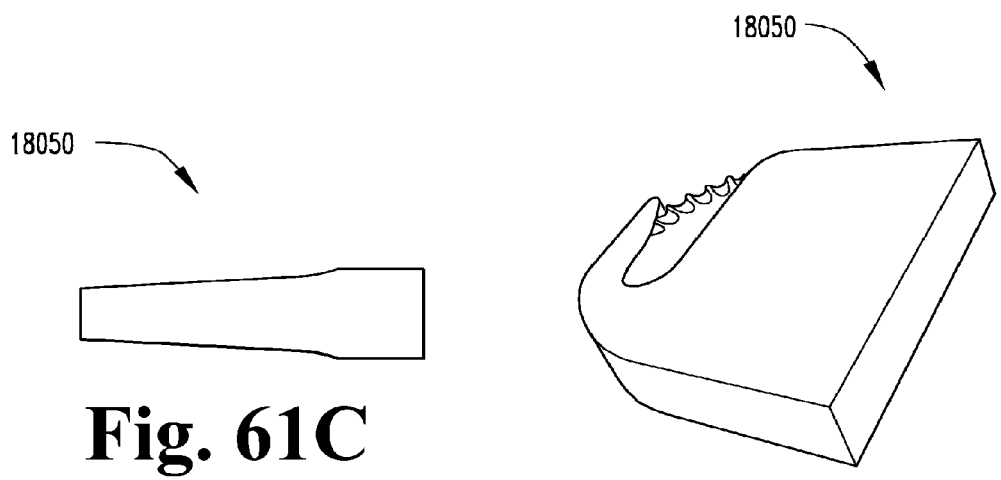
Fig. 61C
Fig. 61B

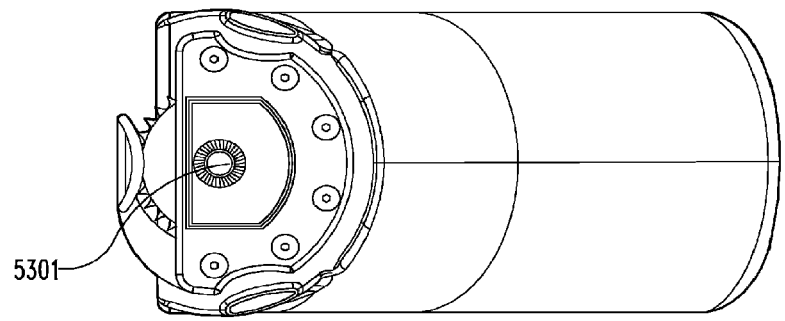
Fig. 73A
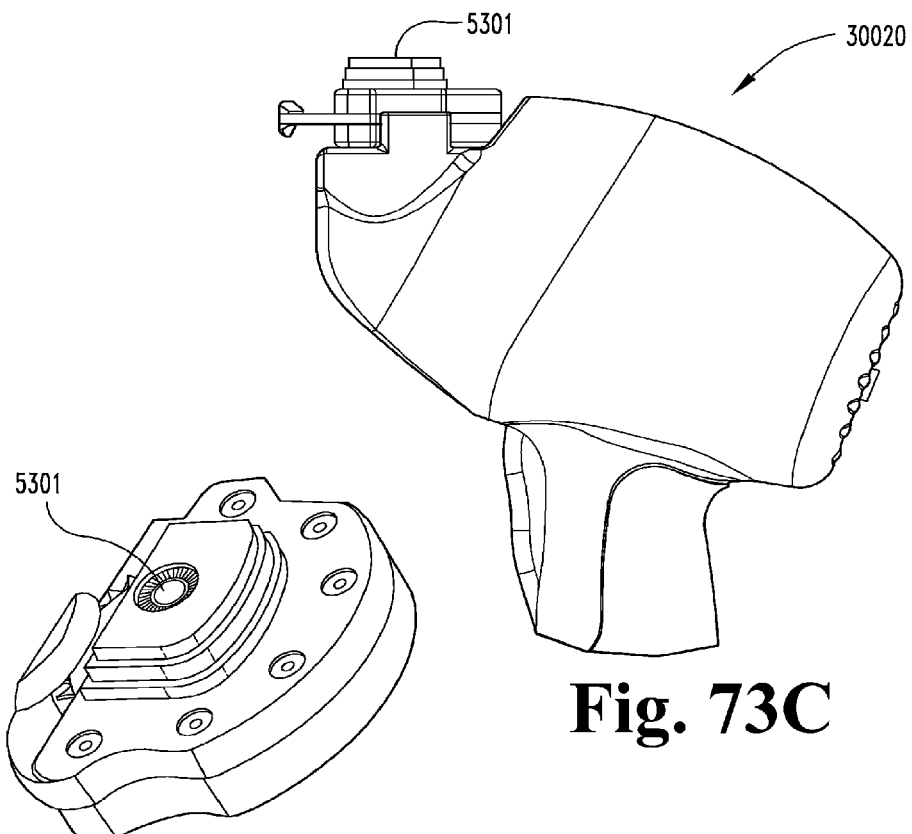
Fig. 73C
Fig. 73B

CAST REMOVAL SYSTEM

CROSS REFERENCE TO RELATED APPLICATIONS

This application is a national stage application of PCT Patent Application No. PCT/US08/83453, filed Nov. 13, 2008, which claims the benefit of priority to U.S. Provisional Patent Applications Ser. No. 61/002,842, filed Nov. 13, 2007 entitled CAST REMOVAL SYSTEM I; Ser. No. 61/010,551, filed Jan. 9, 2008, entitled CAST REMOVAL SYSTEM II; Ser. No. 61/072,996, filed Apr. 4, 2008, entitled CAST REMOVAL SYSTEM III; and Ser. No. 61/104,061, filed Oct. 9, 2008, entitled CAST REMOVAL SYSTEM IV, all of which are incorporated herein by reference.

FIELD OF THE INVENTION

The present invention pertains to methods and apparatus for cutting through a material, and in particular to methods and apparatus for cutting through an orthopedic cast.

BACKGROUND

Casts used to set broken bones or other injuries to limbs generally consist of a hard outer shell, a sleeve, and an internal fabric or wrapping. The outer shell is typically made of layers of fiberglass or plaster. The inner wrappings are typically made from flexible woven or non-woven materials, such as cotton, polyester or other fibers. The hard outer cast shells typically are removed by using powered oscillating saws, which can be noisy and may create substantial fine debris. In order to prevent injury to patients, oscillating saws are usually operated at high frequency and low amplitude. However, oscillating saws can still cause burns or abrasions, and in many cases cause fear in many patients, especially small children.

What is needed are improved methods and apparatus for removal of a cast. Various embodiments of the present invention provide this in novel and unobvious ways.

SUMMARY OF THE INVENTION

One aspect of the present invention pertains to an apparatus for cutting a layer of material at a low speed with high torque. In one embodiment, the apparatus includes an electric motor. In other embodiments, the apparatus includes a wheel having a plurality of shearing sectors being rotationally driven by an electric motor. Still other embodiments include a foot having a shearing surface adapted and configured for sliding contact with the face of said wheel. Further embodiments include an electronic controller with software operably connected to said motor.

Another aspect of the present invention pertains to a method for cutting a layer of material. Further embodiments pertain to providing a first plurality of teeth arranged in a first pattern about a first axis, and a second plurality of shearing sectors arranged in a second pattern about a second axis. Still further embodiments pertain to engaging the material with at least one tooth and rotating the first pattern about the first axis in a rotational direction and at a rotational speed. Another embodiment pertains to moving a portion of the material by rotating the first pattern. Yet further embodiments include rotating the second pattern about the second axis in the rotational direction and at the rotational speed and splitting the portion with the shearing sector.

Another aspect of the present invention pertains to an apparatus for cutting a layer of material. Further embodiments include an electric motor having an output speed and an output torque. Still further embodiments include a gear train having a driven member for receiving the output speed and output torque of a motor, a gear train including a worm gear pair, the first pair providing a speed reduction and torque increase to the driving member of the gear train. Yet other embodiments include a wheel including a plurality of shearing sectors arranged in a first pattern about a first rotational axis, each sector having a sharp edge, the wheel being rotationally driven by the driving member. Still further embodiments include a handle adapted and configured for being held by a human operator, the handle supporting a wheel, a gear train, and a motor.

Still further aspects of the present invention pertain to an apparatus for cutting a layer of material. Other embodiments include a first wheel including a plurality of shearing sectors arranged in a first pattern about a rotational axis, each sector having a sharp edge, a wheel being adapted and configured for complete rotation about the axis. Still further embodiments include a second wheel including a plurality of teeth, each tooth being adapted and configured for pressing the surface of the material. Yet other embodiments include a structural member for establishing the location of the axis relative to the material, the member having an arm and a foot extending from an end of an arm, the arm extending along a peripheral side of the first wheel, the foot extending under the first wheel, wherein the first wheel and second wheel are coupled together for simultaneous rotation.

Another aspect of the present invention pertains to a method for cutting material. Some embodiments include providing an electric motor, a reduction gear train, a foot having shearing surface, and a shearing wheel having a sharp edge. Still other embodiments include a driving the gear train by the electric motor at a first high speed and a first low torque. Yet other embodiments include driving the shearing wheel by the gear train at a second lower speed and a second higher torque; cutting the material by shearing between the edge of the wheel and the shearing surface; and automatically advancing the material past the shearing edge at about the same linear velocity as the edge.

A further aspect of the present invention pertains to a portable apparatus for cutting material. One embodiment includes an electric motor. Further embodiments include a wheel having a sharp edge, the wheel being rotationally driven about a rotational axis by an electric motor. Still further embodiments include a foot located across from a section of the edge of the wheel; and a handle shaped for being held by the hand of a human operator, the handle includes a central axis, a handle supporting the wheel, foot, and motor. Still other embodiments include that the material is cut along a path by the sharp edge, the path being between the foot and the section of the wheel, and the path is generally perpendicular to the central axis.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these myriad combinations is excessive and unnecessary.

DESCRIPTION OF THE DRAWINGS

FIG. 9A is a front planar view of a portion of the apparatus of FIG. 8.

FIG. 9B is a front planar view of a portion of the apparatus of FIG. 8.

FIG. 9C is a front planar view of a portion of the apparatus of FIG. 8.

FIG. 11A is a right side elevational view of a portion of the apparatus of FIG. 8.

FIG. 11B is a top and frontal perspective view of the apparatus of FIG. 11A.

FIG. 11C is an exploded perspective view of a cutting assembly according to another embodiment of the present invention.

FIG. 11D is a bottom view of the assembled apparatus of FIG. 11C.

FIG. 11E is an end elevational view of the apparatus of FIG. 11D.

FIG. 11F is a top plan view of a portion of the apparatus of FIG. 11G as taken along line 11F-11F of FIG. 11G.

FIG. 11G is a front planer view of a portion of the apparatus of FIG. 11C.

FIG. 11H is an orthogonal cut-away view of the apparatus of FIG. 11G taken along the center line.

FIGS. 11I, 11J, and 11K are top, end, and frontal orthogonal views, respectively, of a portion of the apparatus of FIG. 11C.

FIG. 11L is a close-up of a portion of FIG. 11K.

FIG. 11M is a front planer view of a portion of the apparatus of FIG. 11C.

FIG. 11N is a cross-sectional view of the apparatus of FIG. 11M as taken along the center line.

FIG. 11O is a close-up of a portion of the apparatus of FIG. 11M.

FIG. 30A is a side elevational view of an apparatus according to another embodiment of the present invention.

FIG. 30B is a perspective view of the apparatus of FIG. 30A.

FIG. 38A is a partial cutaway view of an apparatus according to another embodiment of the present invention.

FIG. 39A is a side elevational view of an apparatus according to another embodiment of the present invention.

FIG. 39B is a front, left side perspective view of an apparatus of FIG. 39A.

FIG. 41A is a side elevational view of an apparatus according to another embodiment of the present invention.

FIG. 41B is a front, left side perspective view of the apparatus of FIG. 41A.

FIG. 42A shows various views of a splitting and shearing wheel according to another embodiment of the present invention.

FIG. 42B is a side elevational view of the apparatus of FIG. 41A.

FIG. 42C is a cross sectional view of the apparatus of FIG. 42A as taken along line 42C-42C.

FIG. 42D is a perspective view of the apparatus of FIG. 42A.

FIG. 48A shows a cutting wheel according to one embodiment of the present invention having 28 teeth, and having a diameter of 1.474 inches.

FIG. 48B shows a cutting wheel according to one embodiment of the present invention having 33 teeth, and having a diameter of 1.736 inches.

FIG. 48C shows a cutting wheel according to one embodiment of the present invention having 38 teeth, and having a diameter of 1.998 inches.

FIG. 48D shows a cutting wheel according to one embodiment of the present invention having 43 teeth, and having a diameter of 2.260 inches.

FIG. 48E shows a cutting wheel according to one embodiment of the present invention having 45 teeth, and having a diameter of 2.365 inches.

FIG. 49A is a front elevational view of a wheel from the family of FIG. 48.

FIG. 49B is a side elevational view of the apparatus of FIG. 49A.

FIG. 49C is a perspective view of the apparatus of FIG. 49A.

FIG. 49D is a close up of a portion of FIG. 49B.

FIG. 49E is a close up of a portion of FIG. 49A.

FIG. 61A shows a side elevational view of a portion of a cutting assembly according to another embodiment of the present invention.

FIG. 61B is a perspective view of the apparatus of FIG. 62A.

FIG. 61C is an orthogonal view of the apparatus of FIG. 61A.

FIG. 65A shows a side elevational view of a keel assembly according to another embodiment of the present invention.

FIG. 65B shows a perspective view of the keel assembly of FIG. 65A.

FIG. 66A shows a side elevational view of a keel assembly according to another embodiment of the present invention.

FIG. 66B shows a perspective view of the keel assembly of FIG. 66A.

FIG. 67A shows a side elevational view of a keel assembly according to another embodiment of the present invention.

FIG. 67B shows a perspective view of the keel assembly of FIG. 67A

FIG. 68 is a perspective view of a cutting assembly according to another embodiment of the present invention.

FIG. 69 is an exploded view of the apparatus of FIG. 68.

FIG. 70A shows a side view of the apparatus of FIG. 68.

FIG. 70B shows a top view of the apparatus of FIG. 68.

FIG. 71A shows a frontal view of another apparatus according to another embodiment of the present invention, and incorporating a rotating shearing surface 5103.

FIG. 71B shows a close up of the frontal view of FIG. 71A.

Figure 72A:
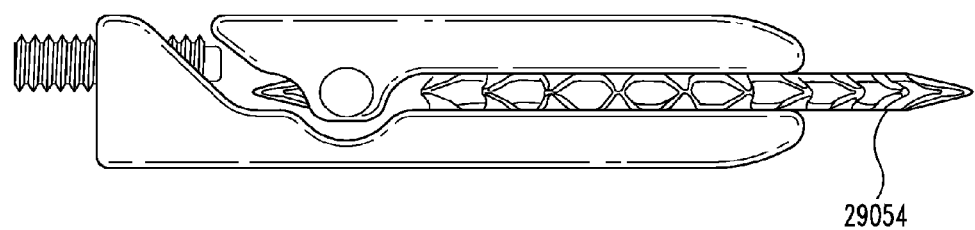

FIG. 72A shows top of apparatus according to other embodiments of the present invention.

Figure 72B:
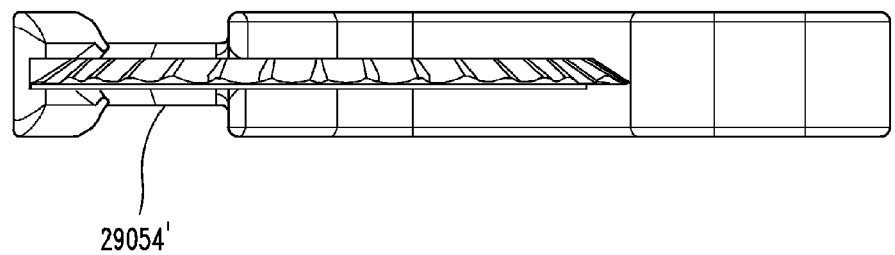

FIG. 72B shows an end view of an apparatus according to other embodiment of the present invention.

FIG. 73A shows a top view apparatus according to another embodiment of the present invention.

FIG. 73B is a perspective view of a portion of the apparatus of FIG. 73A.

FIG. 73C is a side elevational view of the apparatus of FIG. 73A.

Figure 74:
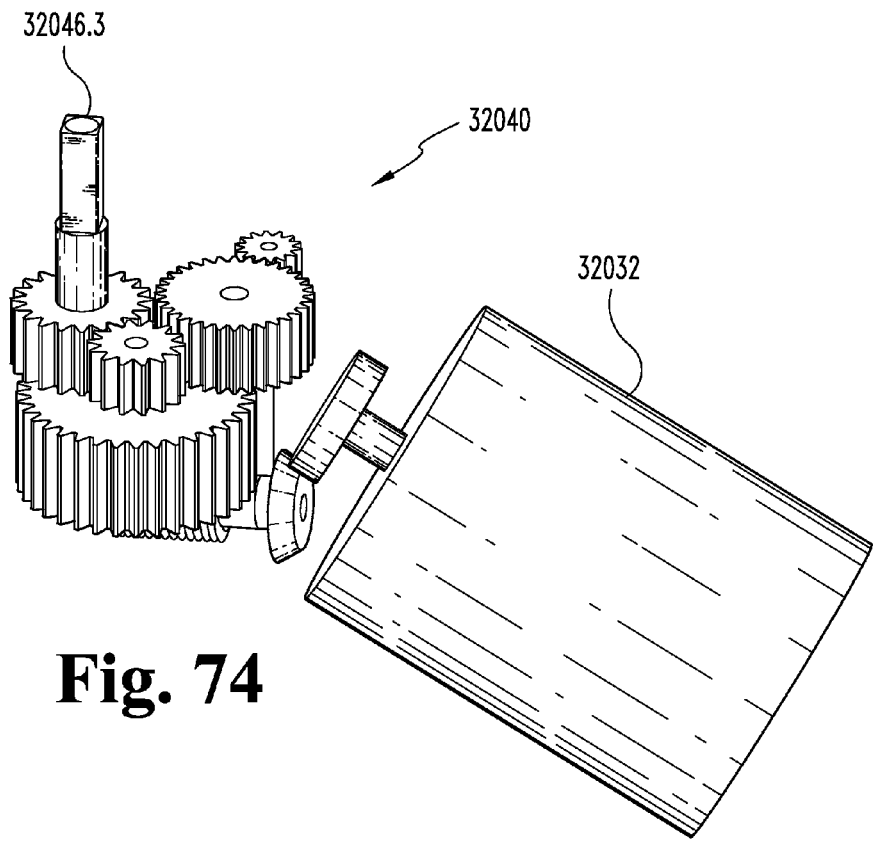

FIG. 74 is a perspective view of an apparatus according to another embodiment of the present invention.

Figure 75:
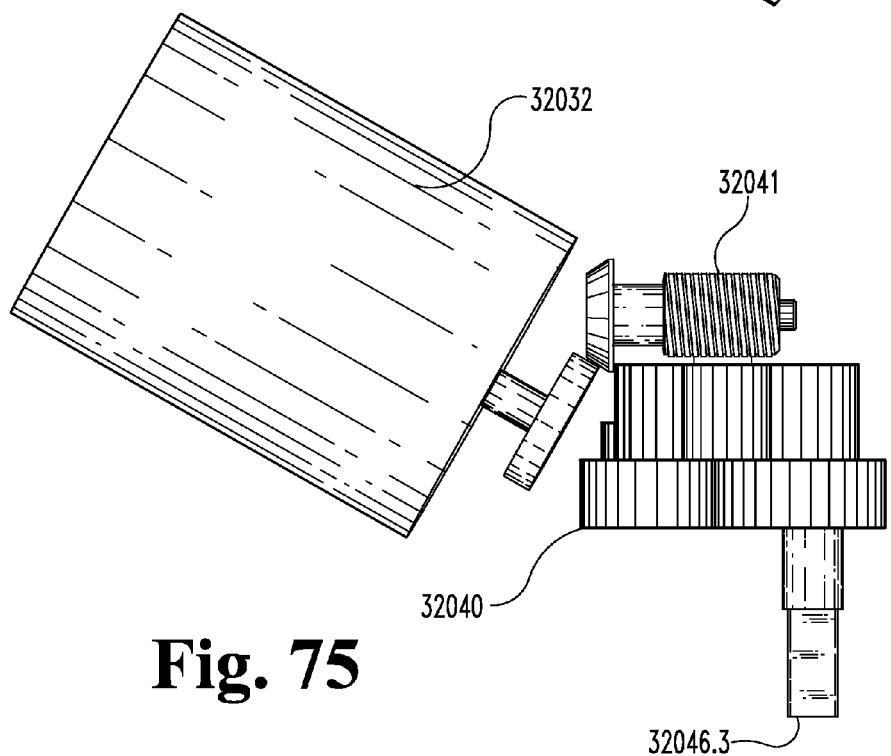

FIG. 75 is a view of the apparatus of FIG. 74.

Figure 76B:
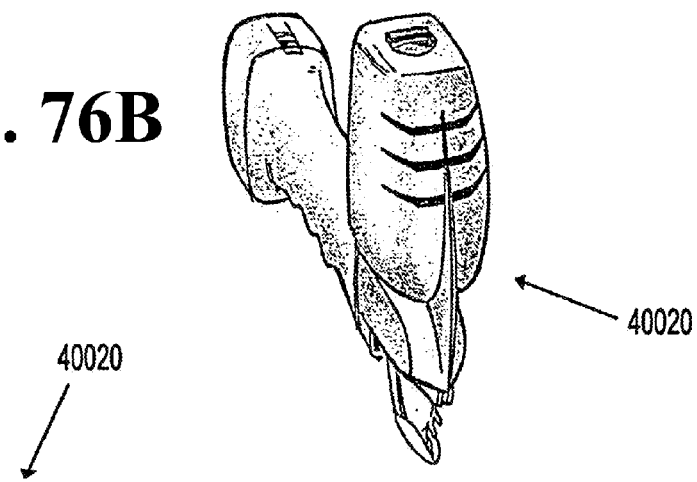
Figure 76A:
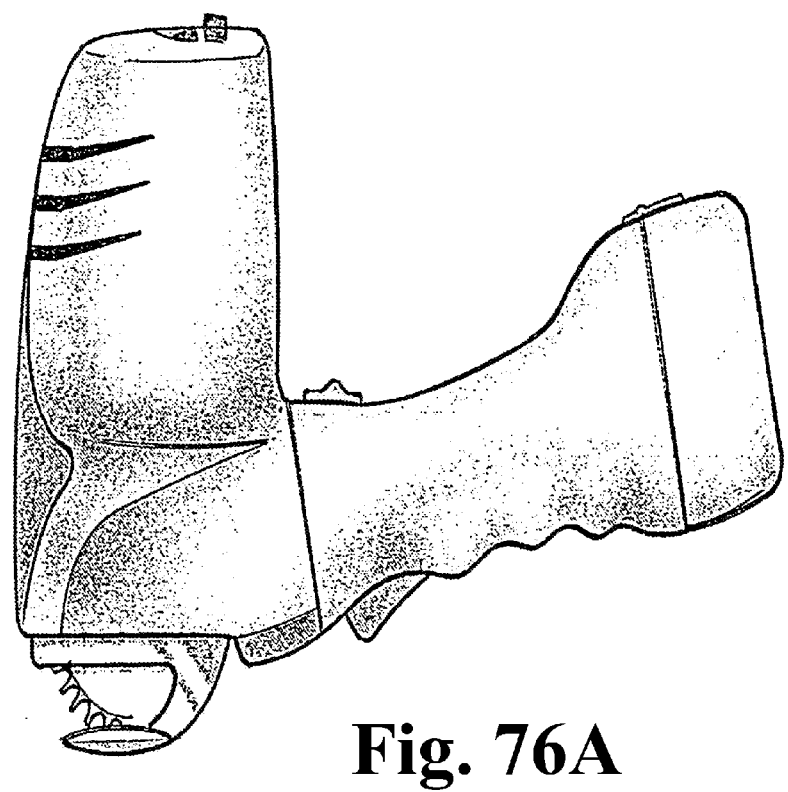

FIG. 76A is a side elevational view of an apparatus according to another embodiment of the present invention.

FIG. 76B is a perspective view of the apparatus of 76A.

DESCRIPTION OF THE PREFERRED EMBODIMENT

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of the invention, with no single embodiment including an apparatus, process, or composition that must be included in all embodiments, unless otherwise stated.

Unless stated otherwise, the use of an N-series prefix for an element number (NXXX.XX) refers to an element that is the same as the non-prefixed element (XXX.XX), except as shown and described thereafter. As an example, an element 10020.1 would be the same as element 20.1, except for those different features of element 10020.1 shown and described. Further, common elements and common features of related elements may be drawn in the same manner in different figures, and/or may use the same symbology in different figures. As such, it is not necessary to describe the features of 10020.1 and 20.1 that are the same, since these common features are apparent to a person of ordinary skill in the related field of technology. Although various specific quantities (spatial dimensions, temperatures, pressures, times, force, resistance, current, voltage, concentrations, wavelengths, frequencies, etc.) may be stated herein, such specific quantities are presented as examples only.

Various embodiments of the present invention pertain to apparatus and methods for cutting a layer of material with a quiet, clean, motorized shearing (or splitting or severing) action. The apparatus and methods described herein are applicable to cutting many different types of material, such as plaster, fiberglass, wood, sheet metal, and other preferably thin layers of material. In several embodiments, there are apparatus adapted and configured for cutting and removing a plaster, cloth, and fiberglass orthopedic cast placed around a limb of a patient.

In some embodiments, the apparatus and methods are directed toward low speed, high torque shearing applications. A splitting or shearing or severing device shears through the material, and in particular through the hard, plaster portion of the cast. Various embodiments further include sharp edged cutting surfaces that the material passes over, which are adapted and configured for shearing the softer cloth material of the cast. In some embodiments, the splitting or shearing device is a generally cylindrical wheel that has a plurality of shearing shaped sectors located around the periphery of the wheel. In yet other embodiments, the sharp edged cutting of the softer material is accomplished by moving the material previously split by the splitting device over a sharp edge, such as a razor edge. In yet other embodiments, the sharp edge is on the splitting wheel, or located on a second wheel.

Some embodiments include an arm that extends around one side of the splitting or shearing wheel, the end of the arm having a foot that extends under the wheel. In those embodiments directed toward removal of orthopedic casts, this foot is located between the splitting wheel and the patient, such that the cast material is directed between the foot and the splitting wheel.

In some embodiments, the foot includes a shearing surface that extends upward toward the splitting or shearing wheel, and is located such that a face of the splitting or shearing wheel is in sliding contact with the shearing surface. In such embodiments the shearing action occurs by the action of the shearing sector pressing against the material that is being supported along the top of the shearing surface. In some embodiments it is advantageous for this top edge of the shearing surface to have a squared off edge having a relatively small radius of curvature, so as to support the material to be cut as closely as possible to the face of the cutting wheel. In yet other embodiments, the leading edge of the foot has a razor-type surface to assist in advance cutting of the soft material on the inside of the cast. In yet other embodiments, the heal portion of the arm (where the foot connects to the arm) has a razor-type edge for assistance in cutting the soft material that has already been split.

Yet other embodiments of the present invention pertain to a hand-held, battery operated cutting device that shears a material with a high torque, low speed shearing action. In one embodiment, the material is automatically advanced through a scissors-type shearing action at about 0.8 inches per second, although other embodiments of the present invention contemplate material flow speeds of as high as about 3 inches per second. In some embodiments the torque applied to the shearing wheel (which produces the scissors-type action) is about fifty to one hundred and fifty foot-pounds (force). It has been found that a quiet, low dust-generating shearing action within these ranges provides acceptable performance in shearing an orthopedic cast. However, other embodiments of the invention are not so constrained, and as an example, in those applications where sheet metal is sheared, the shearing speed ranges as low as about two-tenths of an inch per second.

In yet other embodiments of the present invention, the low linear velocity of the shearing edge is approximately matched to means for automatically advancing the material at about the same speed. In some embodiments, the flowrate at which material passes by the shearing station is the same as the linear velocity of the shearing edge with result that very little debris is generated from the cutting action. However, other embodiments of the present invention contemplate the use of a low speed, high torque shearing action with means for automatically advancing the material at a speed different than the linear velocity of the shearing edge.

In some embodiments, the means for automatically advancing the material is accomplished at a substantially constant velocity. Velocity is generally maintained by an electronic controller (preferably operating a software algorithm) that automatically adjusts the power provided by the motor as the toughness of the material being cut varies (such as for an orthopedic cast of varying thickness, or a layer of wood of varying thickness).

In another embodiment of the present invention, there is a hand-held, motorized shearing assembly that operates at one of a plurality of predetermined material flow velocities. In one embodiment, there is a trigger switch preferably operated by a finger of the operator. Over a first range of switch movement, the linear velocity of the shearing wheel (and in some embodiments, further of the advancing wheel) is held substantially constant at a first linear velocity. Further movement of the switch into a second, predetermined range of movement operates the shearing wheel (and possibly the advancing wheel) at a second, higher, "boost" speed. This latter, second, boosted speed can be useful in the shearing of orthopedic casts, especially when the path of the shearing wheel is relatively straight along the cast, with the slower speed being helpful when the cutting device must follow a curved path (such as for a cast that holds an arm of a patient bent at the elbow).

In another embodiment of the present invention, there is an advancing wheel having a plurality of teeth that are adapted and configured for pressing contact, and in some embodiments penetration into the outer surface of an orthopedic cast having an external woven material. As one example, some orthopedic cast have an exterior of a cross woven fiberglass matte, with a standard spacing between adjacent threads, which thus establishes a "hole pattern" in the woven material. In some embodiments, the linear distant between adjacent teeth of the advancing wheel are adapted and configured to be even multiples of this hole pattern. Such spacing increases the likelihood that as a tooth penetrates into the outer surface of the cast, and then moves the cast, that the next tooth will not necessarily fray the woven material which would be the case if the tooth pattern were not a multiple of the weave pattern. However, the present invention is not so constrained and further, various embodiments of the present invention are adapted and configured for shearing any variety of orthopedic cast material, including Goretex®.

In yet another embodiment of the present invention there is a shearing wheel that includes around its periphery a plurality of cutting sectors arranged such that they have a "wave" appearance. In some embodiments, there are eight to ten shearing sectors (or waves) around the periphery, although the present invention contemplates embodiments with as few as one shearing sector (or one wave) on a periphery of a wheel, and with as many as about fifteen shearing sectors. In one embodiment, the wave shape begins the shearing action with a leading portion adapted and configured to plunge substantially vertically with a tip or apex into the material. Following this plunging action, a less curved shearing sector advances downward of the uncut material, in a manner analogous to the motion of a blade on a hand-held paper cutter. Following this central shearing section is a close-out section that is radiused toward the tip or apex of the next shearing section, such that at the tip the shearing sector is closed out approximately tangentially to the surface of the material.

In yet other embodiments, the apparatus includes a support member that places a downwardly extending arm with a forward extending foot around the back (aft) periphery of the shearing wheel. After the material is split by the means for shearing the material (which can be any of the shearing or splitting devices shown herein), the split material progresses aftward and goes past on either side of the arm. The forward-projecting foot reaches under the shearing wheel, such that the material flowpath (and the locus of the shearing operation occurs between the edge of the shearing wheel and the top of the foot). The bottom of the foot thus protects the patient.

In some embodiments, the foot includes a shearing surface that projects upward and is generally parallel to a face of the shearing wheel. This upwardly projecting surface has the appearing of a "shark fin" or "camel back." Preferably, the top surface of the shark fin has a sharp, right-angle edge, so as to provide good shearing action relative to the cutting sectors. In yet other embodiments, the forward edge of the shark fin has a sharp surface, and in some embodiments a razor-type surface, for partial, advance cutting of the underside of the layer of material. In yet other embodiments, the aft portion of the foot (the "heel" or where the foot connects to the arm) is further adapted and configured to have a sharp edge, and in some embodiments, a razor-type edge, to complete, if necessary, the cutting of any soft material that was not sheared apart by the coaction of the shearing sectors against the shearing surface. In yet other embodiments, these razor-type edges are replaceable, and are held in by means such as one or more set screws.

Broadly, described here are material severing devices and specifically, devices for cast removal from humans and animals. One embodiment described here comprises an assembly included a housing containing an electric motor, a mechanical gearing transmission component, a cutting mechanism designed to pierce and sever the cast and advance along the cast while cutting it, and a leg and foot mechanism whereas the foot extends along the underside of the cast to prevent the cutter from making contact with the skin.

The mechanical gearing transmission component would be designed to provide a slow rotation of the cutter while providing sufficient torque so as to pierce and sever a pathway down the length of a cast. While one embodiment would utilize a gearing transmission component, any means of conveying rotary motion might be utilized such as, for example, pulleys and belts or chains and sprockets. The cutter described could also provide for the deformation of the cast at the severed pathway allowing for a clear pathway, and providing easy separation of the cast upon completion of the cutting. In one variation the cutter could also shear the soft underlying wrapping through the use of increased torque combined with insertion of the cutter blade or serrations into an aperture within the foot that is traversing beneath the hard cast cover and underlying soft wrapping on a parallel path to the cutter mechanism.

Any combination of various cutting designs and thickness of the cutter and advancement mechanisms could be incorporated within the cutter itself to utilize the mechanical advantages of the low speed, high torque design. One embodiment might utilize two or more single purpose cutters. These multiple cutters could transverse subsequently to each other. They might also advance side by side creating two or more pathways through the cast. For example, the lead cutter might only function as a gripper for advancement and for initial piercing and severing of the hard cast. A second cutter might then only function as a cutter of the soft wrapping. In one variation a third circular mechanism might be included to spread open the pathway to ease the separation of the cast parts upon a completed cut pathway.

In another variation the cutting mechanism might include two small cutters located above the foot below the hard cast cover that would be able to score the underside of the hard cover facilitating the ability of the elevated moveable foot to deform the cast creating a wider pathway.

Figure 1:
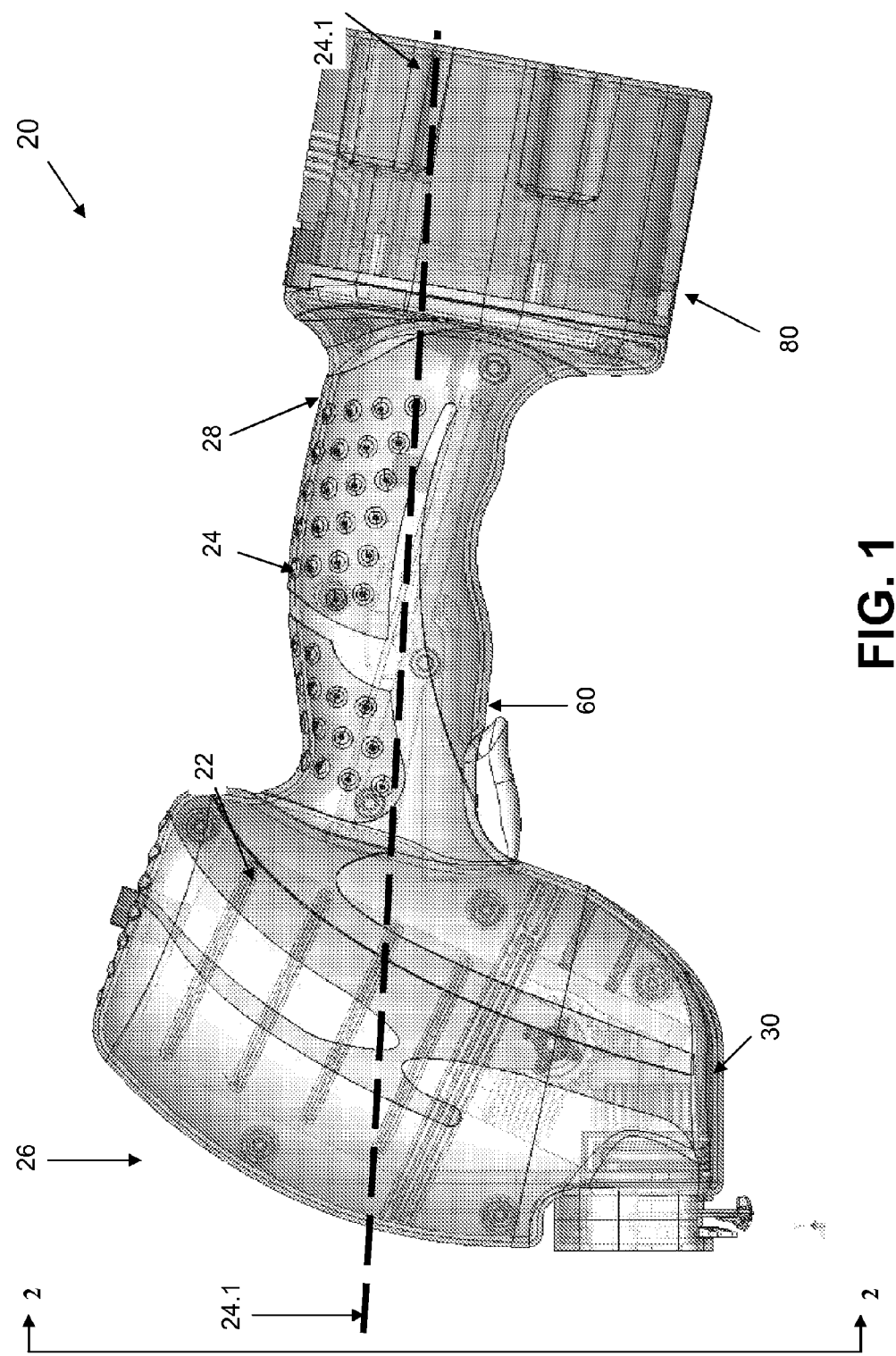
FIG. 1 is a side elevational view of a cast removal system according to one embodiment of the present invention. Various aspects of the figure are semi-transparent. Other aspects of the figure include modeling lines.
Figure 2:
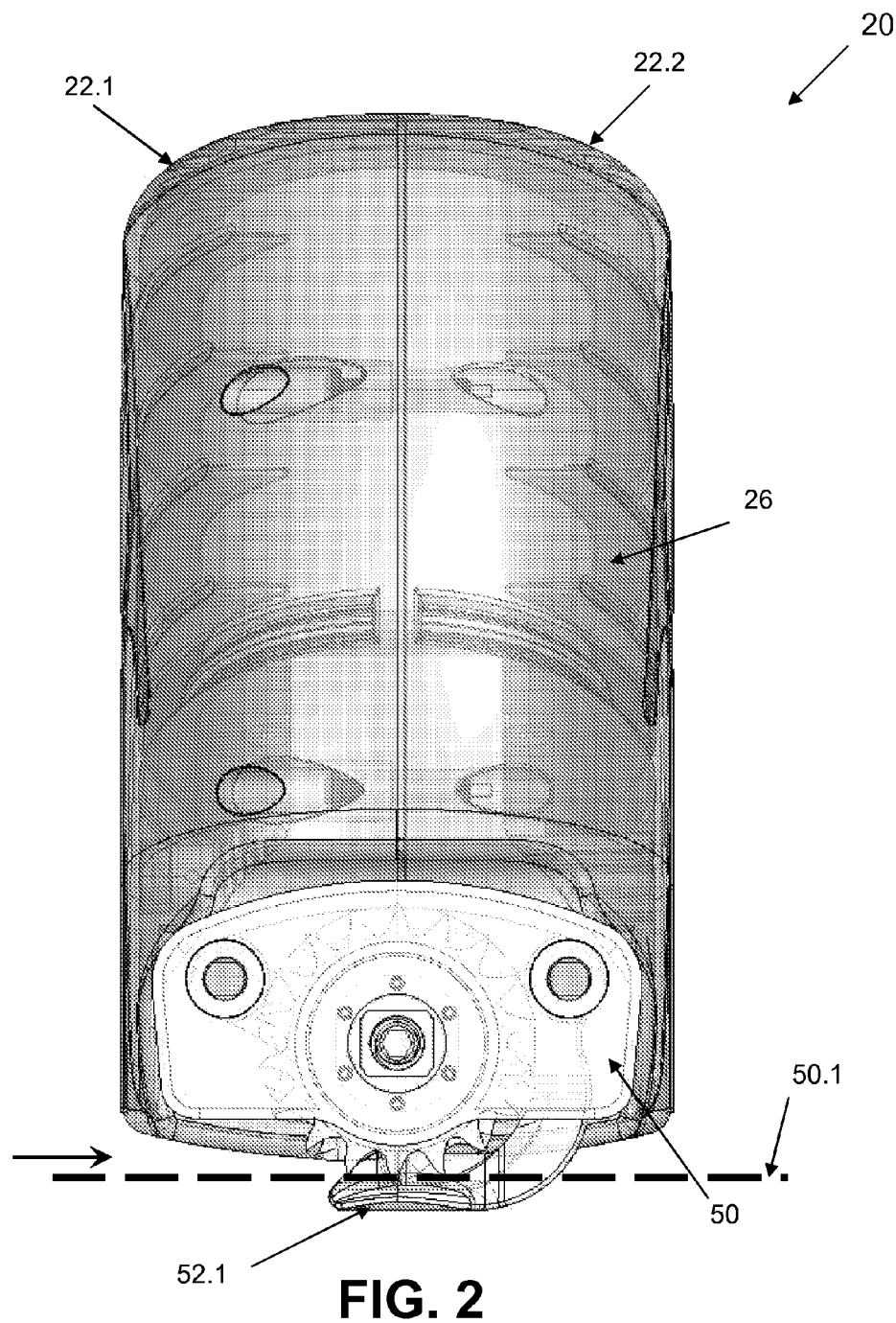
FIG. 2 is a front end view of the apparatus of FIG. 1 as taken along line 2-2 of FIG. 1.

FIGS. 1 and 2 show external views of an apparatus 20 according to one embodiment of the present invention. Apparatus 20 includes a mid-positioned handle 24 adapted and configured to be grasped by the hand of a human operator. One end of handle 24 includes a battery adapter 28 that couples to a battery assembly 80. The other end of handle 24 is attached to an enclosed motorized cutting assembly 30 housed within a motor enclosure 26. As seen best in FIG. 1, handle 24 preferably includes a plurality of rounded projections for improved gripping by the palm of the operator's hand. Further, handle 24 includes various curved surfaces that are adapted and configured for improved gripping by the fingers of the operator.

As best seen in FIG. 2, a cutting assembly 50 is mounted on the front end of apparatus 20. Cutting assembly 50 preferably splits, shears, and advances a layer of material along a path 50.1. Referring to FIG. 1, handle 24 preferably establishes a support axis 24.1 that is generally orthogonal to material path 50.1. The arrow along 50.1 indicates a cutting assembly 50 oriented for movement of material in the direction of the arrow. An operator holding apparatus 20 by handle 24 is ergonomically encouraged to move apparatus 20 from side to side (from the operator's right to left or left to right). In those embodiments relating to removal of a cast from a limb of a patient, the material path 50.1 is generally parallel to the length of the limb. The orientation of axis 24.1 and 50.1 therefore permits an operator such as a surgeon, paramedic, or other health care professional to comfortably stand alongside the cast of the patient. Further, cutting assembly 50 is preferably symmetrically coupled to apparatus 20, such that the direction along path 50.1 (from right to left or from left to right) can be changed by removing cutting assembly 50, turning it around, and reattaching it to the front end of apparatus 20.

Figure 3:
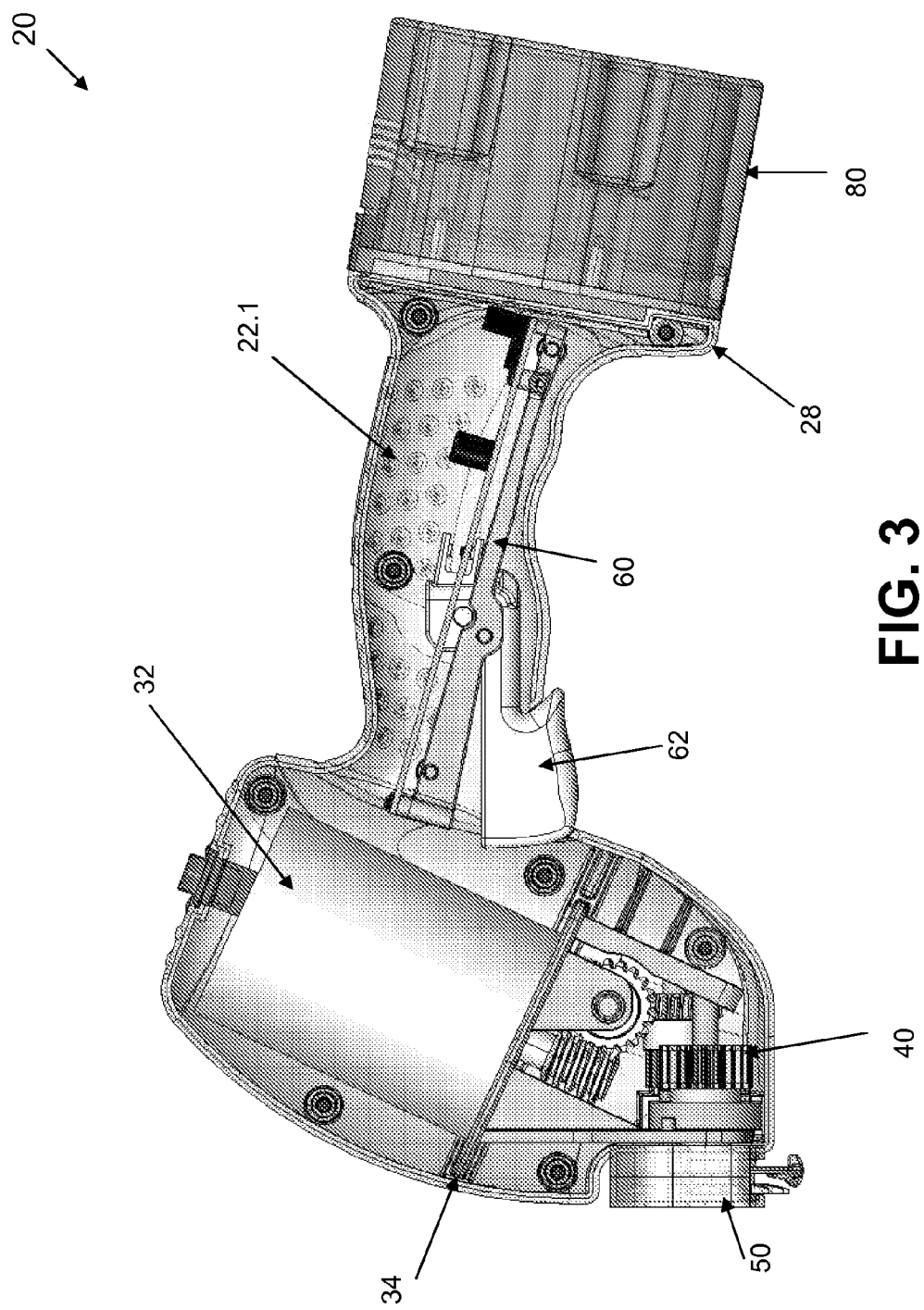
FIG. 3 is a view of the apparatus of FIG. 1 with one of the housing covers removed.
Figure 4:
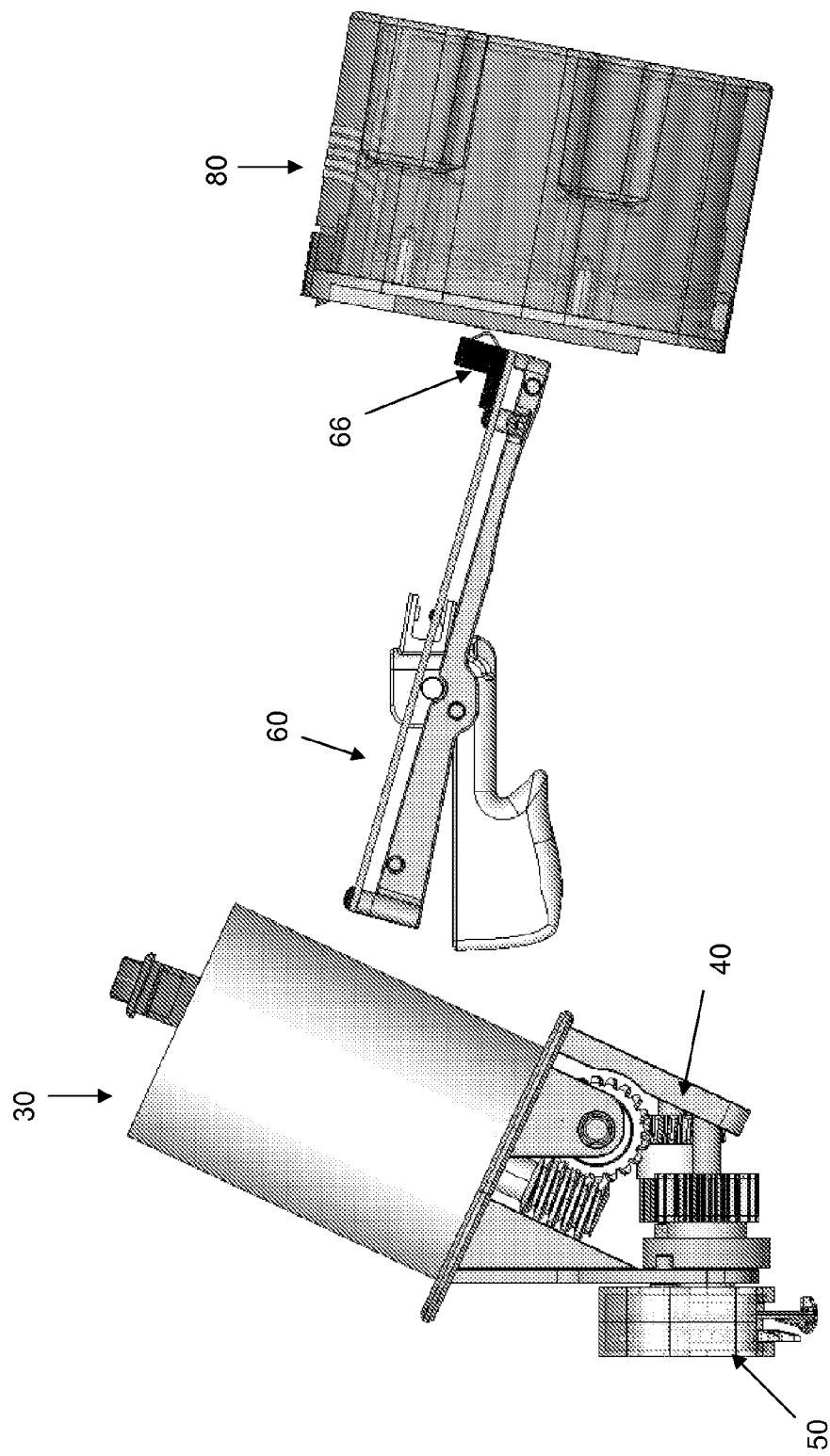
FIG. 4 is a view of the apparatus of FIG. 3 with the other housing cover removed.

FIGS. 3 and 4 show apparatus 20 with the right and left housing covers 22.1 and 22.2, respectively, removed. Cover 22.2 is removed in FIG. 3. Covers 22.1 and 22.3 are removed in FIG. 4. Apparatus 20 includes a motorized cutting assembly 30 comprising a motor 32, gear reduction 40, and cutting assembly 50 supported by handle 24 and located in or on enclosure 26. A handle assembly 60 is located within handle 24. A battery assembly 80 is supported on one end of handle 24. Handle assembly 60 and battery 80 are in electrical communication, and power from battery assembly 80 is provided through one or more electrical contacts 66. Additionally, handle assembly 66 is in electrical communication with motorized cutting assembly 30, and provides conditioned electrical power to motor 32.

It is understood that apparatus 20 is not constrained to the placement of components shown in FIGS. 3 and 4, nor is it constrained to the type of components shown in FIGS. 3 and 4. As one example, apparatus 20 does not require a battery assembly and other embodiments of the present invention contemplate the use of electrical power from a cord that plugs into a wall socket. Additionally, the splitting and shearing apparatus and methods described herein can be powered by means other than electric motor including operation based on hydraulic power or pneumatic power, as examples.

Figure 5:
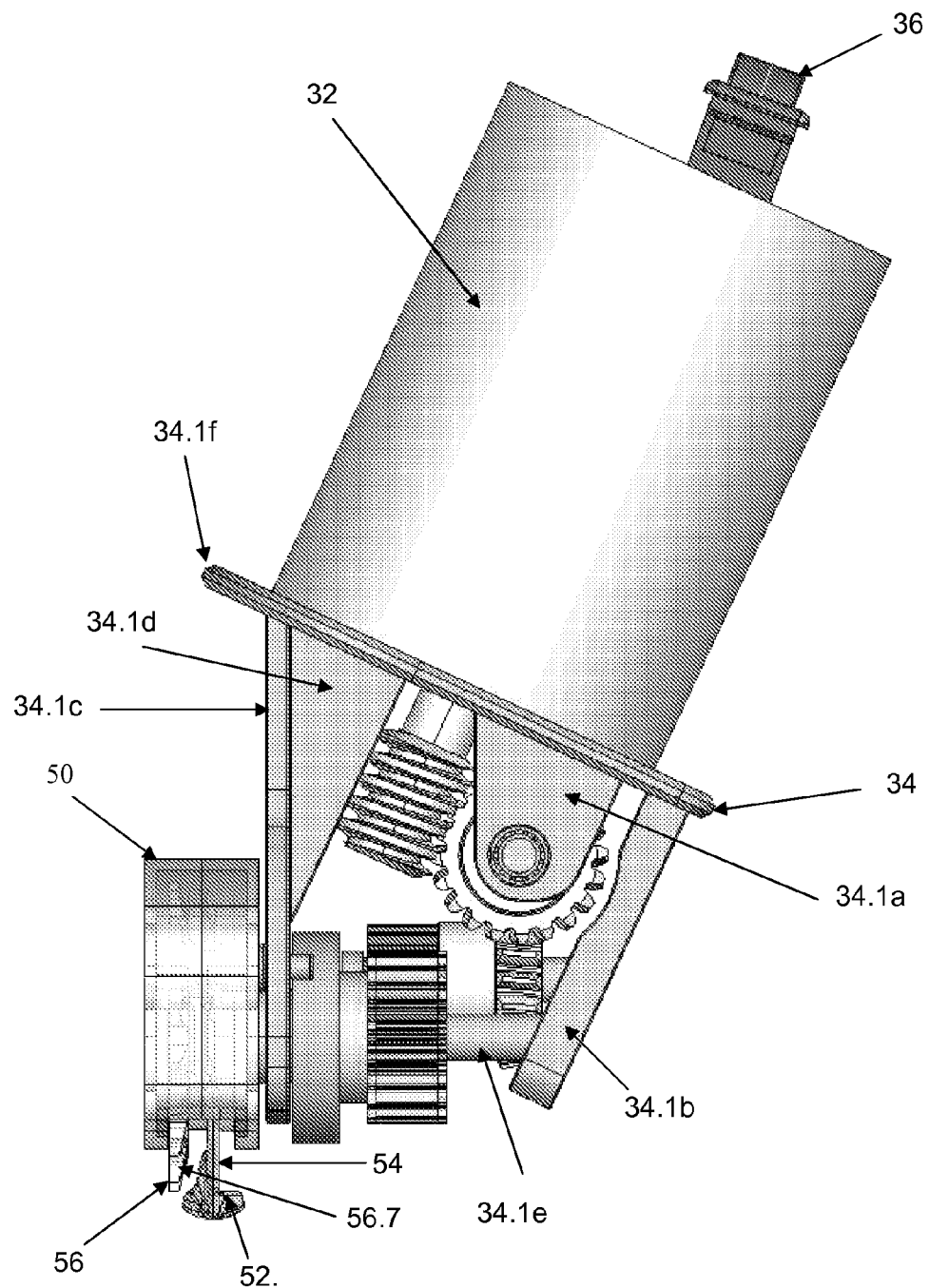
FIG. 5 is a view of a portion of the apparatus of FIG. 4.
Figure 6:
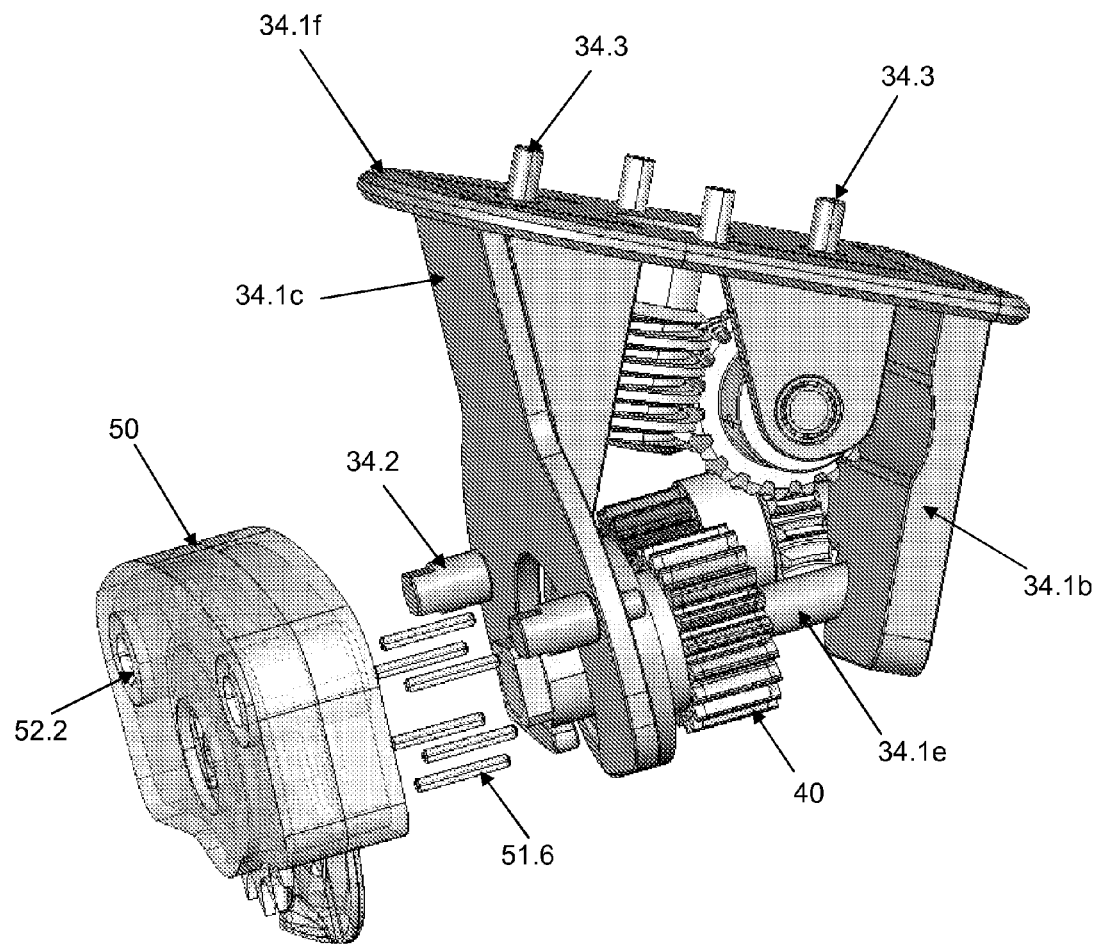
FIG. 6 is a left side, top, and semi-exploded perspective of a portion of the apparatus of FIG. 5.
Figure 6A:
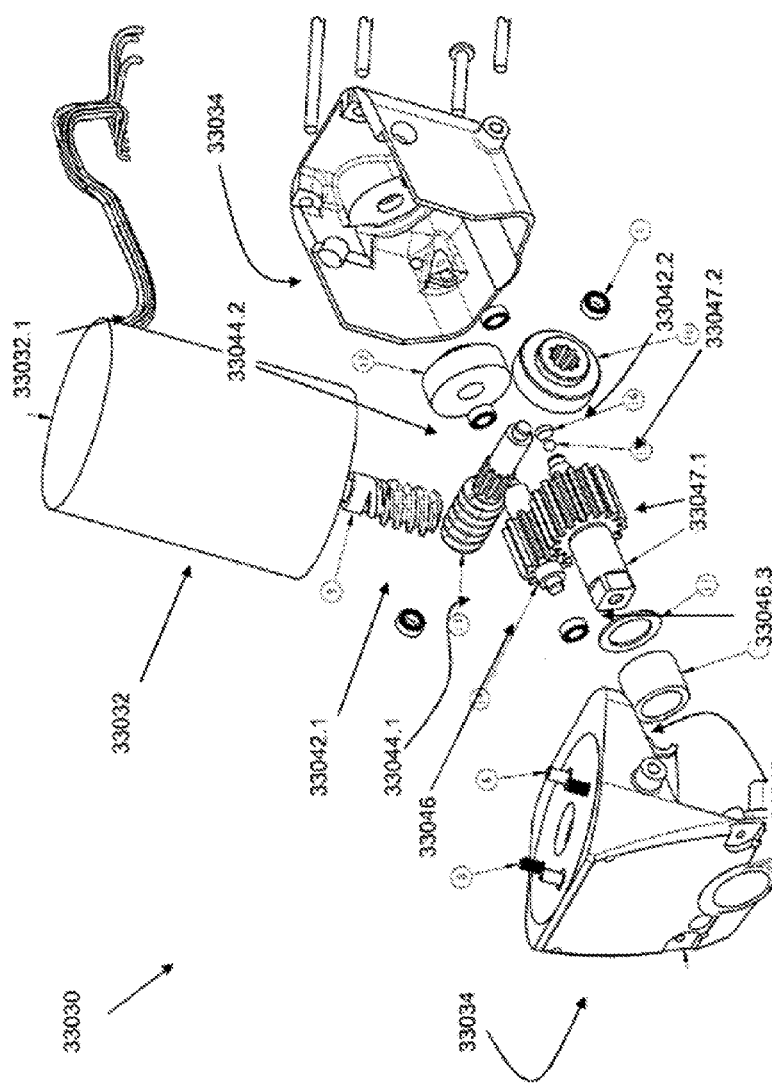
FIG. 6A is a left hand, top perspective, exploded view of a motorized cutting assembly according to another embodiment of the present invention.

FIGS. 5 and 6 show portions of motorized cutting assembly 30. Referring to FIG. 5, motorized cutting assembly 30 includes a motor 32, gear train assembly 40 and cutting assembly 50, all supported relative to each other by a support assembly 34. Briefly referring to FIG. 3, it can be seen that support assembly 34 is located within housing halves 22.1 and 22.2 by one or more channels, or in any other manner. In one embodiment, motor 32 is a brushless DC motor, such as a model DIH 23-30-013Z as fabricated by BEI Kimco Magnetics.

Referring again to FIGS. 5 and 6, support assembly 34 includes front and rear support members 34.1c and 34.1b. A pair of triangularly shaped webs 34.1d provide bracing for front plate 34.1c relative to central platform 34.1f. A pair of projecting ears 34.1a bearingly support a portion of gear reduction assembly 40. One or more stationary axles 34.1e are coupled to either front plate 34.1c or rear plate 34.1b to bearingly support portions of gear train 40. In some embodiments, the various components of support assembly 34 are fabricated from aluminum or steel, and welded together. In yet other embodiments, support assembly 34 is fabricated from a plastic material, and the individual components are welded together ultrasonically, or adhered together, as examples. In yet other embodiments, support 34 is a one piece or multi piece molding. The aforementioned methods of fabricating support 34 are provided as examples only.

Referring to FIG. 6, a plurality of dowel pins 34.3 extend from a face of central support member 34.1f, and align the driving axis of motor 32 with the input worm gear of gear train 40. The front face 34.1c of support 34 include a pair of locating dowels 34.2 that are received within corresponding dowel holes 52.2 to align cutting assembly 50 relative to gear train 40. Also shown in FIG. 6 are a plurality of alignment pins 51.6 that align together front adapter 51.41 and rear adapter 51.42, which are shown in FIG. 8, and which will be discussed later.

Preferably, apparatus 20 includes a switch 36 for changing the polarity of electrical power provided to motor 32. This change in polarity also changes the direction of rotation of motor 32, gear train 40, and cutting welds 56 and 54. This feature is useful in conjunction with the removal, swapping from end to end (such as about the vertical axis shown on FIG. 7), and reattachment of cutting assembly 50 so as to affect a change in the direction of material path (as previously referenced relative to FIG. 2).

FIG. 6.5 shows an exploded perspective view of a motorized cutting assembly 33030 according to another embodiment of the present invention. A brushless, DC motor 33032, having a wireloom 33032.1 providing output signals for motor sensors and further providing input power to power the motor, is coupled to a worm 33042.1 of first worm pair 33042. This first worm pair is coupled to a second worm pair 33044, which further drives a pinion set 33046. The output torque of gear train 33040 is provided at an output drive 33046.3 that is supported by a bearing 33047, which in one embodiment is a roller bearing. The output drive axis further includes a thrust ball 33047.1 and a thrust disc 33047.2 to provide an axial load on the output shaft. A pair of molded housings 33034, front and rear, provide support and enclosure for gear train 33040, as well a mounting surface for alignment and coupling of motor 33032.

Figure 7:
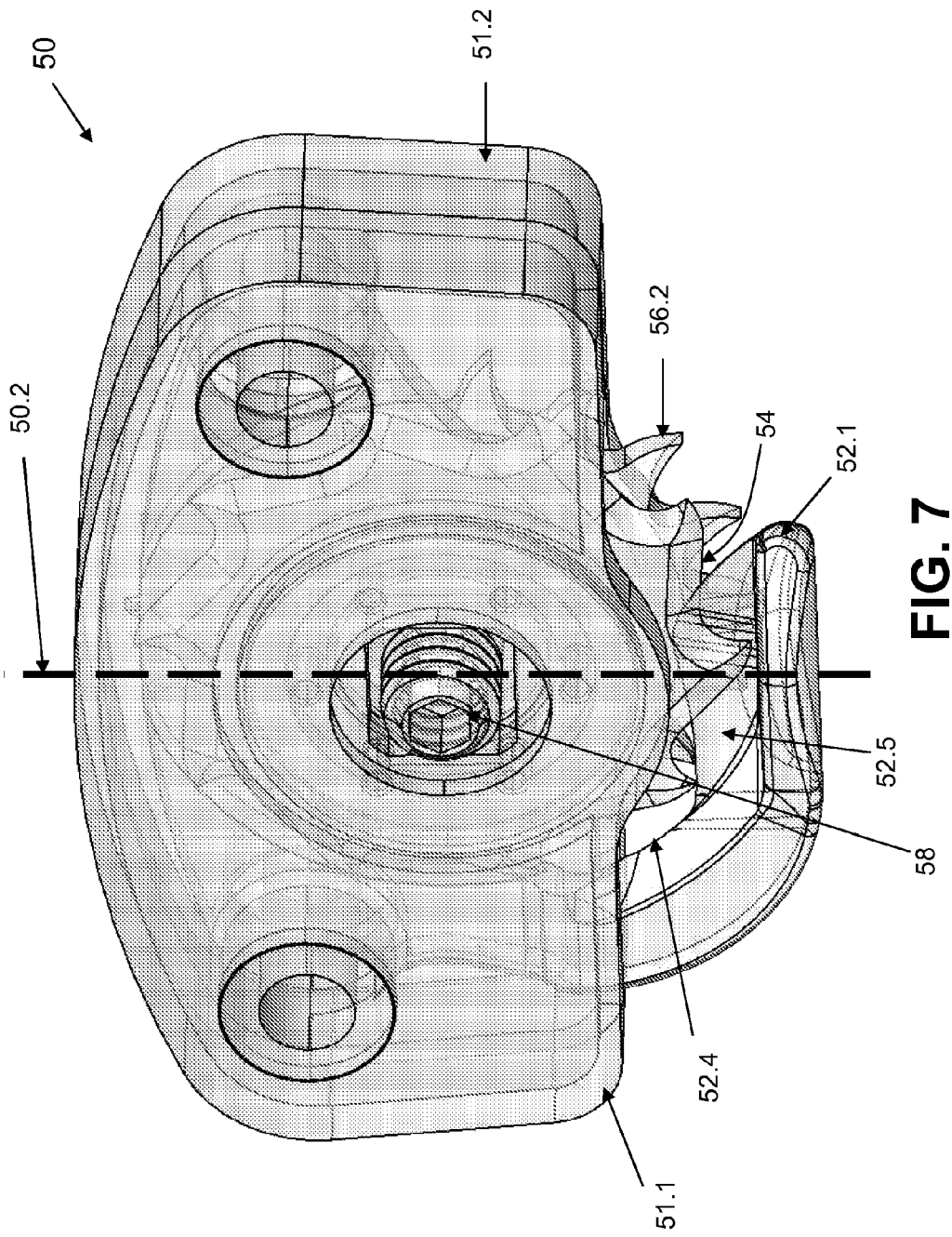
FIG. 7 is a left side and frontal perspective view of a portion of the apparatus of FIG. 6, with some components shown with modeling lines and/or semi-transparent.
Figure 8:
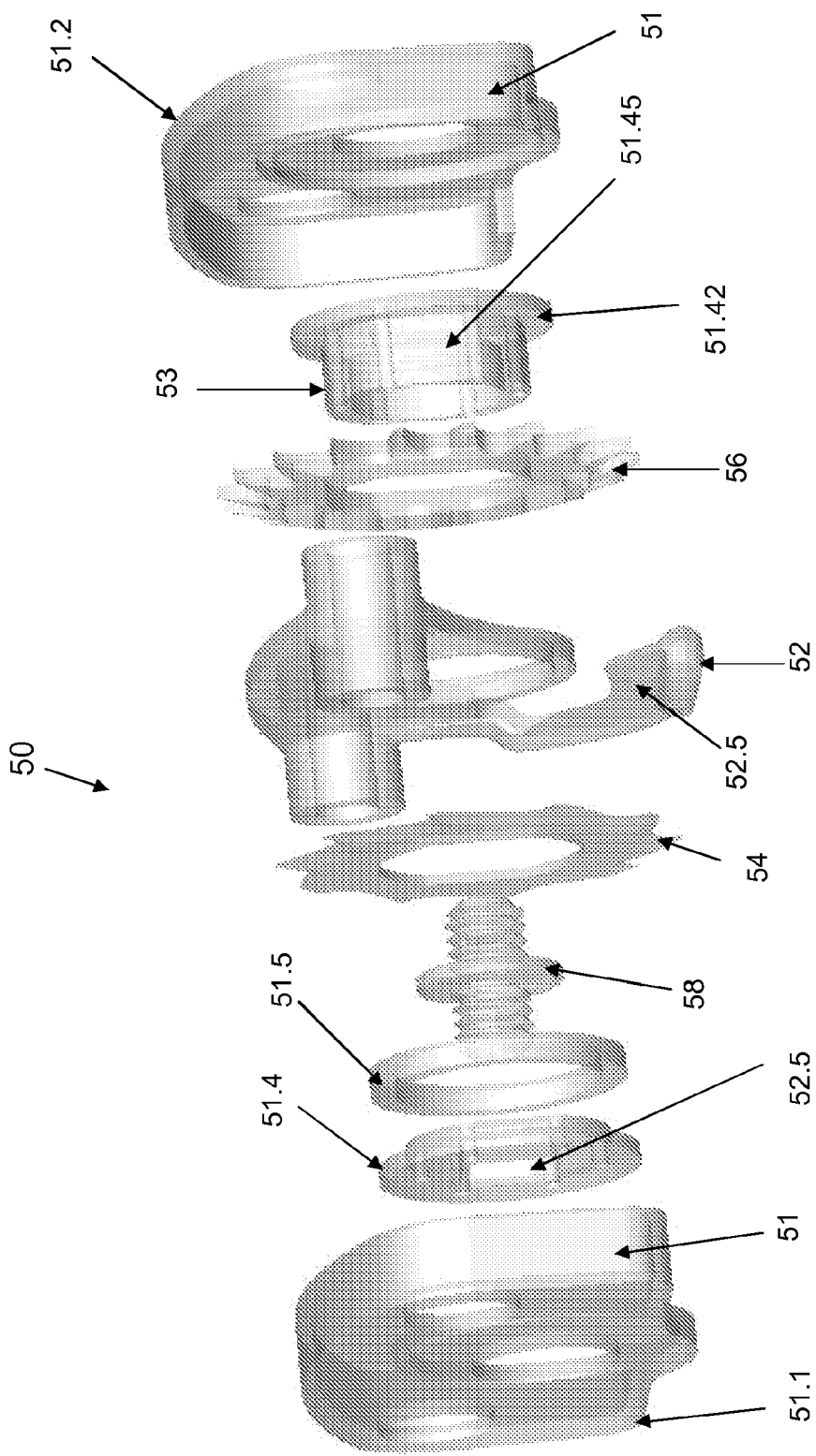
FIG. 8 is a frontal and left side exploded view of the apparatus of FIG. 7.

FIGS. 7 and 8 show assembled and exploded views, respectively, of cutting assembly 50. A housing 51 comprising front and rear halves 51.1 and 51.2, respectively, statically retain between them a keel 52. Housing 51 and keel 52 both include alignment holes to accept dowels 34.2.

Figure 13:
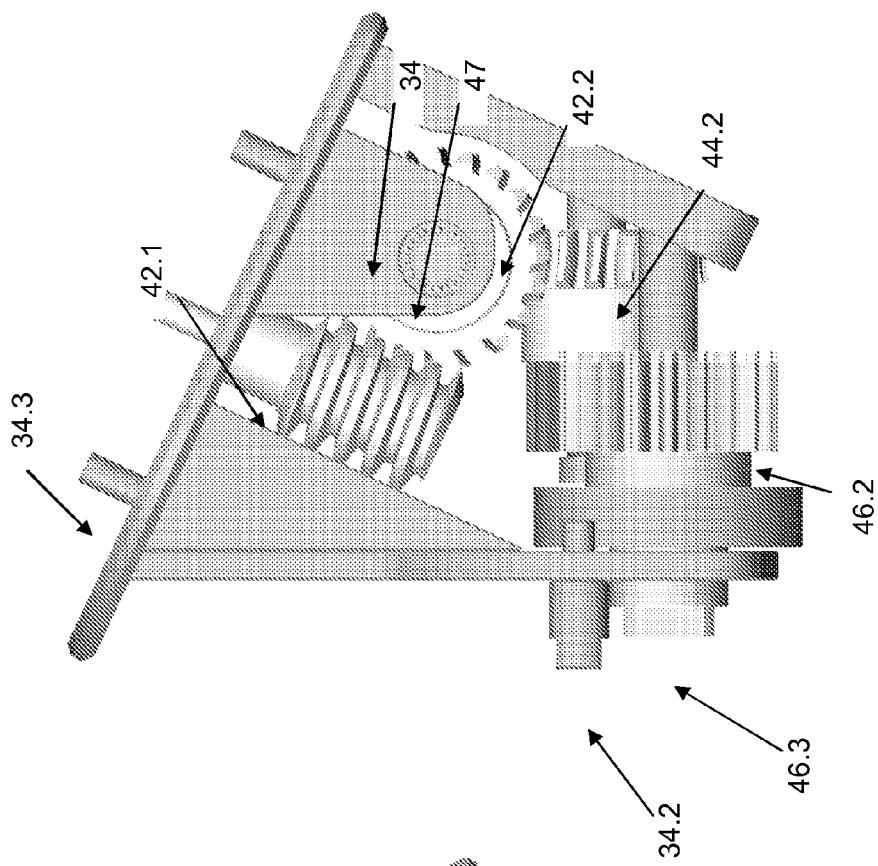
FIG. 13 is a left side elevational view of the apparatus of FIG. 12.
Figure 12:
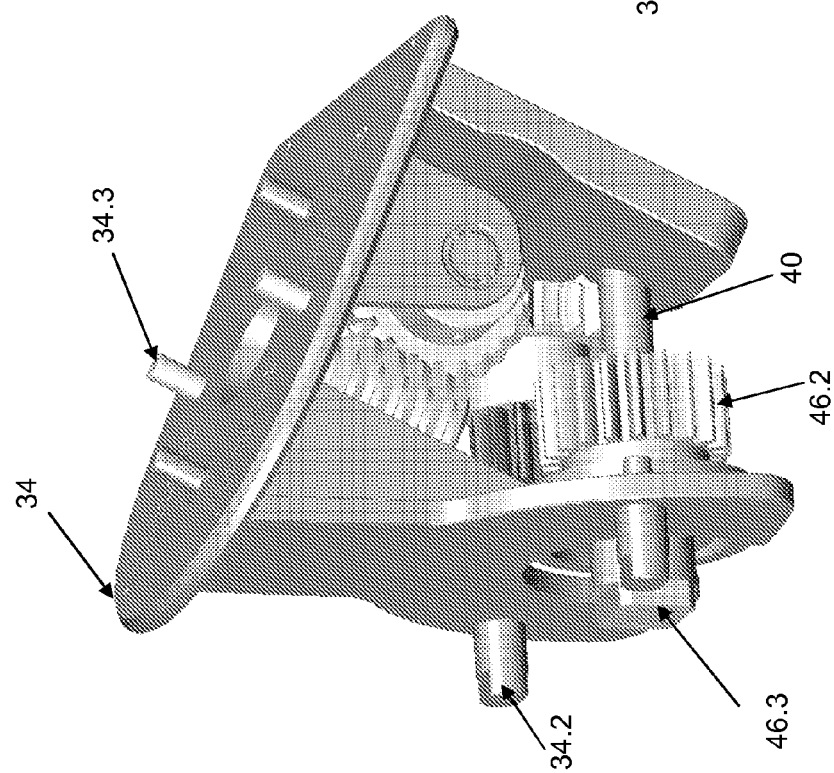
FIG. 12 is a left side, top, and frontal perspective of a portion of the apparatus of FIG. 6.

Further included within housing assembly 51 are front and rear driving adapters 51.4 aligned relative to each other by pins 51.6 previously seen in FIG. 6. Front adapter 51.41 and rear adapter 51.42 further include an interior driven interface 51.45 that have a shape complimentary to, and are driven by, adapter drive 46.3 of gear train 40 (which is shown in FIGS. 12 and 13).

Referring again to FIGS. 7 and 8, adapters 51.4 include (either individually, or together) a cutting assembly drive surface 53 that is complimentary in shape to, and drives, driven interfaces 54.1 and 56.1 of wheels 54 and 56 (as shown in FIGS. 9a and 9c).

Cutting assembly 50 further includes a socket screw 58 comprising a threaded shaft and a centrally located cylindrically-shaped central abutment. The abutment is captured within an internal pocket formed by the coupling of front adapter 51.41 to rear adapter 51.42. The threaded portion of socket screw 58 is received within a threaded receptacle 46.4 of adapter drive 46.3 (as best seen in reference to FIG. 12, the threaded receptacle not being shown in FIG. 12). A tightening of socket screw 58 into adapter drive 46.3 results in compression of the abutment feature of socket screw 58 against an inner wall of rear adapter 51.42. If the operator desires to change the direction of material flow as indicated along path 50.1 of FIG. 2, then socket screw 58 is loosened, and adapter drive 46.3 can be removed from driven interface 51.45. Cutting assembly 50 can then be rotated 180 degrees about the vertical axis shown in FIG. 7, and realigned with dowel holes 52.2. Socket screw 58, still captured but loose within the coupled adapters 51.41 and 51.42, is then tightened such that the central abutment feature now holds adapter 51.41 in compression against adapter drive 46.3.

Figure 10A:
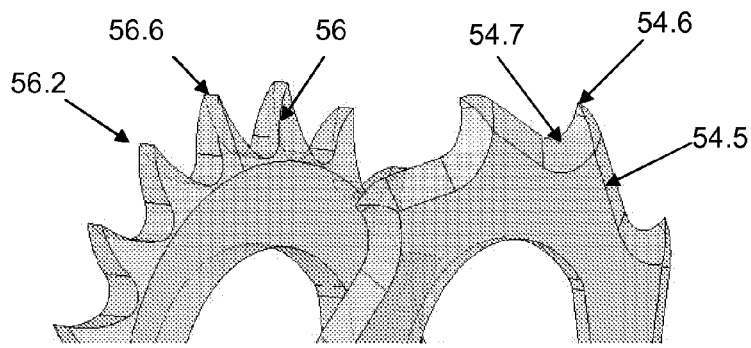
FIG. 10A is a perspective view of portions of the apparatus of FIG. 8.
Figure 10B:
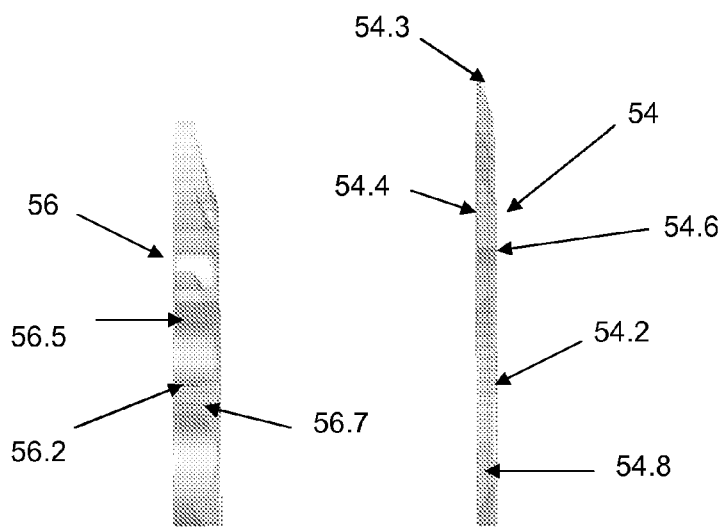
FIG. 10B is an end view of portions of the apparatus of FIG. 8.

Cutting assembly 50 further includes a means for biasing shearing wheel 54 toward contact with flat surface 52.5 of keel 52. In one embodiment, and as shown in FIG. 8, a wavy spring 51.5 is placed between a ledge of front adapter 51.41, and biases a part adapter drive 51.41 and surface 54.8 of splitting wheel 54 (referring to FIG. 10b). This biasing action places a load along the rotational axis of wheel 54 so that flat surface 54.4 of wheel 54 is in sliding contact with flat surface 52.5 of keel 52. As best seen in FIGS. 10A and 10B, wheel 54 has a sharp-edged perimeter 54.3 that extends around flat surface 54.4.

Figure 10C:
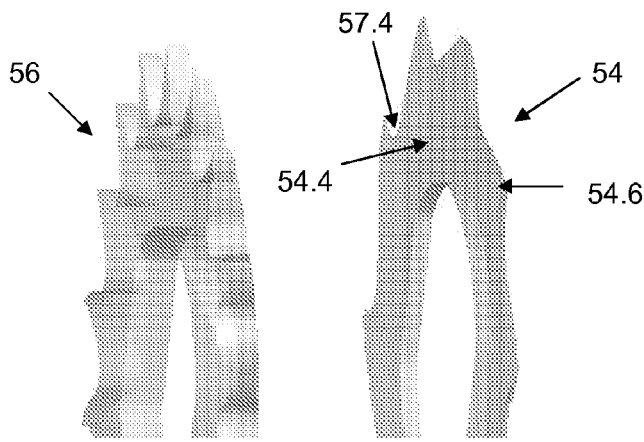
FIG. 10C is a perspective view of portions of the apparatus of FIG. 8, on the opposite side of the respective components relative to FIG. 8.

FIGS. 9, 10, and 11 show various views of the splitting or shearing wheel 54, the advancing wheel 56, and keel 52. The splitting wheel 54 is shown in FIGS. 9A, 10A, 10B, and 10C. Wheel 54 includes a plurality of shearing or splitting sectors 54.2 arranged in a generally cylindrical pattern. Preferably, there are anywhere from about 4 to about 14 sectors equally spaced around the periphery of the wheel. Each sector preferably includes a splitting edge 54.5 which, for the embodiment shown in FIG. 9A, is preferably linear. The beginning of the shearing sector includes a concave transitional section 54.7 that begins (taking into account the direction of rotation shown on FIG. 9A) with a lead in portion that extends radially inward toward the center of the wheel 54. Transitional section 54.7 then curves from the radially inward direction to alignment with splitting edge 54.5. Edge 54.5 is canted aft an outward angle relative to its tangency with the end of transitional section 54.7. Splitting edge 54.5 thereby has a component of motion (when wheel 54 is rotating) that is generally radially outward from the center of wheel 54. Each splitting sector 54.2 is closed out with a section 54.8 that transitions from a point of tangency with the end of splitting sector 54.5 toward a tip or apex 54.6. From apex 54.6, the next splitting sector 54.2 begins with the concave transitional portion 54.7. Wheel 54 further includes a driven interface 54.1 for rotating wheel 54 and transmitting the torque required to shear the layer of material. As best seen in FIGS. 10B and 10C, wheel 54 includes a substantially flat surface 54.4 that, during operation, slides against flat surface 52.5 of keel 52. The side of wheel 54 opposite of flat surface 54.4 has a surface adapted and configured to receive a biasing force from spring 51.5.

Advancing wheel 56 can be seen in FIGS. 9C, 10A, 10B, and 10C. Wheel 56 has a driven interface 56.1 adapted and configured to receive a rotational input and a torque input from an adapter 51.4. Wheel 56 includes a pattern of teeth 56.2 that are arranged in a generally cylindrical pattern about the center line of wheel 56. In one embodiments, each tooth includes a generally convex-shaped side 56.4 that meets a concave-shaped side at an apex or tip 56.6. As best seen in FIGS. 10A and 10B, each tooth in pattern 56.2 is asymmetrically shaped, as best seen in edge-on-view FIG. 10B. Each tooth 56.2 has a surface 56.7 that is spaced away from the keel (as best seen in FIGS. 1 and 5). The side 56.5 opposite of the keel side is substantially flat. Referring to FIG. 5, wheel 56 has teeth 56.2 that are axially spaced apart from the portion of the material being split. This axial spacing is adapted and configured to provide that each tip 56.6 is able to come into contact with portions of the material being cut that are not at the frayed or weakened split line of the material. However, other embodiments of the present invention contemplated advancing wheels having teeth that are symmetric, or biased toward the keel. However, some of these embodiments are adapted and configured to provide spacing between the split interface of the material and the portion of the material being contacted by advancing wheel 56, so that advancing wheel 56 is able to contact a portion of the material strong enough to advance the material.

In one embodiment, the tips 56.2 have sharp edges. Further, the axis of wheel 56 is located relative to the path of material along foot 52 such that the tips 56.2 press firmly against the surface of the material. In some embodiments, teeth 56.2 make indentations on the material as it is driven. In other embodiments, teeth 56.2 penetrate the top surface of the material. Further, yet other embodiments of the present invention contemplate the use of an advancing wheel 56 that relies on friction to advance material being cut. In one such embodiment, wheel 56 includes a rubber coated periphery that comes into frictional contact with the surface of the material. In yet other embodiments, the periphery of wheel 56 has a plurality of ridges which improves the frictional contact by establishing a frictional contact patch that is a narrow contact line.

Keel 52 can be seen in FIGS. 9b, 11a and 11b. Keel 52 includes a pair of dowel holes 52.2, each on an opposite side of a central clearance hole 52.7. Adapters 51.4 extend through clearance hall 52.7 to drive wheels 54 and 56. A central structural web extends in between each dowel hole 52.2 and central passage 52.7. Also extending from this central structural web is an arm 52.3 that extends downward toward the material path, and further supports a foot 52.1 adapted and configured to be located under the material path. As best seen in FIG. 11a, arm 52.3 jogs to the right (as shown in FIG. 11a). This offsetting jog permits arm 52.3 to have on it a sharp edge 52.4 that performs any final shearing of fibers not otherwise sheared or split by wheel 54.

Foot 52.1 has a substantially rounded and smoothed underside so as to not cause abrasions when this underside passes over a patient's skin, for those embodiments in which apparatus 20 is used as a cast removal device. The present invention also contemplates those embodiments in which an inventive apparatus is used to shear through paper, wood, sheet metal, or fabric, and in this embodiments the underside of foot 52.1 does not have to be rounded or curved.

As best seen in FIGS. 11a and 11b, a "shark fin" or flat surface 52.5 extends upwardly from the topside (material side) of foot 52.1. One side of this projection has a substantially flat surface 52.5 that is adapted and configured to be in sliding contact with wheel surface 54.4, and further to co-act with wheel 54 to split or shear the layer of material. In some embodiments, sharp edge 52.4 extends from arm 52.3 forward (opposite of the direction of the material flow) and along the upper edge of flat surface 52.5. However, in yet other embodiments, the top surface of flat surface 52.5 is not a sharp edge.

Referring to FIGS. 11*a* and 11*b*, dowel holes 52.1 have a length that is adapted and configured to provide rigidity and precision in the mounting of cutting assembly 50 to dowels 34.2.

FIGS. 11C to 11O depict various views of a cutting apparatus 31050 according to another embodiment of the present invention. Cutting assembly 31050 is similar to assembly 50, but with several changes. Assembly 31050 includes first and second advancing wheels 31056*a* and 31056*b*, preferably stationed on opposite sides of splitting wheel 31054. In addition, cutting assembly 31050 does not include a wavy spring for biasing the position of the splitting wheel. Further, each advancing wheel 31056*a* and 31056*b* incorporates apparatus similar in function to driving adaptors 51.4.

As best seen in FIGS. 11D and 11E, advancing wheels 31056*a* and 31056*b* are arranged on opposite sides of splitting wheel 31054 and further on opposite sides of arm 31052.3 of keel 31052. The teeth of each advancing wheel are preferably displaced outwardly from the plane in which the material is cut, as best seen in FIG. 11E. By spacing the ends of the advancing teeth away from the cut, there is less chance of the advancing teeth pressing against, and in some embodiments penetrating, the surface of the material too close to the frayed or weakened cut (split) edges of the material. However, the present invention is not so constrained, and further contemplates those embodiments in which the advancing teeth are roughly centered about a central plane of the corresponding advancing wheel, and also those embodiments in which the teeth are splayed inward toward the plane of the cut.

FIGS. 11F, 11G, and 11H depict various views of keel 31052. As seen best in FIG. 11F, the shearing face 31052.5 of keel 31052 has a multifaceted face. A lead-in portion 31052.5A is angled such that it falls away from the flat face 31054.4, with reference to the direction 31050.1 of motion. A second facet of the flat surface of foot 31052.5 falls further away from contact with wheel 31054, in an intermediate planar faceted section 31052.5B. The distal most portion of the shearing surface 31052.5 of foot 31052.1 is a third angled surface 31052.5C that falls away at an angle less steep than angles A or B. In one embodiment, the first faceted surface is angled three degrees falling away from the advancing wheel. The intermediate cutting facet falls away by about four degrees. The final planar facet C falls away at about one degree. In one embodiment, the angular orientation of portion 31052.5C helps create interference at the shearing interface to increase contact pressure between the face of the cutting wheel and the keel foot. The angular orientation of surface 31052.5A establishes an angle at which the cutting sectors meet the top surface of the foot, and helps to create improved shearing action relative to the soft casting materials (such as the woven materials).

FIGS. 11I, 11J, 11K, and 11L depict various views of a cutting wheel 31054 according to one embodiment of the present invention. Referring to FIG. 11L, a single cutting sector 31054.2 can be seen in detail. In one embodiment, each cutting sector begins (relative to the flow of material) from an apex 31054.6 for a short linear span of about three one-hundredths of an inch, and then blending tangentially into a transitional portion 31054.7 that is curved concave inwardly, and in some embodiments has radius of curvature of about one-tenth of an inch. This partly linear, partly curved transitional section 31054.7 tangentially blends into a substantially linear shearing section 31054.5 that, in one embodiment, is angled generally perpendicularly relative to the tip by less than about ninety degrees. The generally linear cutting section 31054.5 tangentially transitions to a curved close out section 31054.8 that is preferably curved concave outward, and ends in the tip 31054.6 of the next section.

FIGS. 11M, 11N and 11O depict various views of an advancing wheel 31056 according to another embodiment of the present invention. Wheel 31056 incorporates integrally a driving adaptor 31051.4. Wheel 31056 further incorporates a driven interface 31051.45 complementary in shape to a corresponding driving member 31046.3.

FIGS. 12, 13, 14, and 15 show various views of support assembly 34 and gear reduction assembly 40. Gear reduction assembly includes a first worm drive 42 that drives a second worm drive 44. Speed and torque from the output of second worm drive 44 is provided to a pinion pair 46, and finally to an adapter 51.4.

Figure 14:
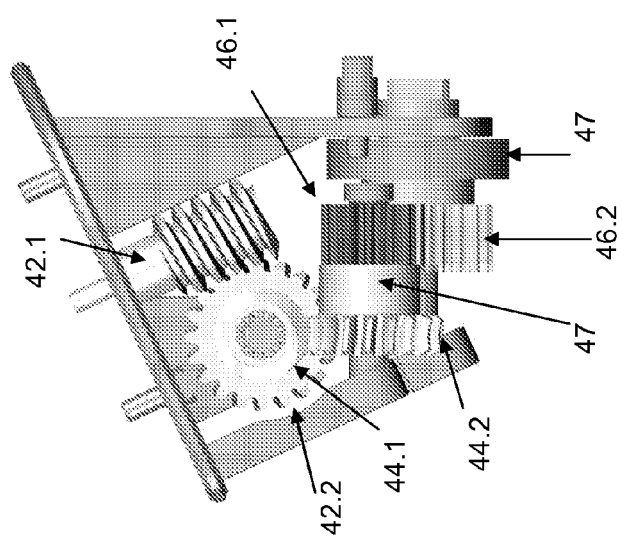
FIG. 14 is a right side elevational view of the apparatus of FIG. 12.

As seen in FIGS. 13 and 14, a rotational speed and torque from motor 32 is provided to a first worm gear 42.1. Worm gear 42.1 is in engagement with the corresponding worm wheel 42.2, the latter supported by support 34. In one embodiment, worm gear 42.1 is preferably fabricated from a first, harder material, and in one particular embodiment is fabricated from steel of the grade SAE 1144. In that embodiment, the worm 42.1 has an axial pitch of 0.133; has 2 threads; is a right hand helix with a lead angle of 10.9 degrees; a pitch diameter of 0.44 inches; a major diameter of 0.53; a minor diameter of 0.36 (all diameters in inches); and a pressure angle of about 20 degrees. The driven worm wheel 42.2 is preferably fabricated from a second material that is not as hard as worm 42.1, and in one embodiment worm gear 42.2 is fabricated from a plastic material such as nylon 66. In one embodiment, worm wheel 42.2 has a diametral pitch of 23.57; a helix angle of 10.8 degrees; is a right hand helix; has a pitch diameter of about 0.89 inches; a major diameter of about 0.96 inches; a minor diameter of 0.79 inches; and a pressure angle of about 20 degrees. In one embodiment, worm gear 42.2 is coupled to its shaft by sliding splines.

Figure 15:
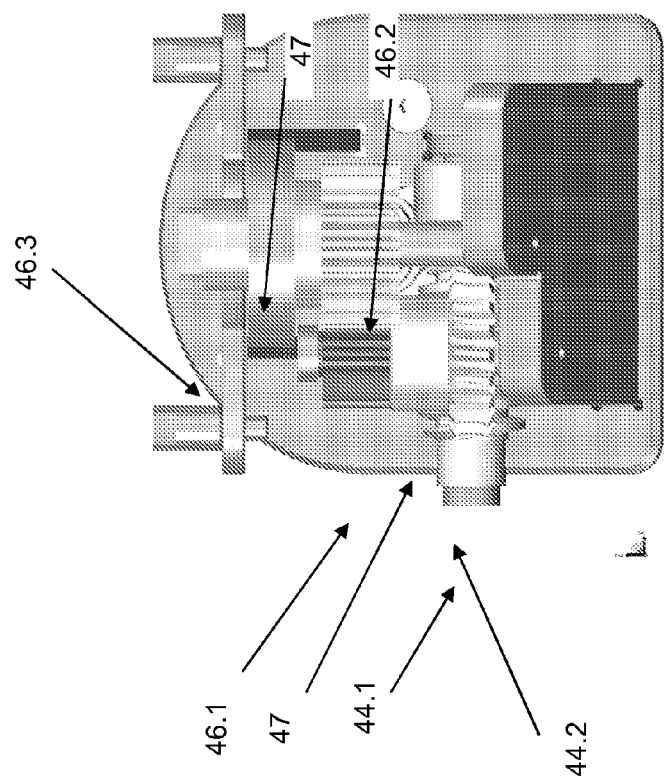
FIG. 15 is a bottom planar view of a portion of the apparatus of FIG. 12.

Referring now to FIGS. 14 and 15, located on the same shaft with worm wheel 42.2 is a second worm gear 44.1. Worm gear 44.1 engages a worm wheel 44.2. Worm wheel 42.2 is supported on a shaft along with a pinion drive gear 46.1 (with a bearing being placed in between these gears). In one embodiment, the second worm gear 44.1 is fabricated from a first, harder material, such as SAE 8620 and is case hardened in a specific embodiment, worm 44.1 has an axial pitch of about 0.16; has one thread; has a right hand helix; a helix angle of about 6.7 degrees; a pitch diameter of about 0.43; a major diameter of about 0.53; a minor diameter of 0.30; and a pressure angle of about 20 degrees. In one embodiment, the shaft that incorporates worm 44.2 includes a splined section to accept worm gear 42.2. Worm wheel 44.2 is preferably fabricated from a softer material than worm 44.1, and in one embodiment worm wheel 44.2 is fabricated from CA 673 bronze. In one specific embodiment, worm gear 44.2 has a diametral pitch of about 19.9; has 18 teeth; is a right handed helix; has a helix angle of about 6.7 degrees; a pitch diameter of about 0.91; a major diameter of about 0.98; a minor diameter of about 0.75; and a pressure angle of about 20 degrees.

Pinion drive gear 46.1 in turn drives a larger pinion driven gear 46.2, as best seen in FIGS. 12 and 15. The driven pinion member 46.2 is located on the same shaft with adapter drive 46.3, with a bearing 47 being interposed there between. In one embodiment, the overall gearing ratio from the output speed of the motor to the input speed of the motor to the output speed of drive 46.3 is about 330:1, such that gear train 40 has an output speed that is less than the input speed of motor 32, and is driven with an output torque that is greater than the input torque of motor 32.

Figure 16:
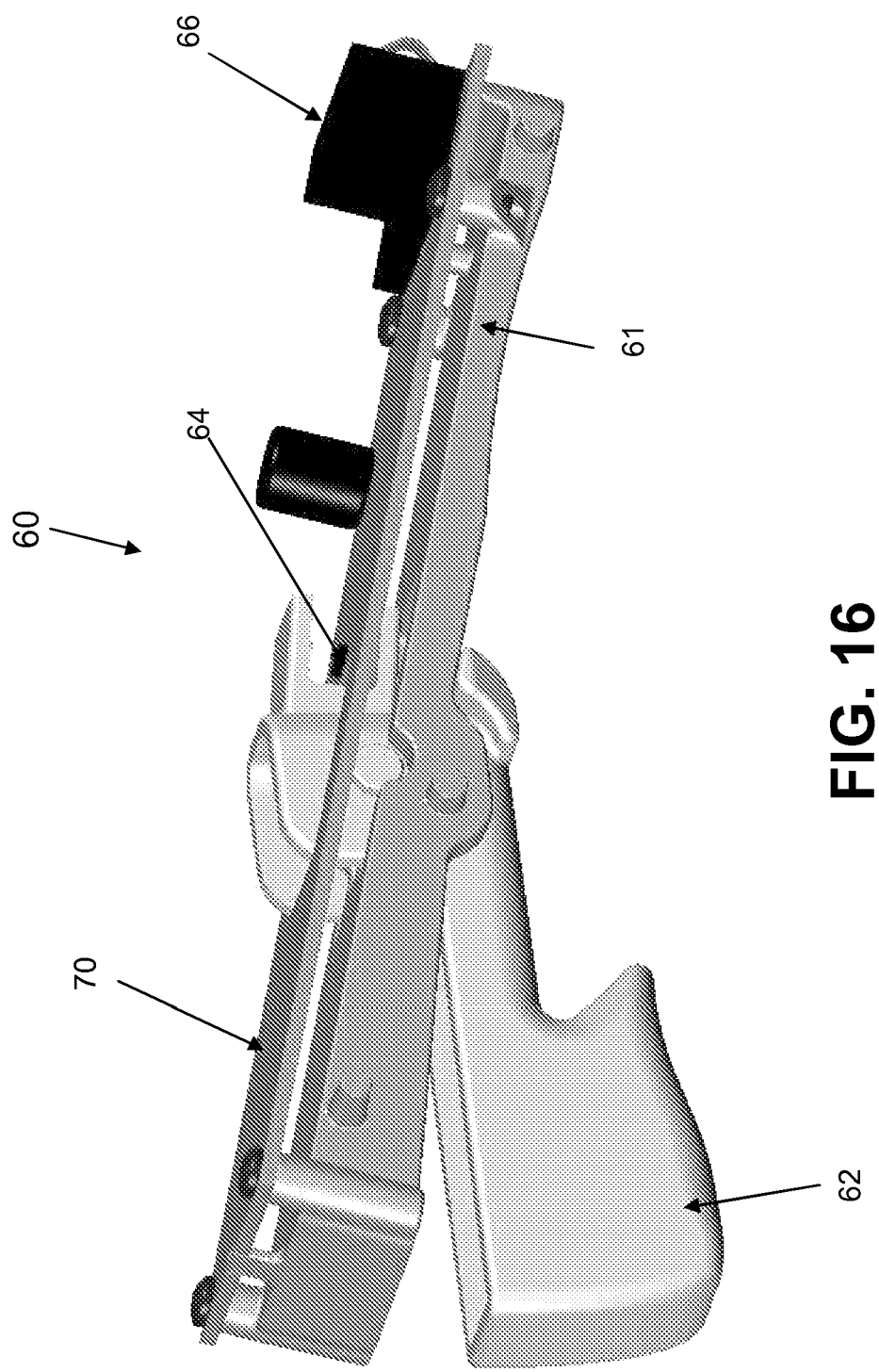
FIG. 16 is a left side and frontal perspective view of a portion of the apparatus of FIG. 4.

FIG. 16 is a prospective view of a handle assembly 60 according to one embodiment of the present invention. Handle 60 includes a structural chassis 61 that supports a pivotal finger switch 62. The interior end of finger switch 62 includes a pair of projections, each having on their surface a magnet. Located in between the magnets on these projections is a Hall sensor 64, located on a circuit card 70. A plurality of electrical contacts 66 located at one end of circuit card 70 provide an input for electrical power to circuit card 70.

Figure 18:
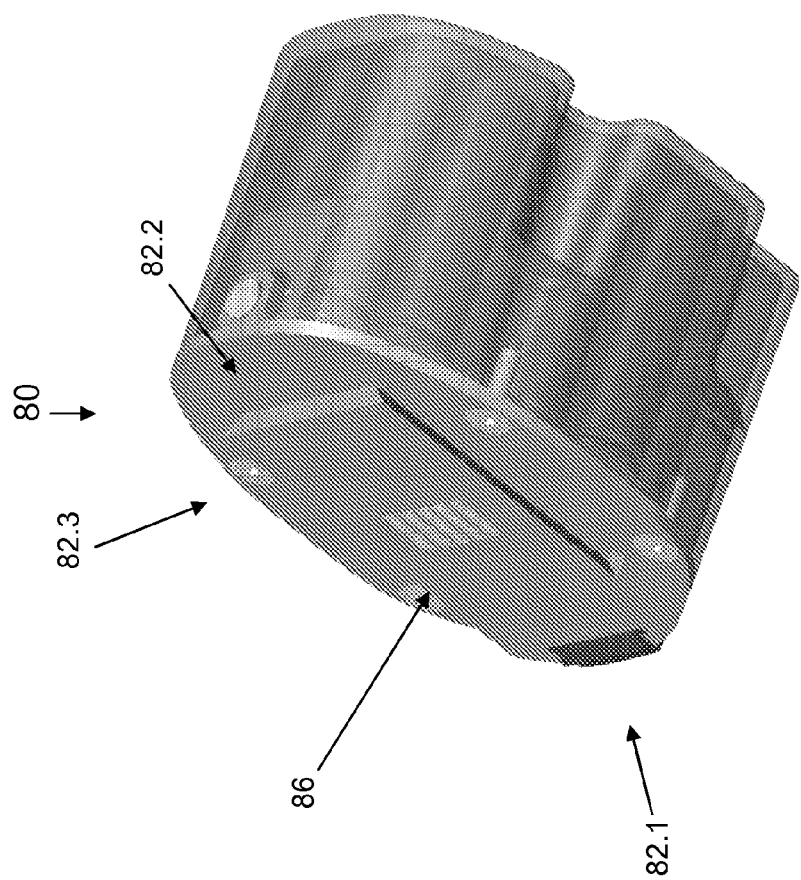
FIG. 18 is a right side and rear perspective view of the apparatus of FIG. 17.
Figure 17:
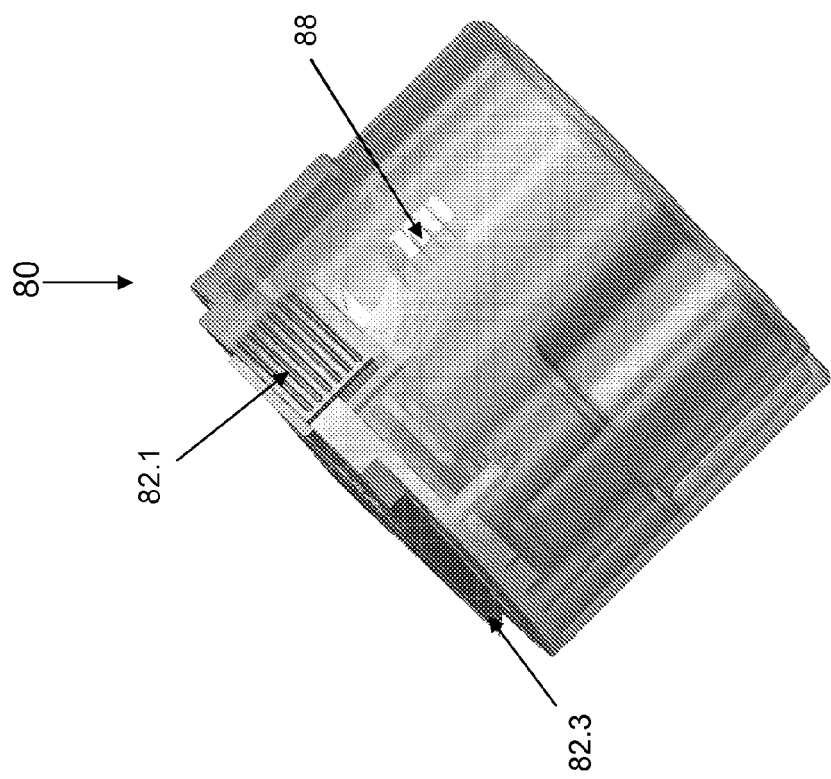
FIG. 17 is a left side and top perspective view of a portion of the apparatus of FIG. 4.
Figure 19:
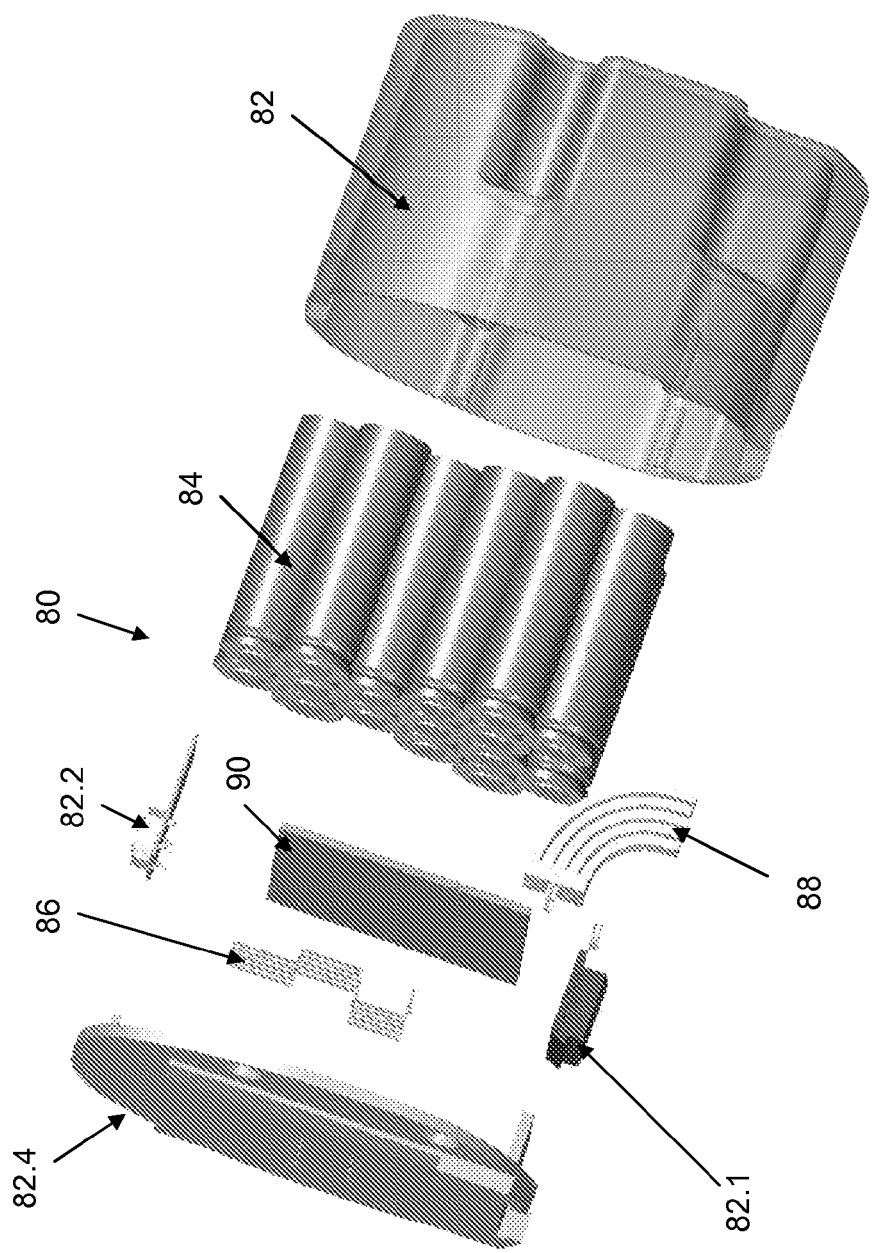
FIG. 19 is a left side exploded perspective view of the apparatus of FIG. 17.

FIGS. 17, 18, and 19 are various views of a battery assembly 80 according to one embodiment of the present invention. Battery assembly 80 includes a plurality of batteries 84 located within a housing 82. In one embodiment, the batteries are of a nickel-metal hydride type. Power from the batteries is provided to a circuit card 90 that conditions the power as required. A plurality of electrical contacts 86 provide battery power to contacts 66 of handle assembly 60. An assembly of five LEDs and corresponding light pipes 88 receive a signal from circuit card 90 pertaining to the state of charge of batteries 84. Referring to FIG. 17, the LEDs 88 indicate to the operator whether or not there is sufficient charge to sever the cast of another patient.

Cover 82.4 of housing 82 includes dovetail grooves 82.3 that are grasped by complimentary-shaped grooves on the underside of battery adapter 28. Battery assembly 80 further includes a spring-loaded sliding switch 82.1 that locks battery assembly 80 to handle 24. A button 82.2 provides an actuatable switch by which the operator can request the status of batteries 84 to be displayed on LEDs 88.

Figure 20A:
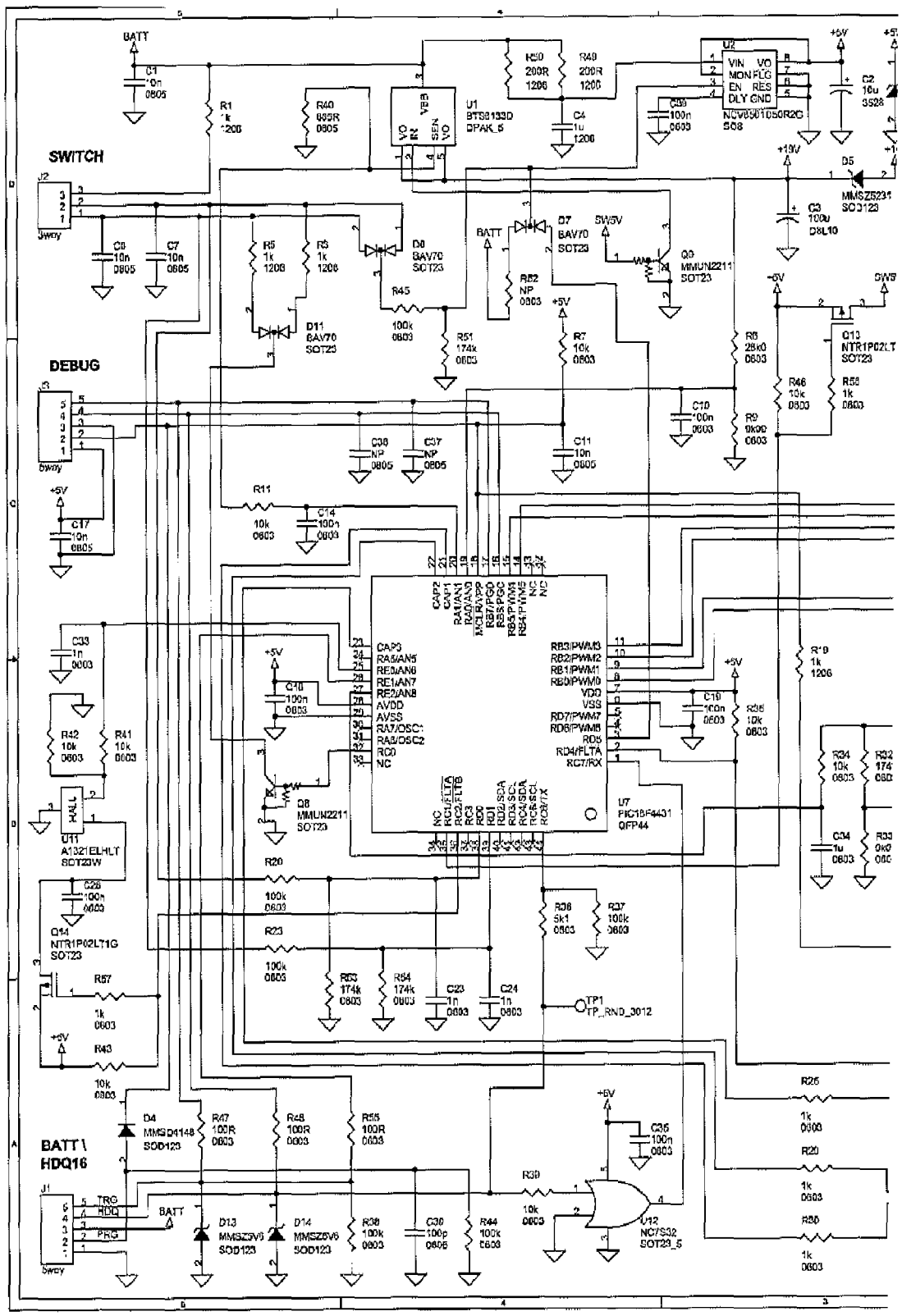
FIGS. 20A and 20B are complementary portions of a schematic diagram of a circuit that controls the operation of various embodiments of the present invention.
Figure 20B:
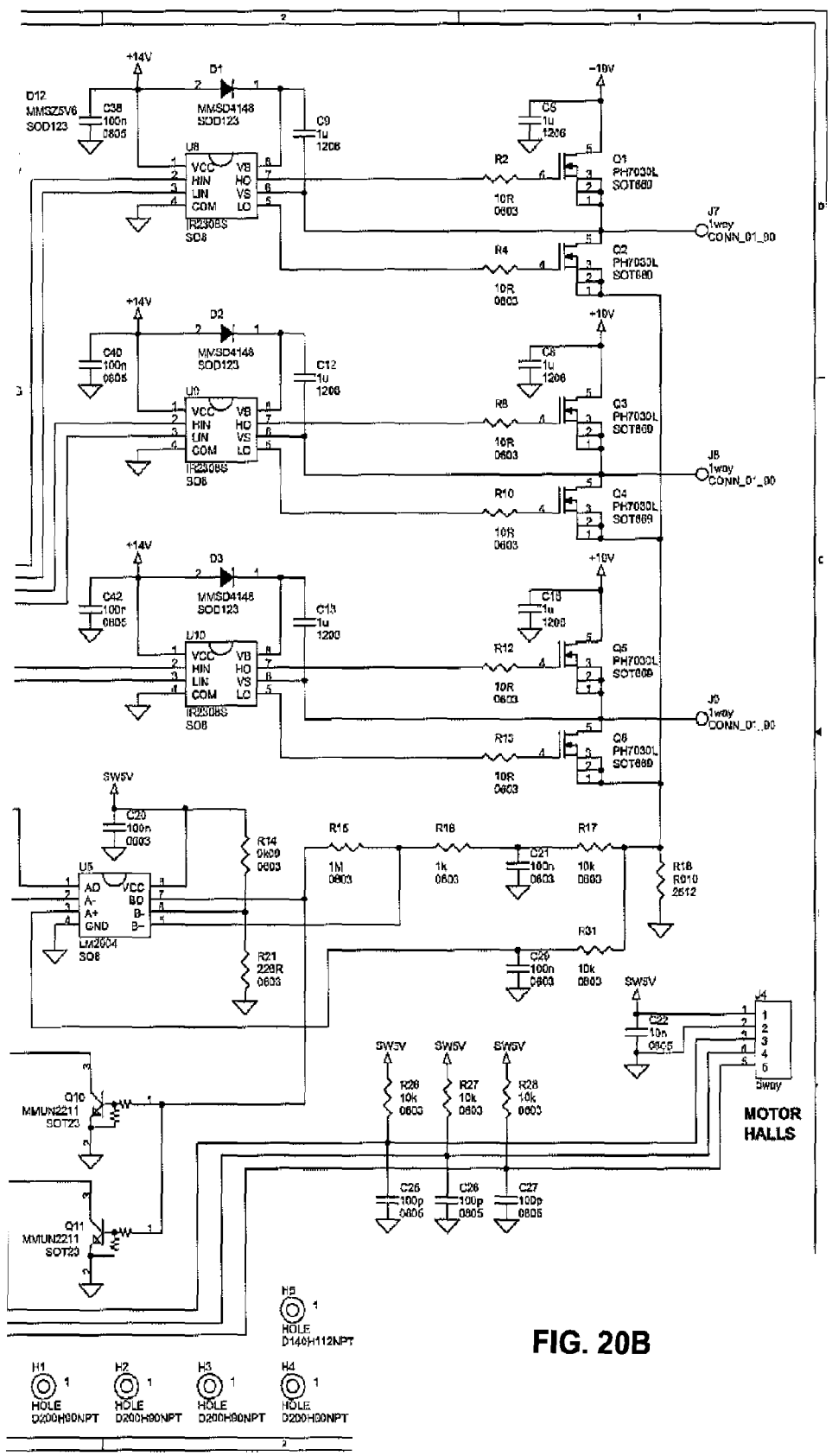

Turning to FIGS. 20A-20B, a circuit board for use in the illustrated embodiment is disclosed. Circuit card 70 embodies circuit 71 as illustrated in FIGS. 20A-20B. Hall effect sensor circuit 72 detects the position of finger switch 62 (see FIG. 16) and provides a signal encoding that position to controller IC 74. In the illustrated embodiment, sensor circuit 72 comprises an A1321ELHLT ratiometric linear Hall-effect sensor produced by Allegro MicroSystems. Controller 74 in this embodiment is a PIC18F4431 microcontroller by Microchip Technology Inc. Other sensors, feedback mechanisms, and controllers will occur to those skilled in the art in view of this disclosure. A memory (not shown) in communication with controller IC 74 is encoded with programming instructions executable by the controller to control the other components of apparatus 20 and implement the functionality of the device described herein.

Controller IC 74 in some embodiments is a microcontroller or general purpose microprocessor that reads its program from the memory. Controller IC 74 may be comprised of one or more components configured as a single unit. Alternatively, when of a multi-component form, controller IC 74 may have one or more components located remotely relative to the others. One or more components of controller IC 74 may be of the electronic variety including digital circuitry, analog circuitry, or both. In one embodiment, controller IC 74 is of a conventional, integrated circuit microprocessor arrangement, such as one or more CORE 2 QUAD processors from INTEL Corporation of 2200 Mission College Boulevard, Santa Clara, Calif. 95052, USA, or ATHLON or PHENOM processors from Advanced Micro Devices, One AMD Place, Sunnyvale, Calif. 94088, USA. In alternative embodiments, one or more application-specific integrated circuits (ASICs), general-purpose microprocessors, programmable logic arrays, or other devices may be used alone or in combination as will occur to those skilled in the art.

Likewise, in various embodiments, the memory includes one or more types such as solid-state electronic memory, magnetic memory, or optical memory, just to name a few. By way of non-limiting example, the memory can include solid-state electronic Random Access Memory (RAM), Sequentially Accessible Memory (SAM) (such as the First-In, First-Out (FIFO) variety or the Last-In First-Out (LIFO) variety), Programmable Read-Only Memory (PROM), Electrically Programmable Read-Only Memory (EPROM), or Electrically Erasable Programmable Read-Only Memory (EEPROM); an optical disc memory (such as a recordable, rewritable, or read-only DVD or CD-ROM); a magnetically encoded hard drive, floppy disk, tape, or cartridge medium; or a plurality and/or combination of these memory types. Also, in various embodiments, the memory is volatile, nonvolatile, or a hybrid combination of volatile and nonvolatile varieties.

Figure 21:
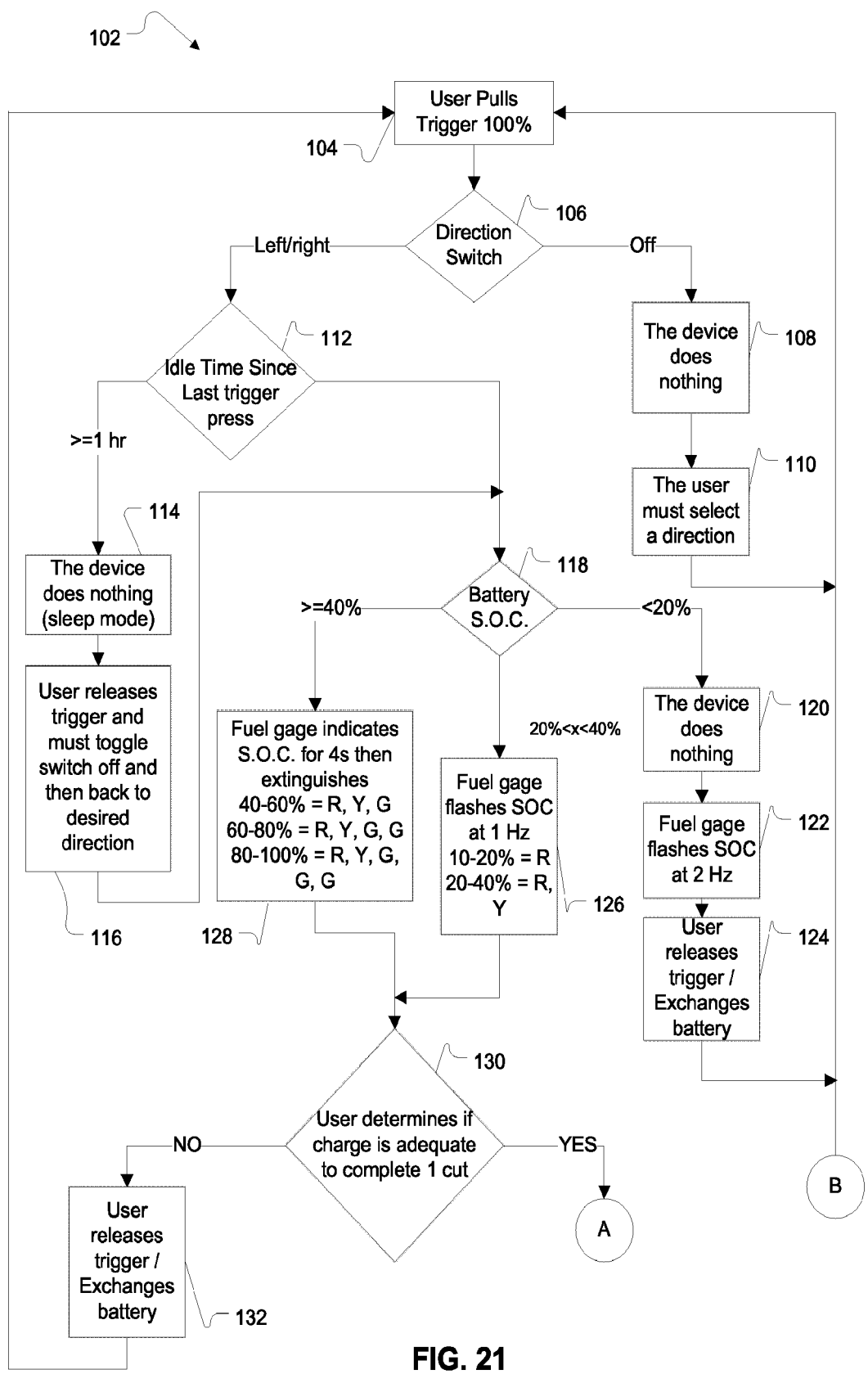
FIGS. 21-22 are a flowchart describing cutting operation of the apparatus of FIG. 1.
Figure 22:
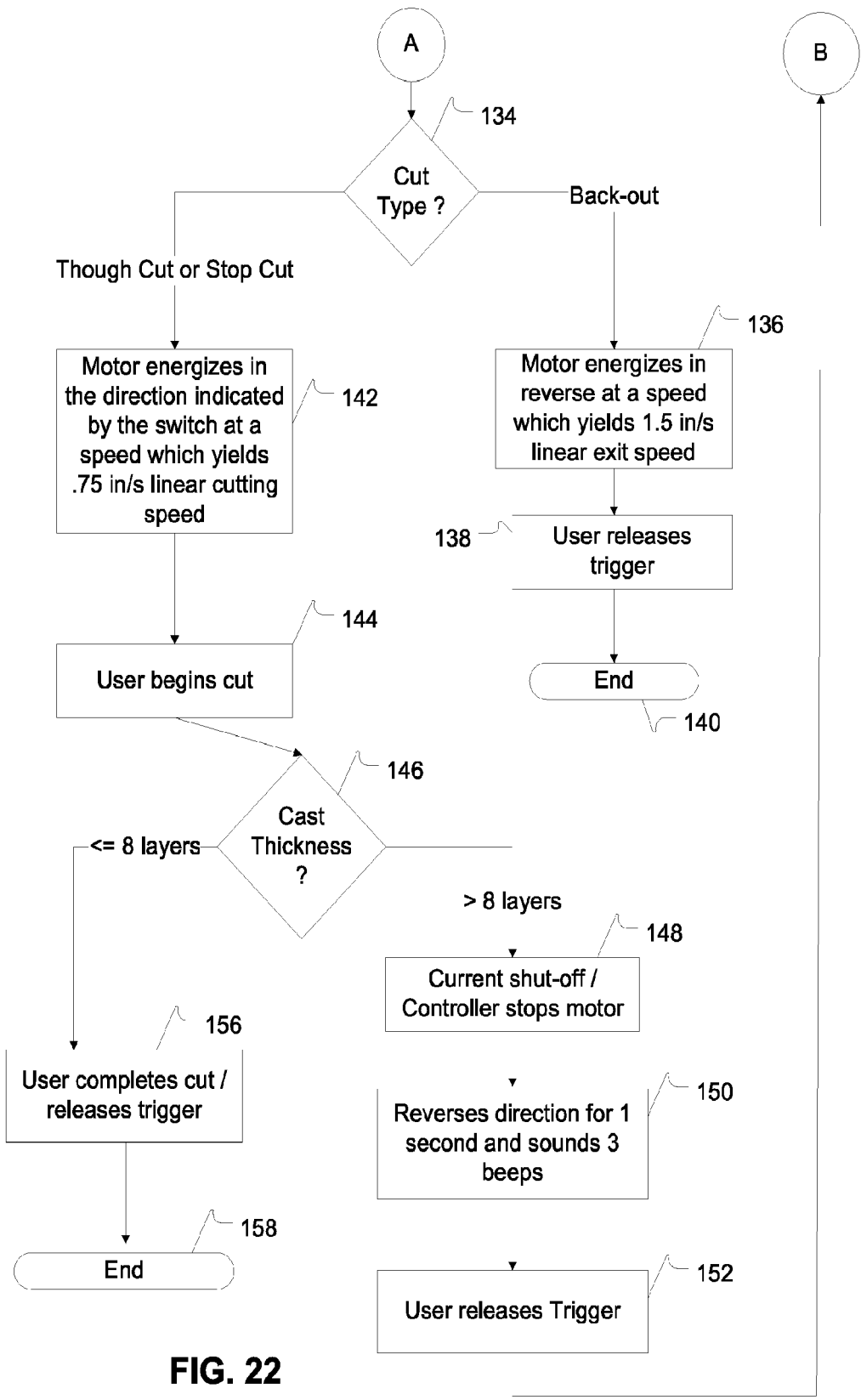

FIGS. 21-22 illustrate process 102, by which apparatus 20 operates during the cast-cutting process. To begin operation, the user pulls finger switch 62 (104). The system determines at decision point 106 whether the direction switch 36 (see FIG. 5) is in the off position. If so, the device does nothing (108) because the user must select a direction (110) before the device will operate. Control returns to wait for another finger-switch pulling event 104.

If the system determines at decision point 106 that the direction switch 36 is in the left or right position, then it calculates at decision point 112 whether the idle time since the finger switch press is greater than or less than a threshold period of time (in this embodiment, 5 minutes). If the idle time is greater than the threshold, then the device does nothing, staying in sleep mode (114). The user must release the finger switch 62 and move direction switch 36 to the "off" position, then back to the desired direction in order to resume operation (116).

Then, or if at decision point 112 the system determines that the time period since the last finger switch press is less than the threshold period, then the system determines the state of charge (SOC) of the battery at decision point 118. If the charge is less than or equal to a lower threshold (in this embodiment, 20% of the maximum charge), the motor does not engage (120) and the "fuel gauge" display 88 (see FIG. 17) flashes the lowest SOC indicator (122). The user must release the finger switch 62 and exchange the depleted battery for a charged one (124) before the system will resume operation with a fresh finger-switch pull event 104. Additionally, in this embodiment, once the battery SOC is lower than this lower threshold, the device 20 can only be used in reverse for one trigger press (to remove the device from a cut in progress, for example).

If the system determines at decision point 118 that the battery is charged between the lower threshold (here, 20%) and a middle threshold (in this embodiment, 40% of the maximum charge), then the "fuel gauge" display 88 flashes the SOC at 1 Hz (126). In this embodiment, if the charge is in the 0-20% range, the device does not operate, and the first (red) LED is flashed at 4 Hz, while if the charge is between 20-40%, the red and yellow lights are flashed at 1 Hz. Similarly, if the system determines at decision point 118 that the battery is charged to at least an upper threshold percentage of the maximum charge, the SOC is shown with a solid display of the charge level for four seconds (128). If the charge is in the 40-60% range, then the red light, the yellow light, and one green light are illuminated. If the charge is in the 60-80% range, then another green light is added. If the charge is in the 80-100% range, then all lights (red, yellow, green, green, green) in "fuel gauge" display 88 are illuminated. Regardless of the level of charge at step 128, the "fuel gauge" display 88 is illuminated for four seconds, then extinguished automatically.

After the fuel gauge level indication in step 126 or step 128, the user determines at decision point 130 whether the charge is adequate to complete the next cut. If not, the user releases the finger switch 62 and exchanges the battery (132), and the system waits for another finger-switch-pull event 104.

If the user determines at decision point 130 that enough charge remains to complete the next cutting operation, the system determines at decision point 134 whether the cut type is, on one hand, a "through cut" or "stop cut" or, on the other hand, a "back-out" operation. In some embodiments, this decision is made according to the flowchart in FIG. 26 and the accompanying discussion, while other embodiments use alternative methods and logic that will occur to those skilled in the art.

If the system determines at decision point 134 that reverse action is appropriate, then the motor 32 energizes in reverse at a speed that results in a 1.5 inch/second linear movement (136). When the cut is complete, the user releases finger switch 62 (138), and method 102 ends (140).

If the system determines at decision point 134 that it should be performing a "through cut" or "stop cut," then the motor 32 energizes in the direction indicated by the rocker switch 36 at a speed that yields a 0.75 inch/second linear cutting speed (142), and the user begins the cutting of the cast (144). At decision point 146, the system determines whether the material being cut is apparently greater than eight layers. If so, the current is shut off (148), the system reverses direction for one second and alerts the user with three audible beeps (150), and the user releases the finger switch 62 (152). Process 142 returns to wait for another finger-switch-pull event 104.

If at decision point 146 the system determines that the cast thickness is no greater than a threshold thickness (in this embodiment, eight layers), then the user completes the cut and releases the finger switch 62 (156), and the process ends (158).

Figure 23:
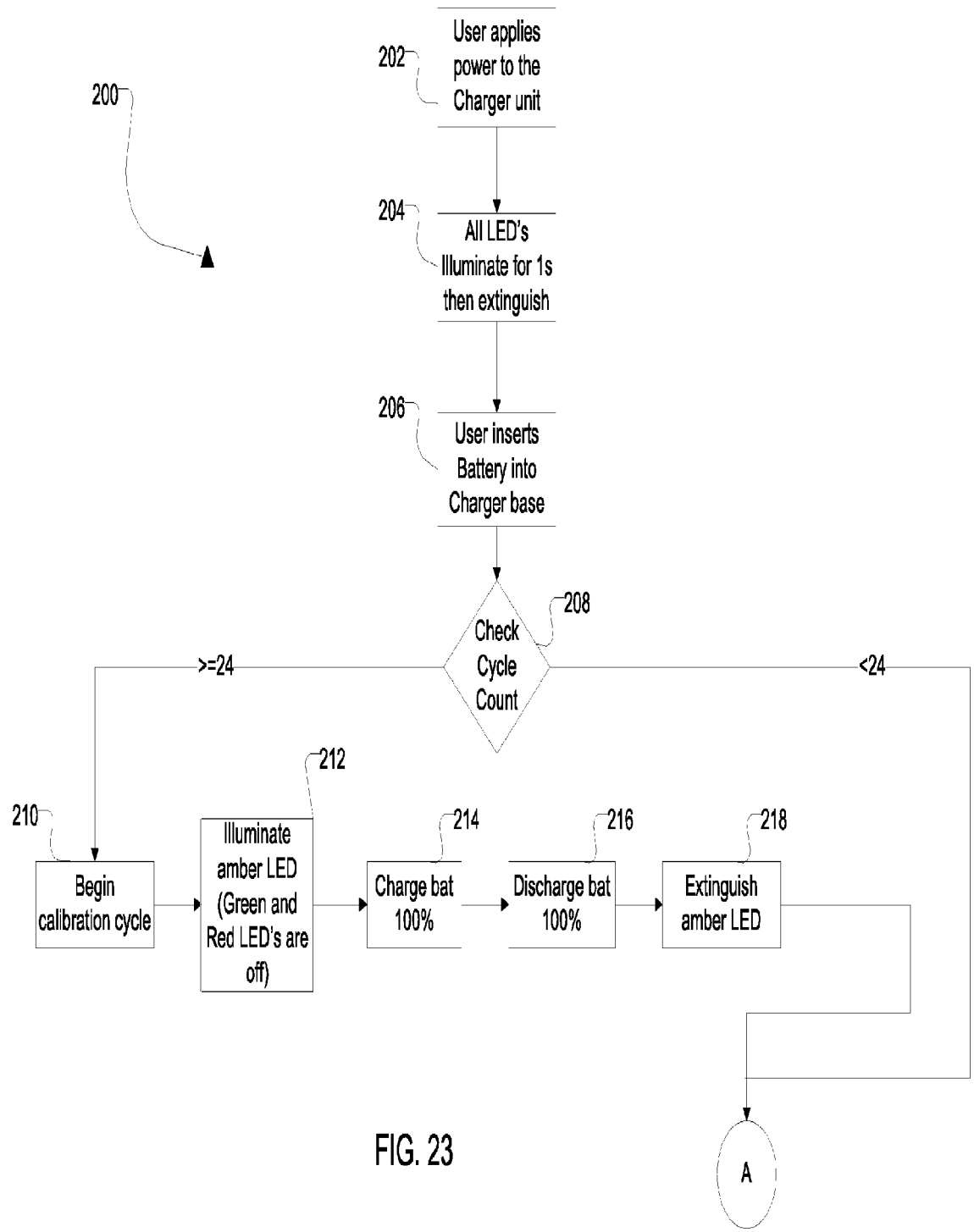
FIGS. 23-24 are a flowchart describing a process for charging a battery assembly of FIG. 1.

Process 200 for charging batteries 84 in battery assembly 80 in this embodiment is illustrated in FIG. 23. After the user applies power to the charger unit (202), all LED's on the charger illuminate for one second, then extinguish (204). The user inserts the battery into the charger base (206), then the system determines at decision point 208 how many recharging cycles the battery assembly 80 has gone through since its last calibration cycle. If that number is less than a predetermined threshold (in this embodiment, 24 charging cycles), the charging process 200 continues (through placeholder A) as shown in FIG. 24 and discussed below.

On the other hand, if at decision point 208 it is determined that the threshold cycle count has been reached, the system begins a calibration cycle (210). The amber LED in display 88 is illuminated and the green and red LED's are turned off (212). The battery is charged to 100% (214), then discharged completely (216). That calibration cycle is then complete, so the amber LED in display 88 is extinguished (218), and the charging process continues through placeholder A as shown in FIG. 24.

Figure 24:
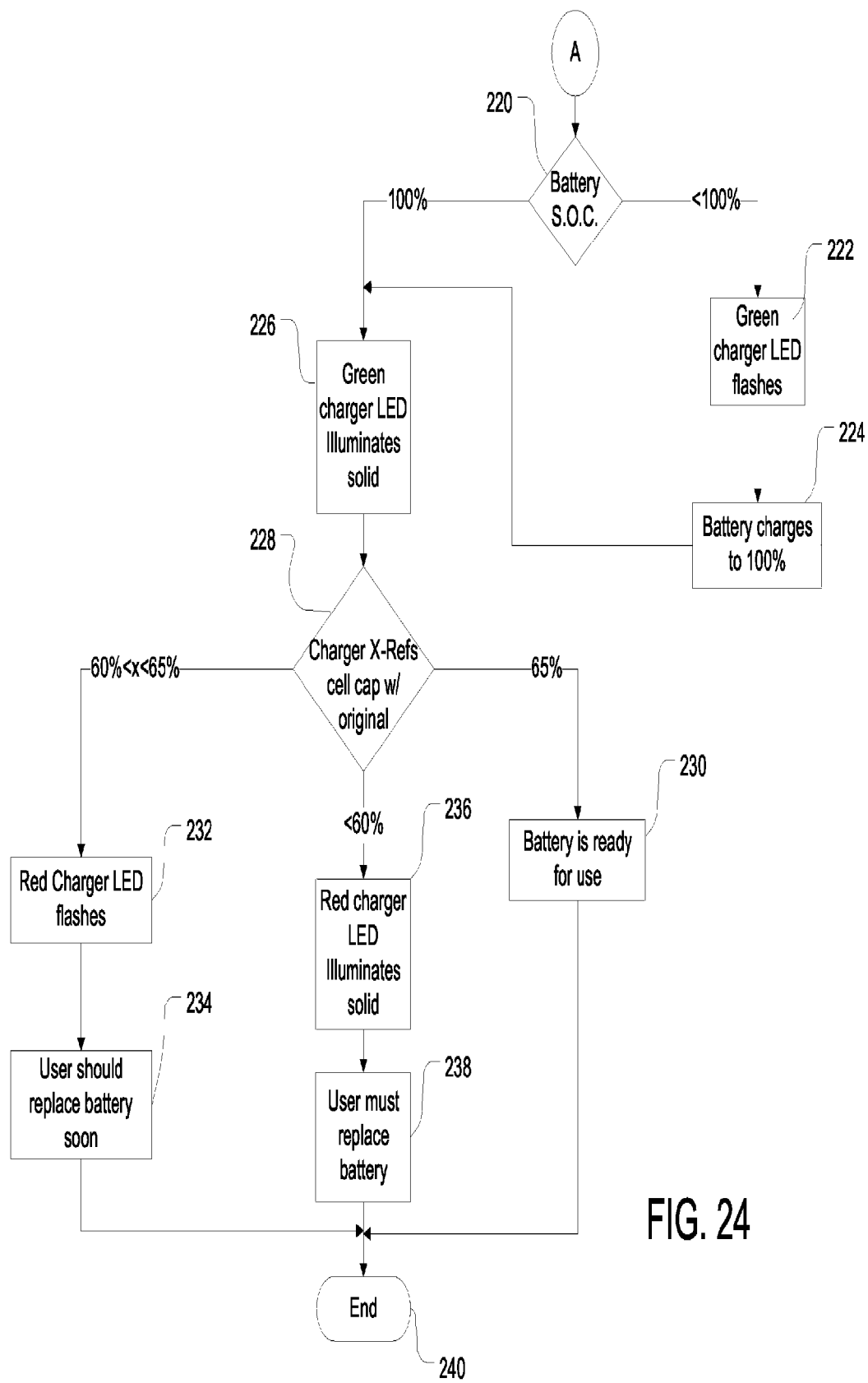

Process 200 for charging battery assembly 80 continues from placeholder A as shown in FIG. 24. The system detects the SOC at decision point 220. If it is less than 100%, the green LED in display 88 flashes (222), and the battery is charged to 100% (224). Then, or if the battery was determined at decision point 220 to be fully charged already, the green charger LED in display 88 is illuminated solid (226).

The charger then compares the cell capacity to the original cell capacity at decision point 228. If the current capacity is above an upper threshold (in this embodiment, 65% of the original capacity), then the battery is ready for use (230). If, on the other hand, the cell is below the upper threshold, but above a lower threshold (60% in this embodiment), then the red charger LED in display 88 flashes (232), and the user should replace the battery soon (234). Finally, if the new charge is less than the lower threshold as determined at decision point 228, the red charger LED in display 88 is illuminated solid (236) and the user must replace the battery (238). When the response (230, 234, or 236) to the charger's decision at decision point 228 is complete, the charging process ends (240).

Figure 25:
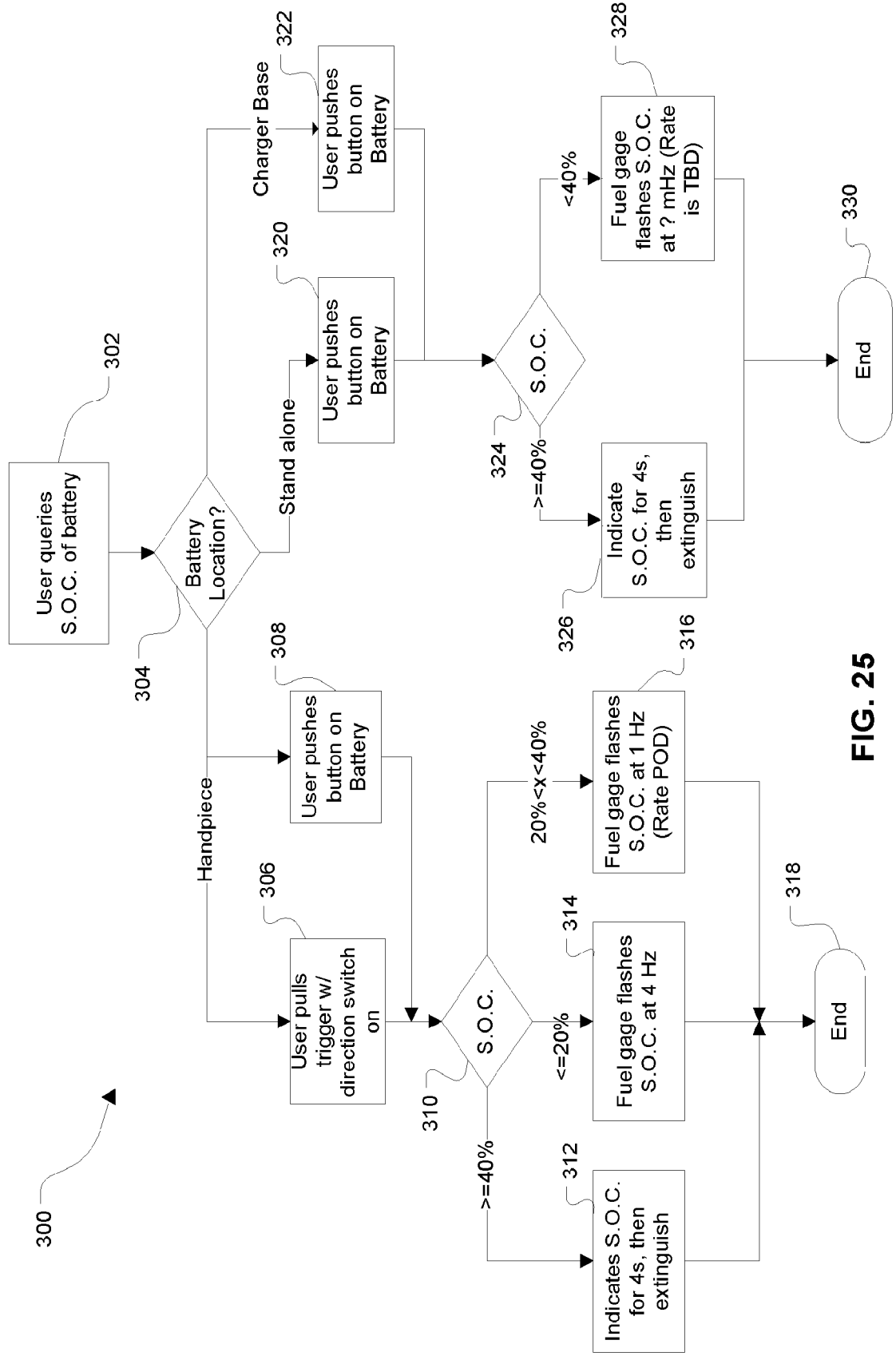
FIG. 25 is a flowchart describing a process for checking the state of charge of a battery assembly of FIG. 1.

FIG. 25 illustrates process 300 for checking the SOC of battery assembly 80. When the SOC query is initiated (302), the system determines at decision point 304 whether battery assembly 80 is attached to a hand piece 60, standing alone, or inserted into a charger base. In the illustrated embodiment, this determination is made based on the electrical connections through contacts 86, though in other embodiments the determination is made through other electrical communication, an electromagnetic signal(s), a magnetic signal(s), other mechanical configurations or switches, or other technique as will occur to those skilled in the art in view of the disclosure herein.

If the system determines at decision point 304 that the battery is attached to a hand piece, so that the query is initiated by a finger-switch pull with the direction switch on (306) or by the user pressing button 82.2 on the battery assembly 80 itself (308), then the system examines the SOC at decision point 310. If the charge is greater than an upper threshold (in this embodiment, 40% of a full charge), then the system indicates the SOC for four seconds and extinguishes the display (312). If the charge is less than a lower threshold (in this embodiment, 20% of a full charge), then the system flashes the SOC display at 4 Hz (314). If the charge is between the lower and upper thresholds, then the system flashes the SOC on the fuel gauge at 1 Hz (316). Method 300 ends (318) after the SOC is indicated in one of these ways.

The battery location determined at decision point 304 might alternatively be in "stand-alone" mode, where the battery is connected neither to a hand piece 60 nor a charging base, in which case the check is initiated by the user pressing button 82.2 on the battery assembly 80 (320). Likewise, if the battery assembly 80 is connected to the charging base, then the query again would have been initiated by the user pressing button 82.2 on the battery assembly 80 (322). In either event, the system determines the SOC at decision point 324. If the charge is greater than a threshold value (in this embodiment, 40% of a full charge), then the system indicates the SOC for four seconds, then extinguishes the indicator (326). If the charge is less than the threshold, the system flashes the SOC on the fuel gauge display at a rate of 4 Hz (328). After the respective SOC display (326, 328), method 300 then ends (330).

Figure 26:
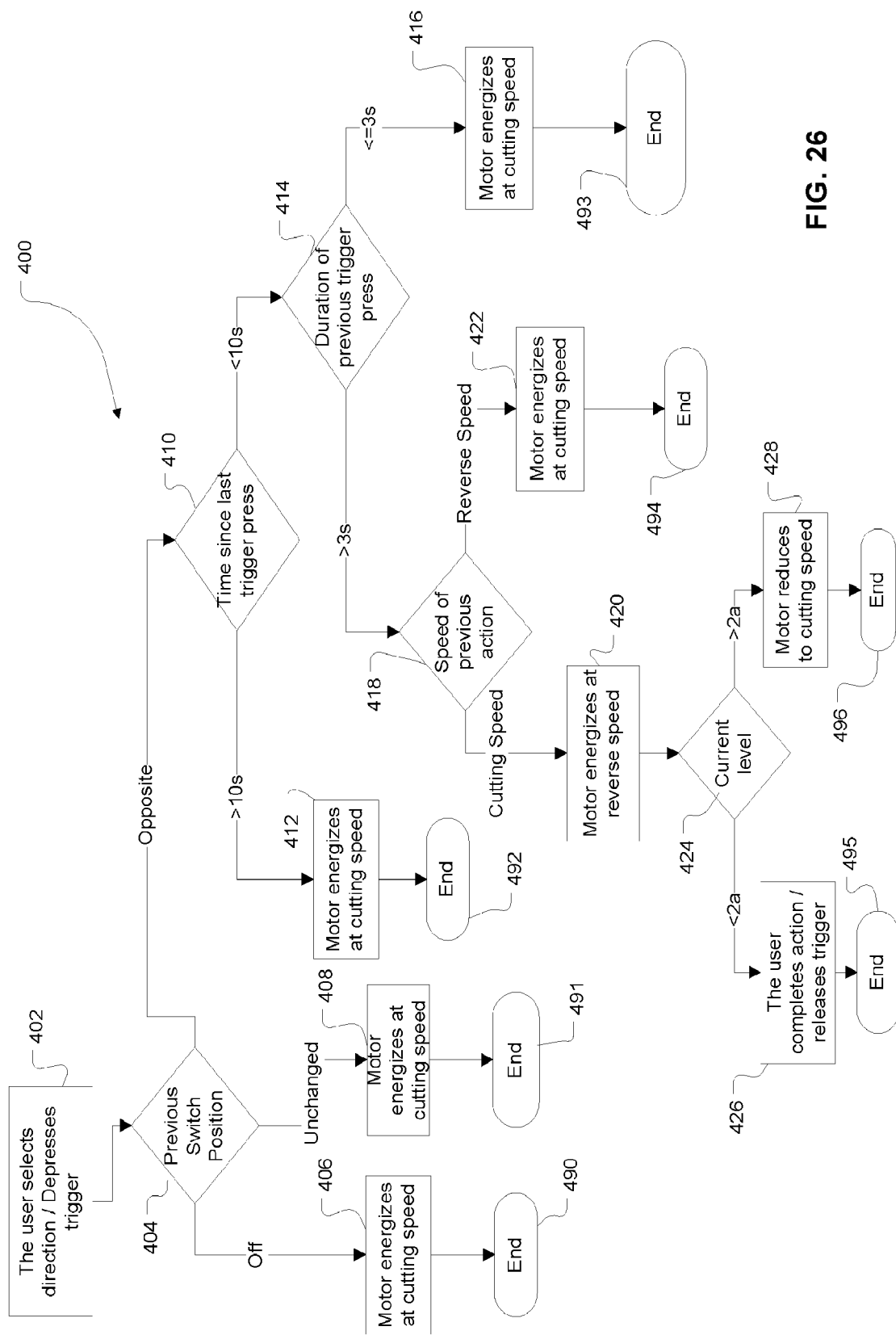
FIG. 26 is a flowchart describing a process for determining the desired cutting speed of the apparatus of FIG. 1.

Exemplary method 400 for determining the desired cutting speed (in the context, for example, of decision point 134 in FIG. 22, above) will now be discussed with reference to FIG. 26. This decision may be triggered by, for example, the user's selection of a direction using directional switch 36 and depressing finger switch 62 (402). The system then determines at decision point 404 whether the directional switch 36 is in the "off" position, is in the same (non-"off") position as it was at the time of the previous finger-switch-pull, or is in the opposite (non-"off") position from that at the time of the previous check. Note that, in the present embodiment, the switch must remain in a selected position for at least five seconds, or be accompanied by a finger-switch press, to be considered "in" a particular position for the purpose of this decision. If the switch had been in the "off" position, then the motor 32 energizes and progresses at cutting speed (406) as discussed herein, and process 400 ends (490). Likewise, if the direction switch is unchanged from the previous operation, then the motor 32 is again energized at cutting speed (408), and process 400 ends (491).

If, instead, the switch is in the opposite position compared to its position during the prior check, then the time since the last finger-switch press is checked at decision point 410. If the time is less than a certain threshold (in this embodiment, 10 seconds), then the motor 32 energizes at cutting speed (412), and process 400 ends (492).

If at decision point 410 it is determined that the time since the last finger-switch press is less than the threshold, then the system determines at decision point 414 whether the duration of the previous finger-switch press was greater or less than a particular threshold (in this embodiment, three seconds). If the duration of the previous finger-switch press was less than that threshold, then the motor 32 energizes at cutting speed (416), and process 400 ends (493).

If, instead, the duration of the previous finger-switch press (determined at decision point 414) was longer than the threshold, then the speed of the previous action is recalled at decision point 418. If the previous action was at reverse speed, then the motor 32 energizes at cutting speed (422), and process 400 ends (494).

If the previous action was at cutting speed, then the motor 32 energizes at reverse speed (420), and the current level is measured at decision point 424. If the current level being demanded by motor 32 remains less than a particular threshold (in this embodiment, 2A), then the user completes the cutting action and releases finger switch 62 (426), and process 400 ends (495). If the current level goes above the threshold, the motor reduces to cutting speed (428), and process 400 ends (496).

Figure 27:
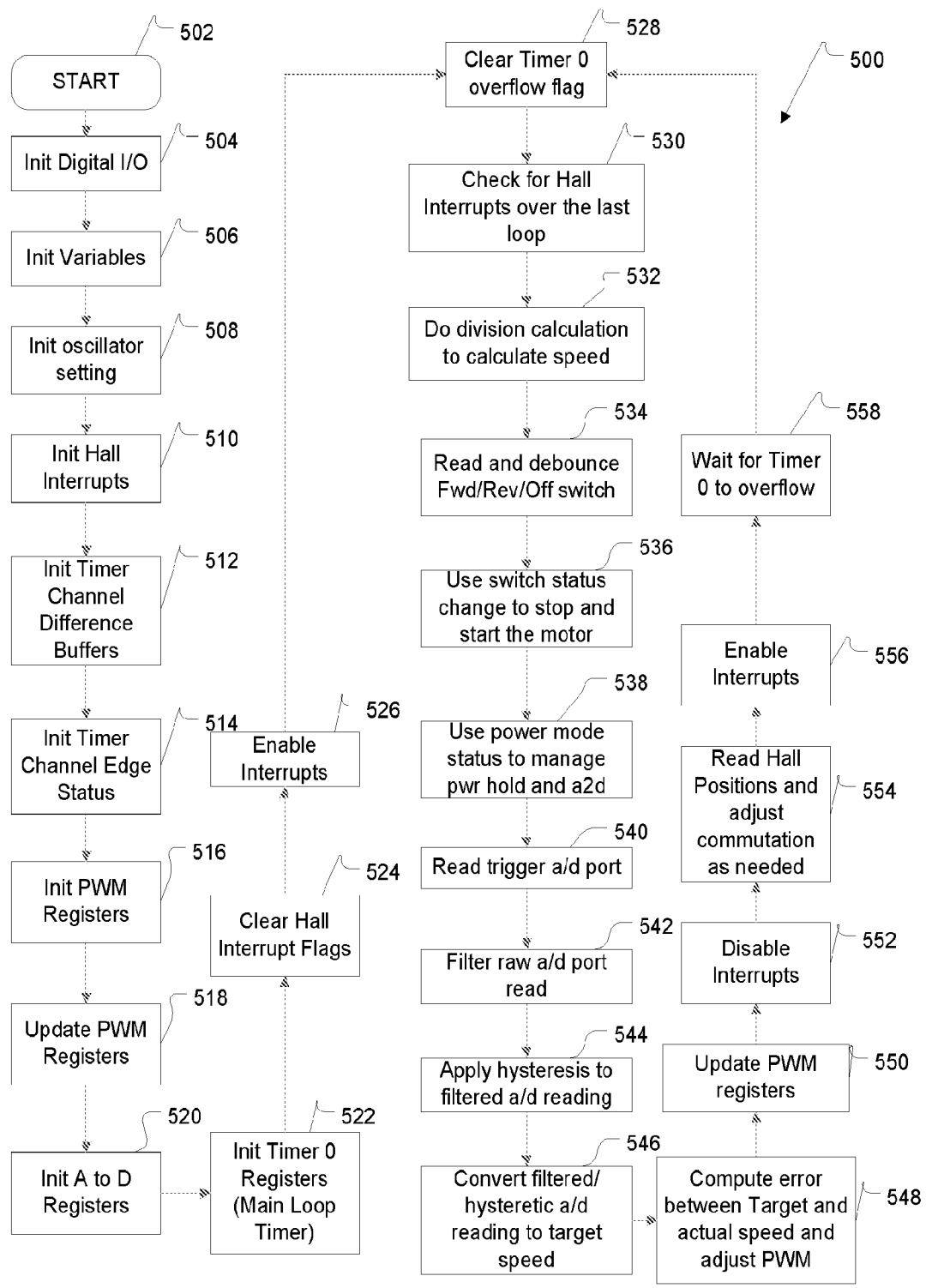
FIG. 27 is a flowchart describing an overall cutting system control process for the apparatus of FIG. 1.

FIG. 27 illustrates one embodiment 500 of the overall control process for device 20. Process 500 begins at start point 502, and the system initializes various subsystems: digital input and output (504), variables (506), oscillator settings (508), Hall sensor interrupts (510), timer channel difference buffers (512), timer channel edge status register (512), and pulse-wave modulation (PWM) registers (516). The PWM registers are updated (518), the analog-to-digital (A/D) registers are initialized (520), and the main loop timer "timer 0" registers are initialized (522). Any Hall interrupt flags that were present are cleared (524), and interrupts are enabled (526).

Process 500 then enters the main processing loop. The "timer 0" overflow flag is cleared (528), and the system checks for Hall interrupts over the last loop (530). The system then performs a division calculation to determine the speed of the present cutting operation (532), and the status of the forward/reverse/off switch 36 is read and debounced (534). Apparatus 20 monitors for any change in the status of finger switch 62, stopping the motor 32 if a change is detected during cutting operation (536). The power supply system is activated, and the analog-to-digital converter is reset (538). The finger-switch A/D port is read (540), the filtered A/D port is read (542), and hysteresis is applied to that filtered reading (544). The filtered hysteretic A/D reading is converted to a target speed (546). The system then computes the error between the target and actual speed of the motor 32 and adjusts the PWM signal (548). The PWM registers are updated (550), and interrupts are disabled (552). The Hall sensor positions are read and motor commutation is adjusted as needed (554). Interrupts are enabled again (556), and the system waits for timer 0 to overflow (558) before returning to the beginning of the main loop 528.

Figure 28:
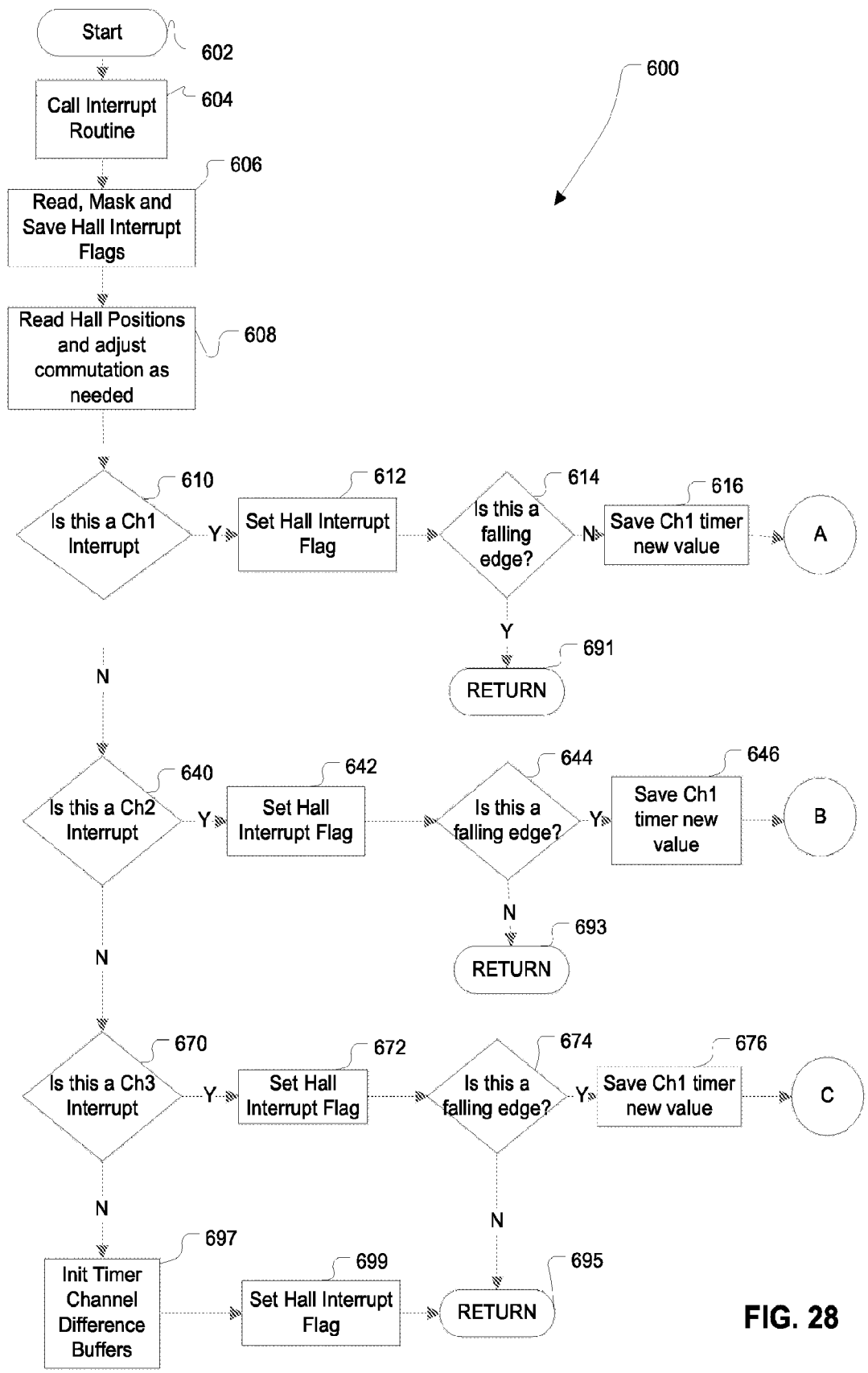
FIGS. 28-29 are a flowchart describing a process for handling interrupts triggered by motor sensors in the motor of FIG. 6A.
Figure 29:
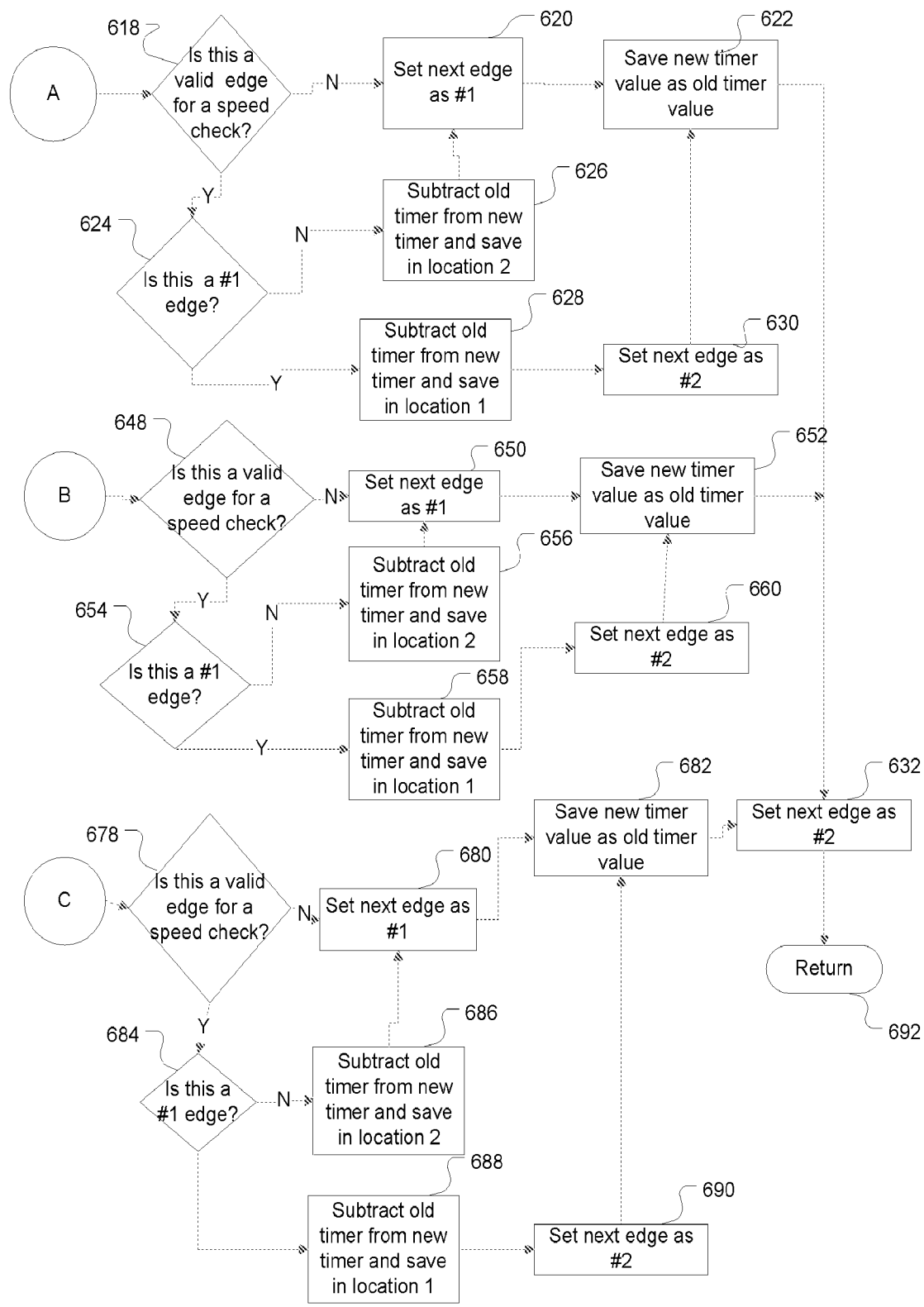

FIGS. 28-29 illustrate process 600 for handling interrupts triggered by internal motor sensors (see the discussion associated with FIG. 6.5 herein). Process 600 begins at start point 602, and the relevant interrupt routine is called (604). The Hall interrupt flags are read, masked and saved (606), and the Hall positions are read and the commutation of the motor 62 is adjusted as needed (608).

It is determined at decision block 610 whether the detected interrupt is a "Ch. 1" interrupt. If so (a "Y" result at decision block 610), the Hall interrupt flag is set (612), and the system determines at decision point 614 whether the Ch. 1 interrupt was a falling edge. If not ("N"), the system returns from the interrupt routine (691). If it was a falling edge (a "Y" result at decision point 614), then the new value of the Ch. 1 timer is saved (616), and process 600 continues through placeholder A in FIG. 29. As can be seen there, the system decides at 618 whether this is a valid edge for a speed check. If not, the next edge is set as a "#1" edge (620), and the new timer value is saved as the "old timer value" (622). On the other hand, if this is a valid edge for a speed check (that is, a positive result at decision point 618 was reached), then it is determined whether the detected edge is a "#1" edge (624). If not, the old timer value is subtracted from the new timer value and saved in "location 2" (626), and process 600 continues at block 620. If, instead, this is a "#1" edge, then the old timer value is subtracted from the new timer value and saved in location 1 (628), the next edge is set as a "#2" edge (630), and process 600 continues at block 622. After block 622, the three channels, with two buffers per channel, are added together (632), and the interrupt routine returns (692).

If it is determined at decision point 610 that this is not a "Ch. 1" interrupt, then it is determined whether this is a "Ch. 2" interrupt. If so, then logic analogous to the processing of a Ch. 1 interrupt is followed, where each reference number is 30 greater than the corresponding element in the processing of the Ch. 1 interrupt as discussed just above. Processing continues through either return point 693 or return point 692 in an analogous fashion, as illustrated in FIG. 28.

If the system decides at decision point 640 that this is not a Ch. 2 interrupt, it considers at decision point 670 whether this is a Ch. 3 interrupt. If so, the interrupt is processed in a fashion analogous to the handling of a Ch. 1 interrupt, through elements having reference numbers 60 greater than those that dealt with the Ch. 1 interrupt. Process 600 continues through return point 695, placeholder C, and/or return point 692, as appropriate.

If the system determines at decision point 670 that this is also not a Ch. 3 interrupt, then the timer channel difference buffers are initialized (697), the timer channel edge status is initialized (699), and the interrupt handler routine completes at return point 695.

Figure 31:
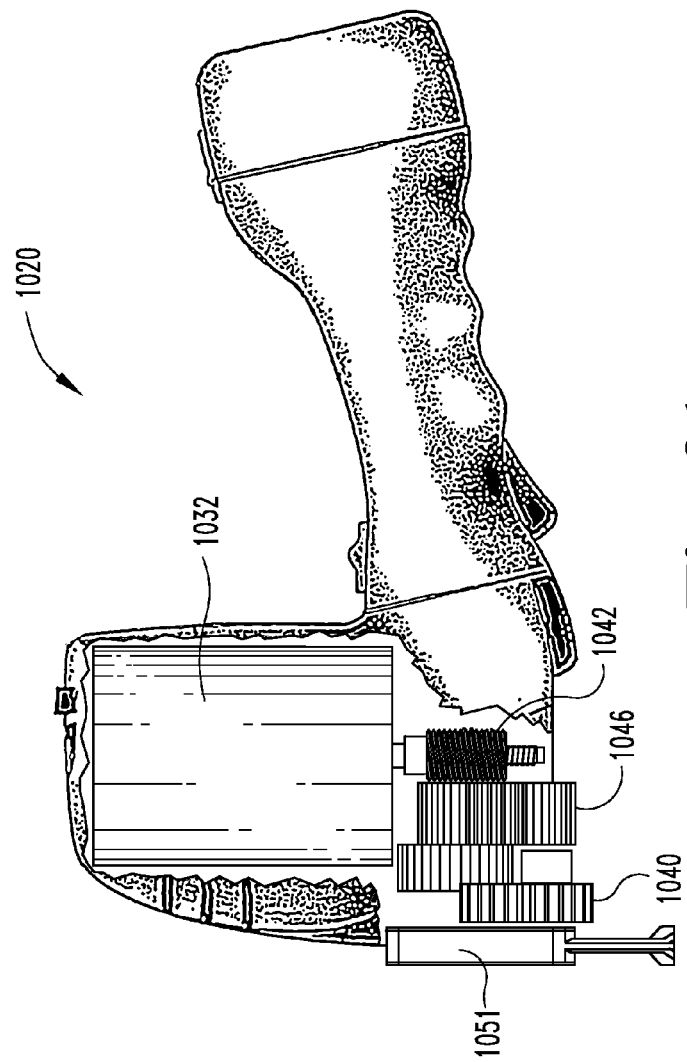
FIG. 31 is a view of the apparatus of FIG. 30A with portions of a cover removed.
Figure 32:
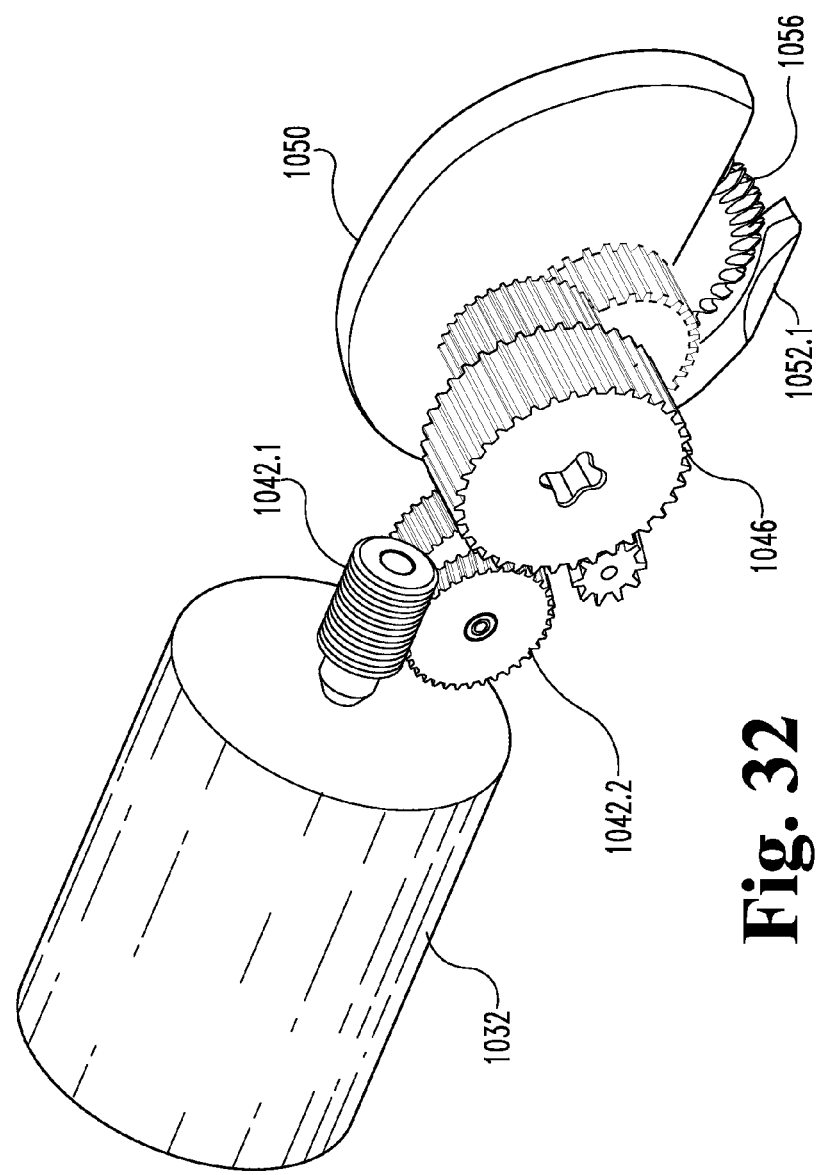
FIG. 32 is a perspective view of the motor, gear train, and cutting assembly of the apparatus of FIG. 30A.
Figure 33:
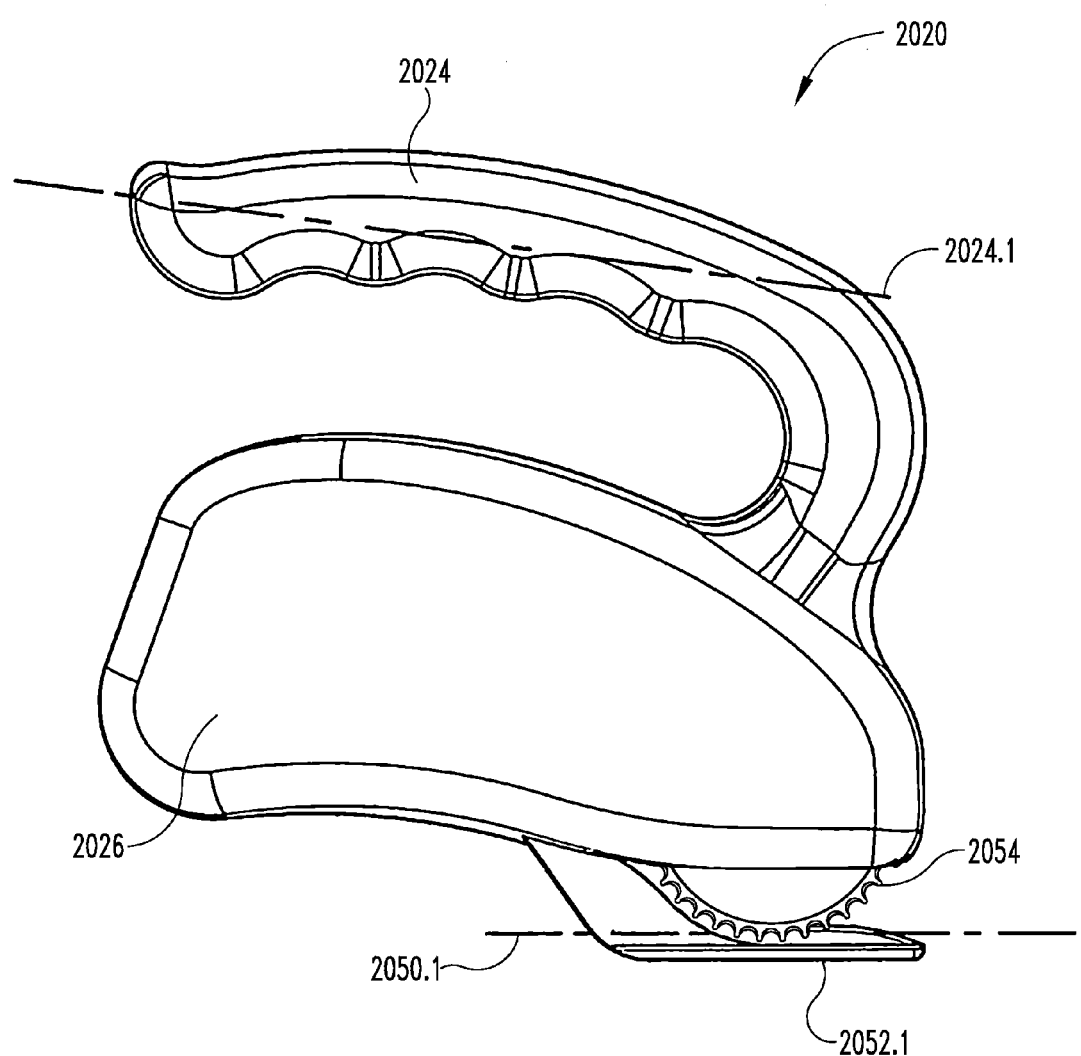
FIG. 33 is a side elevational view of an apparatus according to another embodiment of the present invention.
Figure 34:
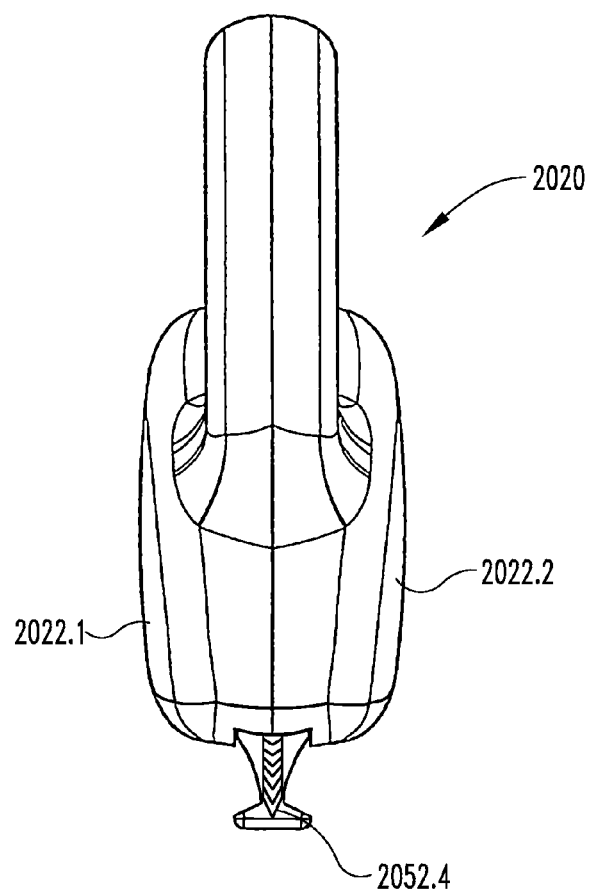
FIG. 34 is a front planar view of the apparatus of FIG. 33.
Figure 35:
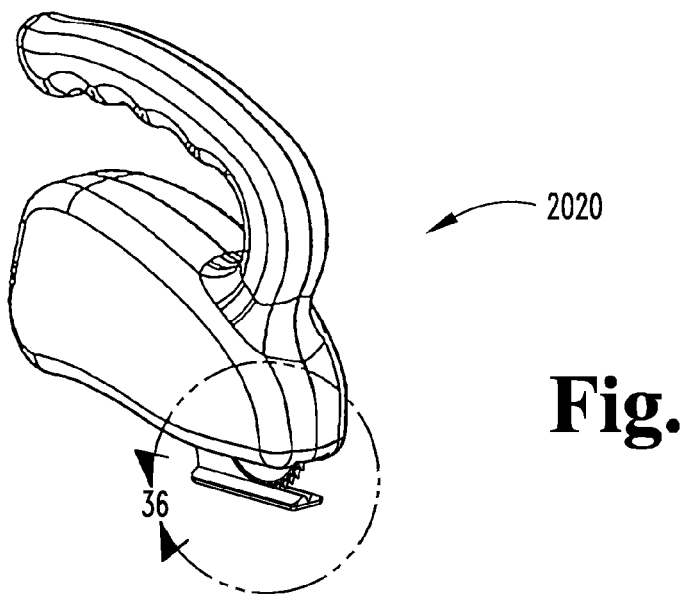
FIG. 35 is a perspective view of the apparatus of FIG. 33.
Figure 36:
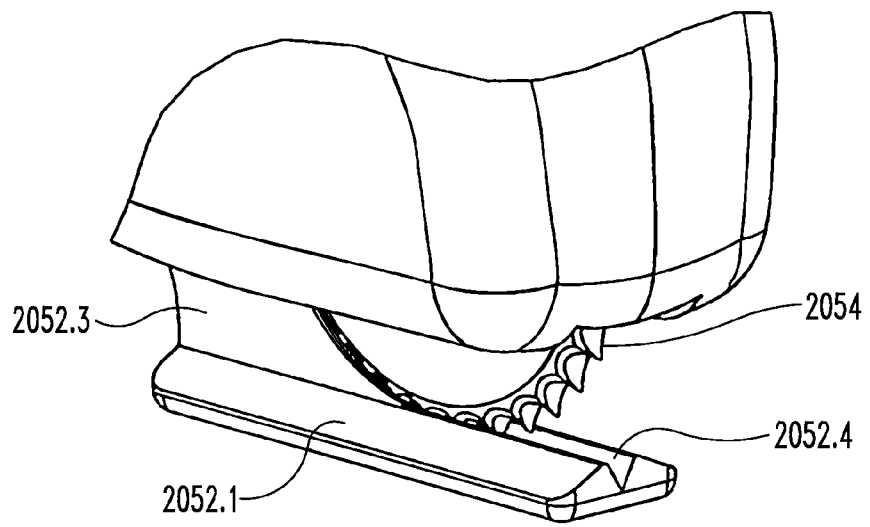
FIG. 36 is a close up of a portion of FIG. 35.

FIGS. 30-32 depict an apparatus 1020 according to another embodiment of the present invention. Apparatus 1020 is similar to apparatus 20, except for the gear reduction assembly 1040. As best seen in FIGS. 31 and 32, gear reduction assembly 1040 includes a single worm pair 1042. Worm wheel 1042.2 drives a first spur gear 1046. Spur gear 1046 continues a drive train with a plurality of other spur gears to achieve the desired speed reduction and torque increase for cutting wheels 1056 and 1054. However, in some embodiments, it has been found that having a pair of worm drives (as in apparatus 20) can provide for a more compact and quieter gear train.

FIGS. 33-36 depict yet other embodiments of the present invention. Apparatus 2020 is similar to device 20, but with some differences. Apparatus 2020 includes a single circular cutting wheel 2054 that splits and shears the material moving along a path 2050.1 and between cutting wheel 2054 and foot 2052.1. The access 24.1 of handle 24 is generally parallel to material flow path 2050.1.

Cutting wheel 2054 extends into a v-shaped, flat-surfaced cutting groove 2052.5. In some embodiments, the top edges of groove 2052.5 include sharp edges, and/or squared-off edges with a small radius of curvature. The meeting of the teeth of cutting wheel 2054 with groove 2052.5 provides a scissors effect.

Figure 37:
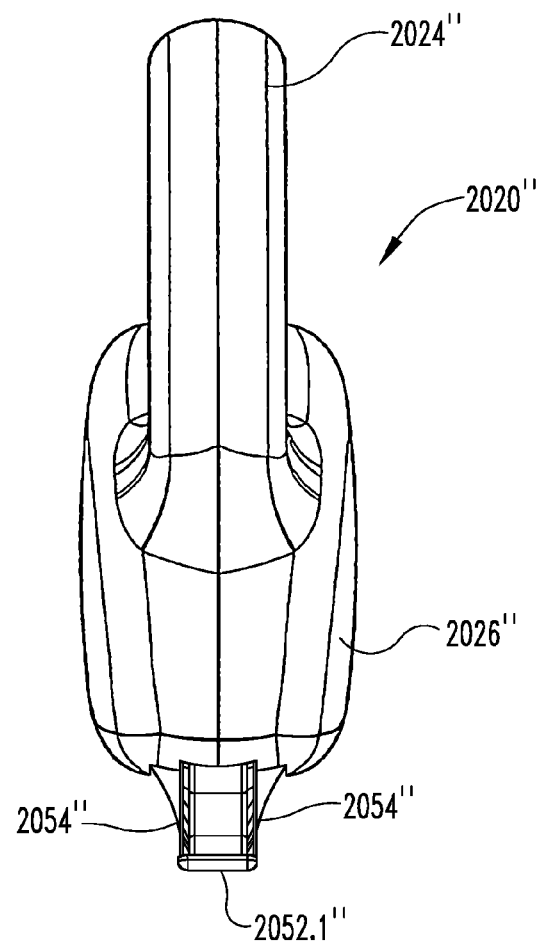
FIG. 37 is a variation of the embodiment shown in FIG. 33.

FIG. 37 shows an apparatus 2020" similar to apparatus 2020, but including a pair of spaced apart cutting wheels 2054". By having two spaced apart cutting wheels, apparatus 2020" cuts a wider swath through the cast, making it easier to remove.

Figure 38C:
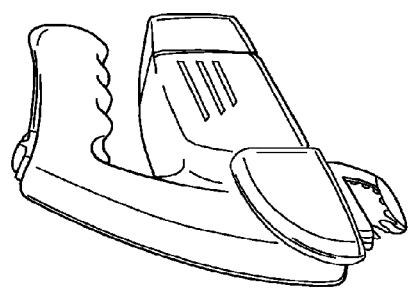
FIG. 38C is a frontal, left side perspective view of the apparatus of FIG. 38A.
Figure 38B:
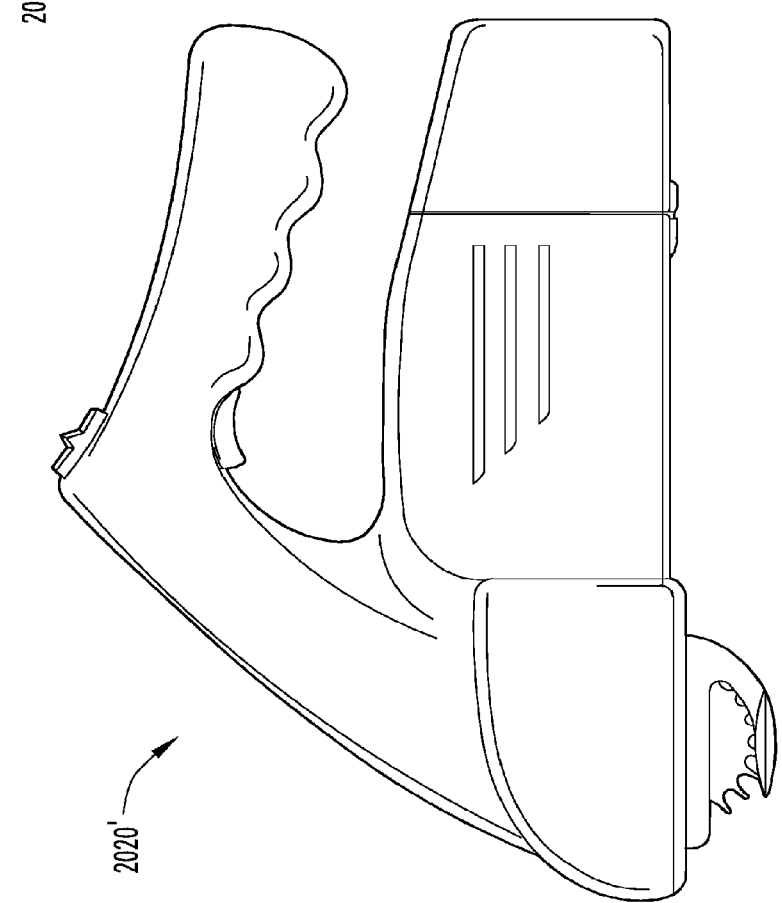
FIG. 38B is a side elevational view of the apparatus of FIG. 38A.

FIG. 38 depicts an apparatus 2020' similar to that of apparatus 2020. However, apparatus 2020" includes cutting and shearing wheels 2056" and 2054" arranged relative to a keel similar to the arrangement of apparatus 20. Further, apparatus 2020" includes a handle axis substantially parallel to the path of material flow.

FIG. 39 shows an apparatus 3020 for cutting through a layer of material. Apparatus 3020 includes an in-line handle 3024 located between motor 3032 and cutting assembly 3050. The axis 3024.1 is substantially parallel to the path 3050.1 of material flow, although the two axes intersect at a point in front of apparatus 3020, such that apparatus 3020 is slightly inclined relative to the material flow path.

Figure 40B:
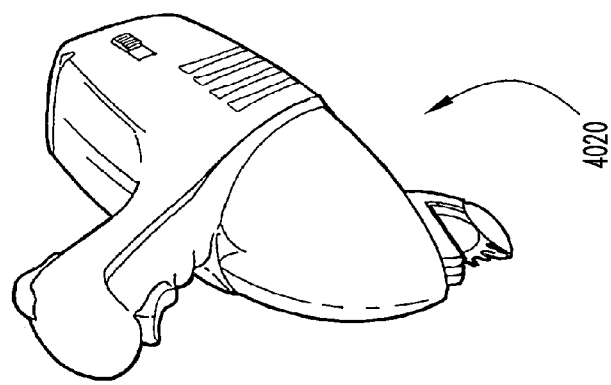
FIG. 40B is a left side, frontal perspective view of the apparatus of FIG. 40A.
Figure 40A:
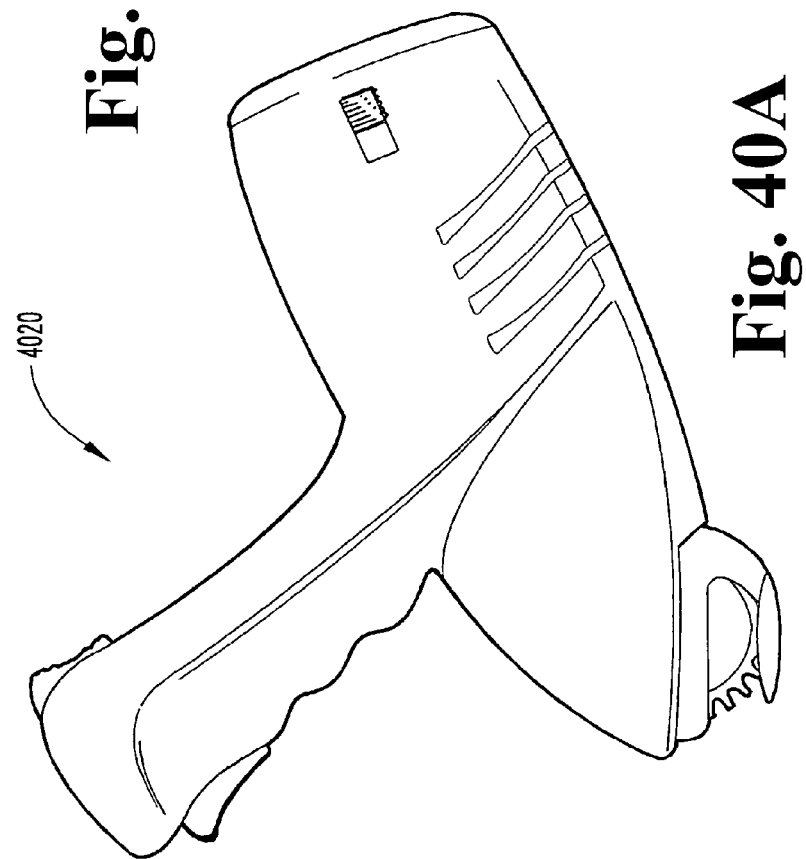
FIG. 40A is a side elevational view of an apparatus according to another embodiment of the present invention.

FIG. 40 shows an apparatus 4020 according to another embodiment of the present invention. Apparatus 4020 includes a handle 4021 that is substantially perpendicular to material flow path 4050.1, although the two axes intersect at a point slightly aft of cutting assembly 4050. Apparatus 4020 is adapted and configured for the operator to hold it from an upwardly projecting handle, that in some embodiments is slightly inclined forward.

FIG. 41 shows an apparatus 5020 according to another embodiment of the present invention. The handle 5024 is generally rounded, bulbous, and somewhat shaped like a small football. The axis 5024.1 is substantially parallel to the material flow path 5050.1.

FIG. 42 shows a splitting and shearing wheel 6054 according to another embodiment of the present invention. Wheel 6054 includes a splitting edge, with squared off edges, that extends roughly halfway around wheel 6054. The other half of the circumference of the wheel includes a sharp edge 6054.3. In this embodiment, the splitting edge 6054.5 splits apart the hard cover of the cast, and the sharp edge 6054.3 shears the soft wrapping. In this embodiment, the operator has the ability to hesitate his forward advancement of the apparatus 6020 for greater control, if desired.

Figure 43:
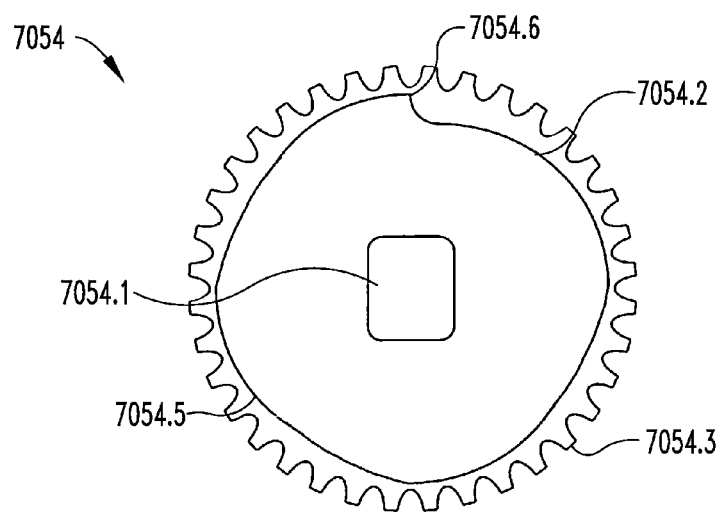
FIG. 43 shows a side elevational view of a splitting and shearing wheel according to another embodiment of the present invention.

FIG. 43 shows a splitting and shearing wheel 7054 according to another embodiment of the present invention. Wheel 7054 combines features for both splitting the hard portion of the cast, as well as other features for shearing the soft material. A plurality of teeth for splitting the hard cast 7054.3 are arranged in a generally cylindrical pattern around a driven interface 7054.1. On one face of wheel 7054, there is a single shearing sector 7054.2 that extends generally around the wheel, terminating in a tip 7054.6.

Figure 44:
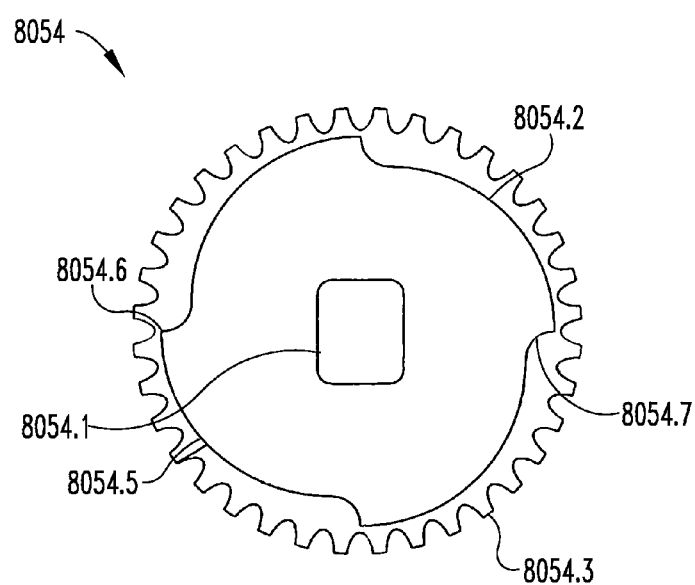
FIG. 44 shows a side elevational view a splitting and shearing wheel according to another embodiment of the present invention.
Figure 45A:
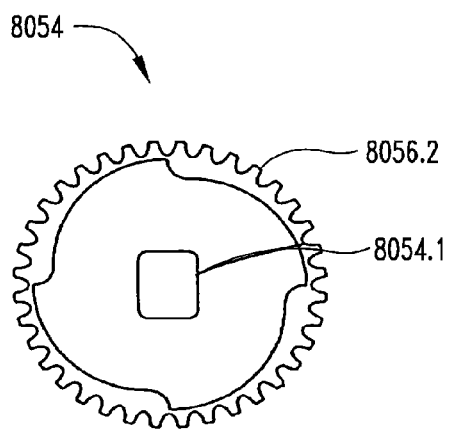
FIG. 45A is a frontal view of apparatus of FIG. 44.
Figure 45B:
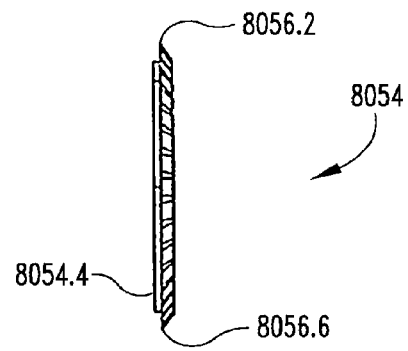
FIG. 45B is a side elevational view of the apparatus of FIG. 45A.
Figure 45C:
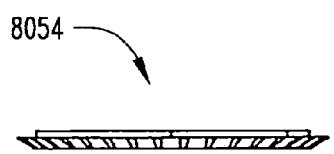
FIG. 45C is a bottom plane view of the apparatus of FIG. 44.
Figure 45D:
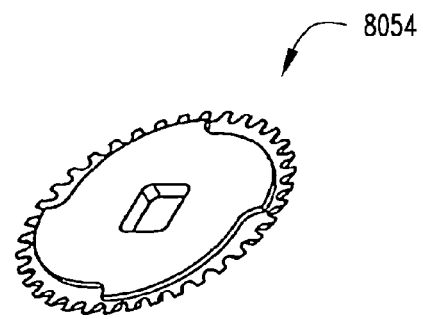
FIG. 45D is a perspective view of the apparatus of FIG. 44.

FIGS. 44 and 45 shows a wheel 8054 that includes four, equally spaced shearing sectors 8054.2 arranged around a central drive interface 8054.1. Each sector preferably includes a circular portion 8054.5 that extends from a concave transition 8054.7 to a tip 8054.6. Further extending around the periphery wheel 8054 are a plurality of squared-off, sharp-edged splitting sectors 8054.1. As discussed previously with regards to wheels 6054 and 7054, the shearing function is accomplished by the shearing sectors 8054.2. The splitting of the hard portions of the cast is accomplished by the teeth 8054.3.

Figure 46:
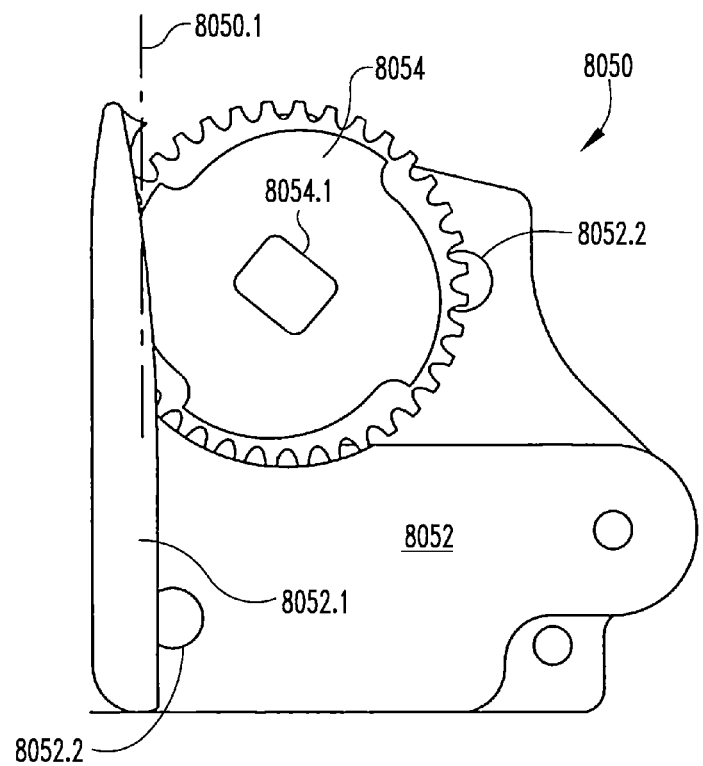
FIG. 46 shows the apparatus of FIG. 44 in a cutting assembly.
Figure 47:
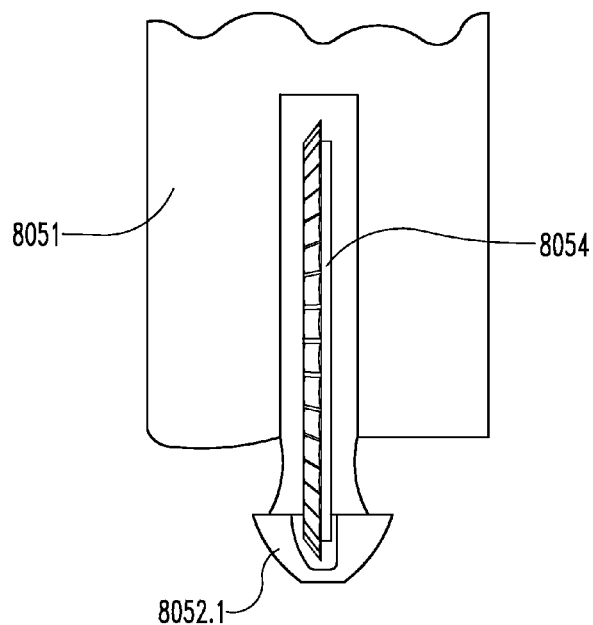
FIG. 47 is a front elevational view of the cutting assembly depicted in FIG. 46.

FIGS. 46 and 47 show wheel 8054 assembled into a cutting assembly 8050. Cutting assembly 8050 is supported by a pair of dowel holes 8052.2 located on either side of the rotational axis of wheel 8054. Foot 8052 extends generally parallel to material flow path 8050.1, and as previously described, protects the patient's arm from wheel 8054. As best seen in FIG. 47, foot 8052.1 includes a groove that receives within it the distal most portion of wheel 8054. Cutting assembly 8050 includes an increase in the distance of the shearing sectors from the center point of wheel 8054 to the distal edge of the wheel within the groove, and thereby creates an up and down cutting mechanism or scissors action that simultaneously shears the soft cast material along with the severing of the hard cast material. Likewise, the wheels 6054 and 7054 further combine the shearing and severing actions with one wheel.

FIG. 48 shows a combined severing and shearing wheel 9054 according to another embodiment of the present invention. FIGS. 48 and 49 show a family of wheels in which the shearing teeth, rather than being squared-off as in FIG. 9, are instead extended to a sharp tip. Because of this sharp tip, in some embodiments, wheels 9054 can penetrate the surface of the material being severed and thereby drive the surface. Referring to the five wheels shown in FIG. 48, the teeth of the wheel are spaced apart by a distance that corresponds to the weave pattern of a woven fiberglass material that is often used for the fabrication of an orthopedic cast. In order to maintain this same spacing between adjacent teeth, the number of teeth divided by the diameter of the wheel is roughly constant. By having a pattern of teeth that are spaced apart to match the weave of the fiberglass, it is more likely that a tooth will more consistently drive the cutting apparatus relative to the cast with reduced fraying of the cast material.

Figure 49F:
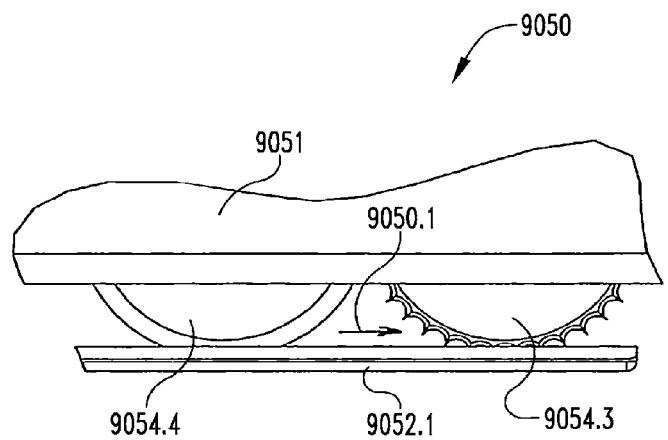
FIG. 49F is a side elevational view of a portion of an apparatus 9050.
Figure 49G:
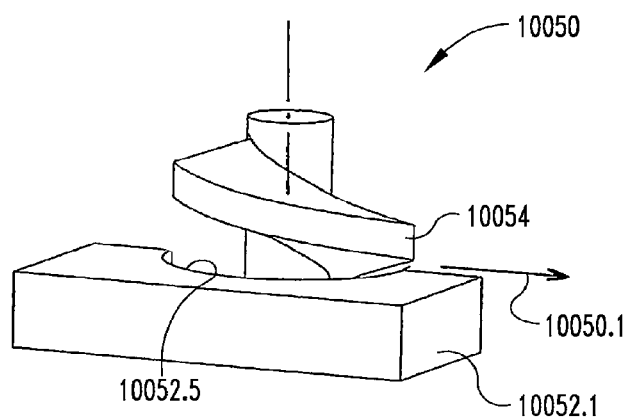
FIG. 49G is a perspective view of a portion of a cutting assembly according to another embodiment of the present invention.
Figure 50:
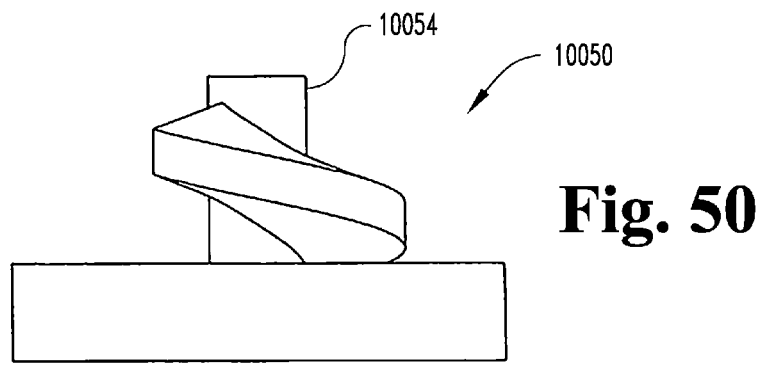
FIG. 50 is a side elevational view of the apparatus of FIG. 49G.
Figure 51:
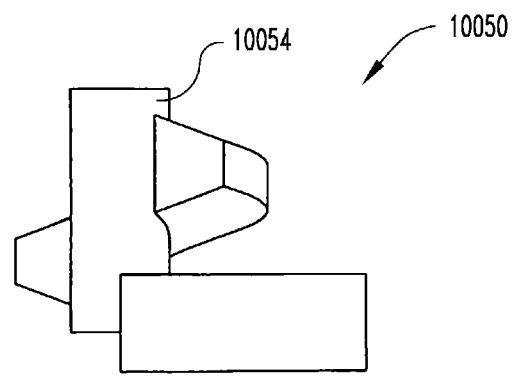
FIG. 51 is an end view of the apparatus of FIG. 49G.

FIG. 49F depicts a cutting assembly 9050 in which the splitting and shearing functions have been split onto two different wheels. A housing 9051 supports a first wheel having a splitting edge with a plurality of teeth 9054.3 that splits apart the hard portion of the cast. A second wheel having a sharp shearing edge 9054.4 follows the first wheel, and severs any soft material that has not split apart.

Yet other embodiments of the present invention contemplate embodiments in which an advancing wheel such as wheel 56 is located behind a splitting wheel such as wheel 54. In these embodiments, the second wheel does not perform a cutting function, but simply pulls the material past the front splitting wheel.

FIGS. 49, 50, 51, and 52 depict portions of a cutting assembly 10050 that includes a helical thread form. Helical shearing wheel 10054 rotates about a central axis. The threads of the helical form flow downward and pass over a sharp edged shearing face 10052.5. The material to be severed flows in a direction 10050.1 over the top face of foot 10052.1, and over the semi-circular shearing hole that receives the helical form 10054. As the helical threw threads rotate past this interface, the bottom edge of the threads and the top edge 10052.5 of the foot co-act to sever a semi-circular or crescent shaped piece from the material. These pieces drop away, and the material can be advanced to the next portion that is to be cut out. In the embodiment shown in FIGS. 49, 50, and 51, the cutting wheel 10054 is comprised of a single screw lead with one path downward for each revolution of the cutter.

Figure 52:
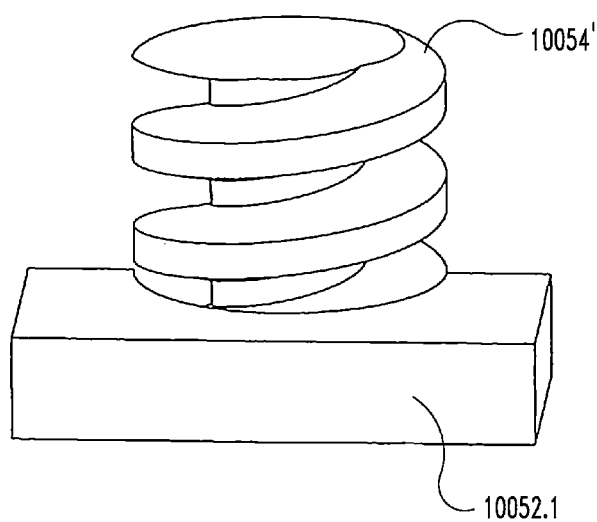
FIG. 52 is a perspective view of a portion of a cutting assembly according to another embodiment of the present invention.

FIG. 52 shows an alternate embodiment, in which the splitting wheel 10054" includes two or more screw leads as the screw thread revolves, there are two or more cuts made with each rotation, thus allowing for smaller crescent shaped pieces of the cast being severed with each cut. In other variation, the helical screw form cutter could be reciprocating rather than rotating. In another variation, there may be two or more cutting edges along the perimeter of the helical screw form. These two cutting edges can include a splitting cutter for cutting the hard outer cast with a second cutting edge having a shearing edge for severing soft cast materials.

Figure 53:
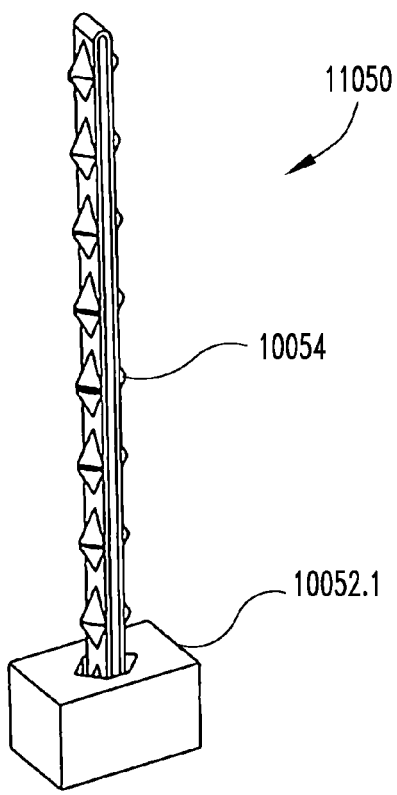
FIG. 53 is a perspective view of a portion of a cutting assembly according to another embodiment of the present invention.
Figure 54A:
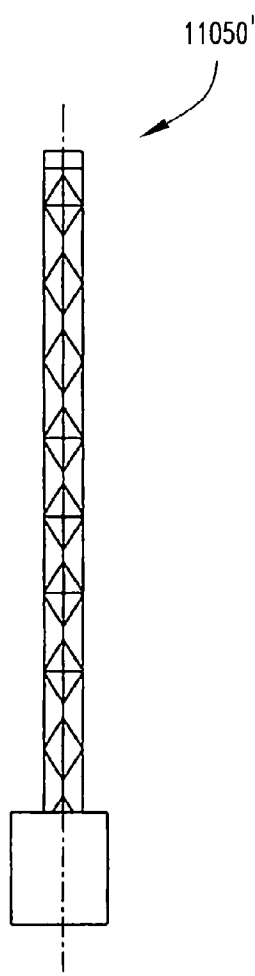
FIG. 54A is a side elevational view of a portion of a cutting assembly according to another embodiment of the present invention.
Figure 54B:
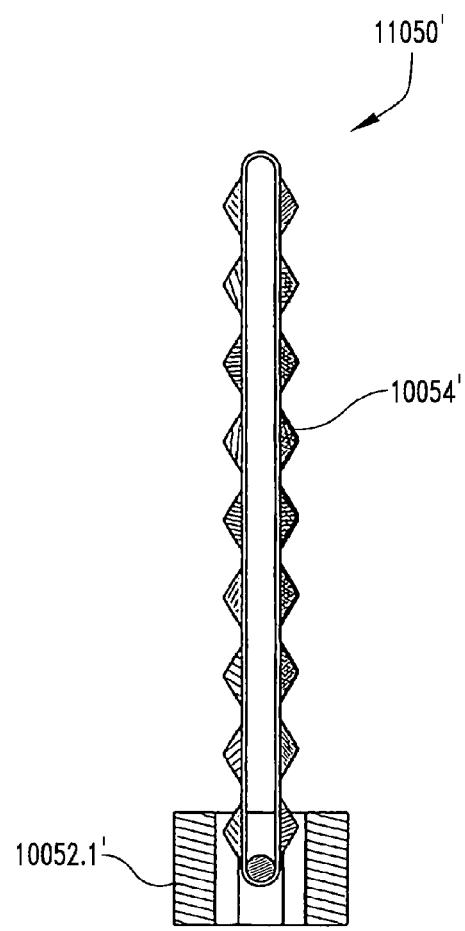
FIG. 54B is a orthogonal, cut-away view of the apparatus of FIG. 54A.

FIGS. 53 and 54 depict embodiments of the present invention that include components for splitting and severing the cast with either a reciprocating motion or a band saw motion. Referring to FIG. 53, a reciprocating splitting device 10054 is shown extending from a hole in a foot 10052.1. The surface of cutting element 10054 includes a plurality of diamond-shaped teeth. Splitting device 10054 reciprocates similar to a jigsaw. FIG. 54 shows an alternate version in which the diamond-shaped teeth are placed on a band 10054" that is rotationally supported by a roller within foot 10052.1" as well as a driven roller at the top (not shown).

Figure 55A:
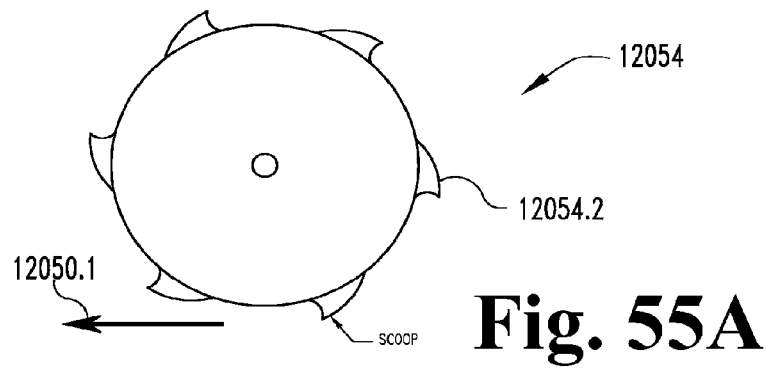
FIG. 55A shows a splitting device according to another embodiment of the present invention.
Figure 55B:
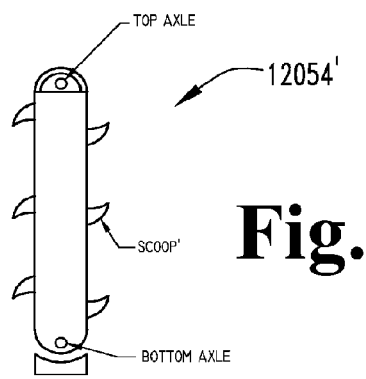
FIG. 55B is a side elevational view of the apparatus of FIG. 55A.
Figure 55C:
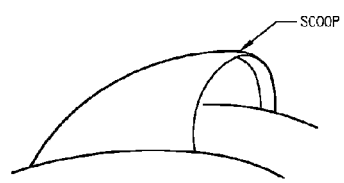
FIG. 55C is a close up perspective view of the apparatus of FIG. 55A.

FIG. 55 shows a splitting wheel 12054 according to another embodiment of the present invention. Wheel 12054 includes a plurality of cutting sectors 12054.2 characterized by a sharp-edged, substantially hollow scoop. As material flows in the direction indicated by path 12050.1, a scoop severs the hard portion of the cast with the sharp edge. In the middle of FIG. 55, a splitting device 12054" is shown having a plurality of scoops" attached to a belt that rotate about top and bottom axels.

Figure 56A:
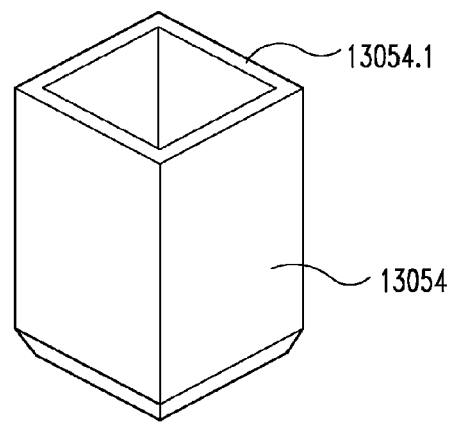
FIG. 56A shows a perspective view of a splitting device according to another embodiment of the present invention.
Figure 56B:
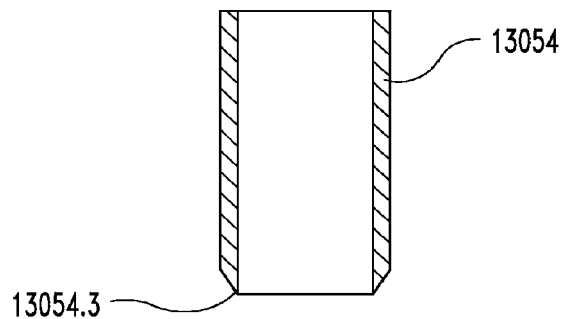
FIG. 56B is a cut-away view of the apparatus of 56A.

FIG. 56 shows a splitting device 13054 according to yet another embodiment of the present invention. Cutting device 13054 uses a reciprocating motion. One or more sharp edges 13054.3 are located at the distal end of splitting device 13054. As a cast passes underneath this device, the gearing mechanism 13040 (not shown) pushes splitting device 13054 downward and punches a hole in the cast in a shape similar to the shape of the sharp edges. Although a square cross-section has been shown, this device can be u-shaped (with an open side), round, oval, and including a non-closed shape such as a linear cutting edge.

Figure 57A:
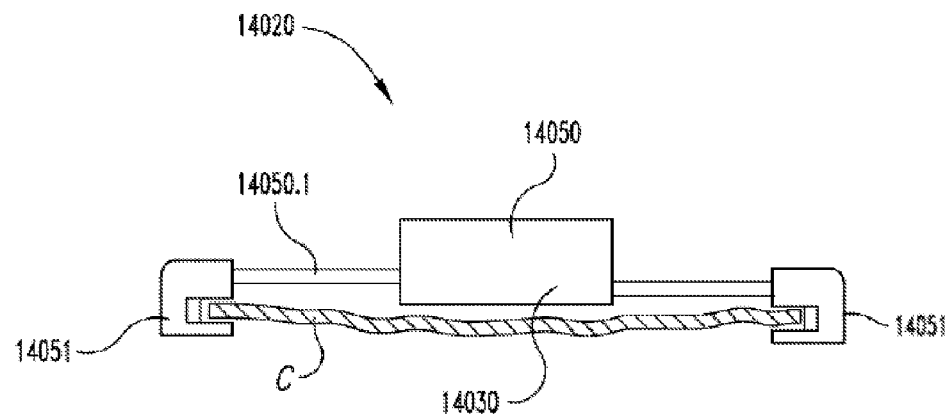
FIG. 57A shows a side schematic representation of a cast removal system according to another embodiment of the present invention.
Figure 57B:
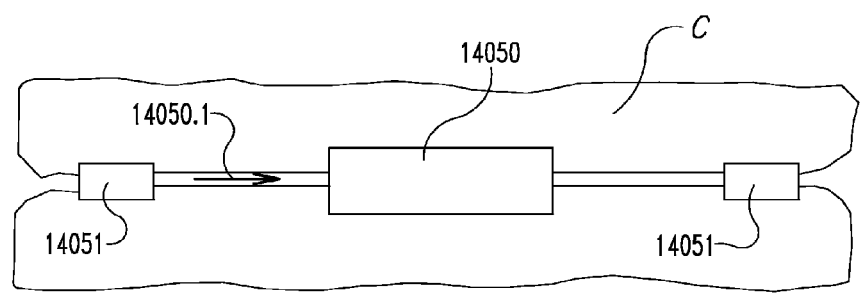
FIG. 57B is a top schematic representation of the apparatus of FIG. 57A.
Figure 58F:
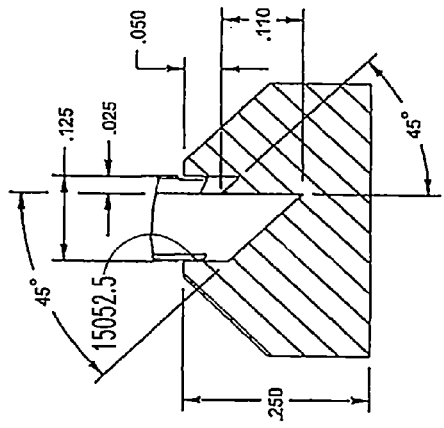
FIG. 58F is an enlarged, cut-away representation of a portion of the apparatus of FIG. 58C.
Figure 58A:
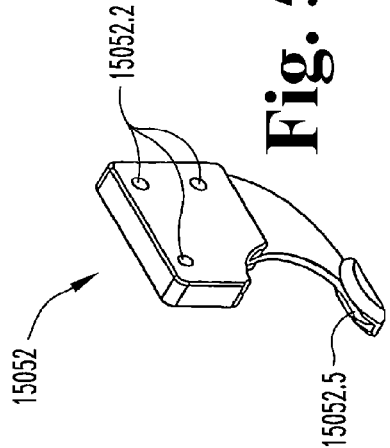
FIG. 58A shows a perspective view of a keel according to another embodiment of the present invention.
Figure 58C:
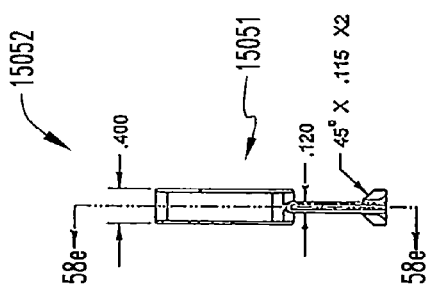
FIG. 58C is an end elevational view of the apparatus of FIG. 58A.
Figure 58E:
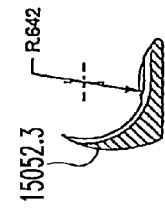
FIG. 58E is a cross sectional view of a portion of the apparatus of FIG. 58C.
Figure 58B:
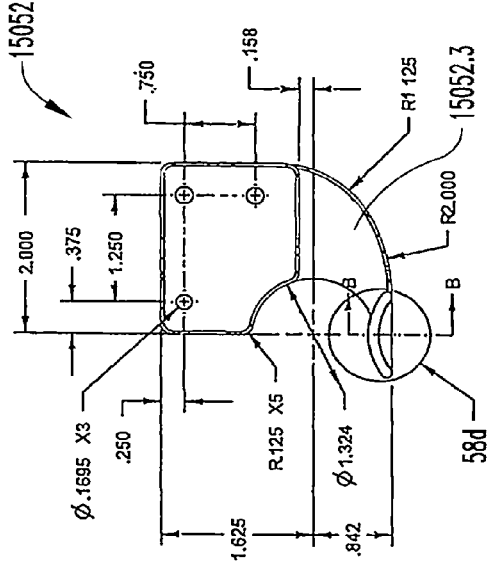
FIG. 58B is a front elevational view of the apparatus of FIG. 58A.
Figure 58D:
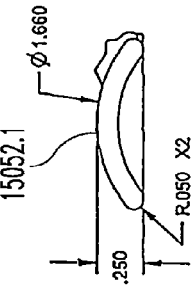
FIG. 58D is a close up of a portion of the apparatus of FIG. 58B.
Figure 59A:
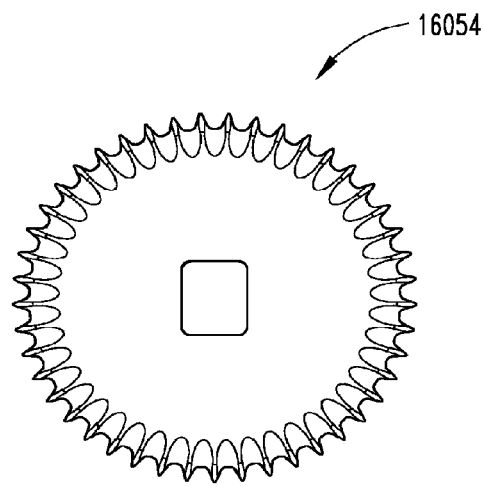
FIG. 59A shows a frontal view of a splitting assembly according to another embodiment of the present invention.
Figure 59C:
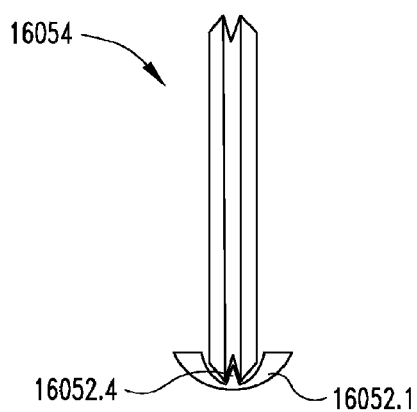
FIG. 59C is a side elevational view of the apparatus of FIG. 59A.
Figure 59B:
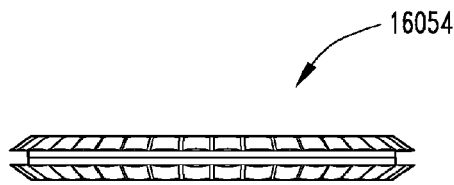
FIG. 59B is a bottom view of the apparatus of FIG. 59A.
Figure 59D:
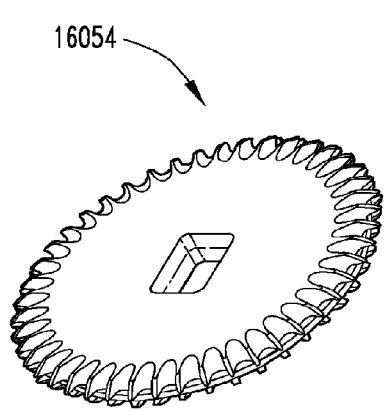
FIG. 59D is a perspective view of the apparatus of FIG. 59A.

FIG. 57 shows two views of a cast removal apparatus 14020 according to another embodiment of the present invention. A motorized cutting assembly is shown (in the top) located midway along a guiding rod 14050.1 and above a portion of a cast C. Located on either ends of 14050.1 are attachment housings 14051 that support the rods and the motorized cutting assembly. Further, in some embodiments, housings 14051 further grasp ends of the cast C to be removed and place the cast in tension. Motorized cutting assembly 14030 includes within it a cutting assembly 14050 (not shown) that extends downward and cuts the portion of cast beneath the pathway formed by rods 14050.1. Cutting mechanism 14050 is moved automatically from one end of the apparatus to the other end of the apparatus, and thereby removes a portion of the cast.

FIG. 58 shows various views of a keel 15052 according to another embodiment of the present invention. As best seen in the upper left corner and bottom center prospective views, keel 15052 extends only on one side of the splitting wheel 15054 (not shown). Three dowel holes 15052.2 provide support for keel 15052 to a plurality of support dowels 15034.2 (not shown). In some embodiments, keel 15052 is attached to the support 15034 by a plurality of quick release mechanisms that permit easy replacement or reverse direction attachment of the keel to the support. In one embodiment, the quick release mechanism includes a plurality of ball dent mechanisms that extend within holes 15052.2. The present invention contemplates other types of quick release attachments between the keel (and cutting assembly) with the support assembly.

FIG. 59 shows various views of a splitting or severing device 16054 according to another embodiment of the present invention. Splitting wheel 16054 includes a central groove around the circumference of the splitting wheel. The corresponding foot 16052.1 includes a sharp ridge that fits within the groove of the splitting wheel.

Figure 60:
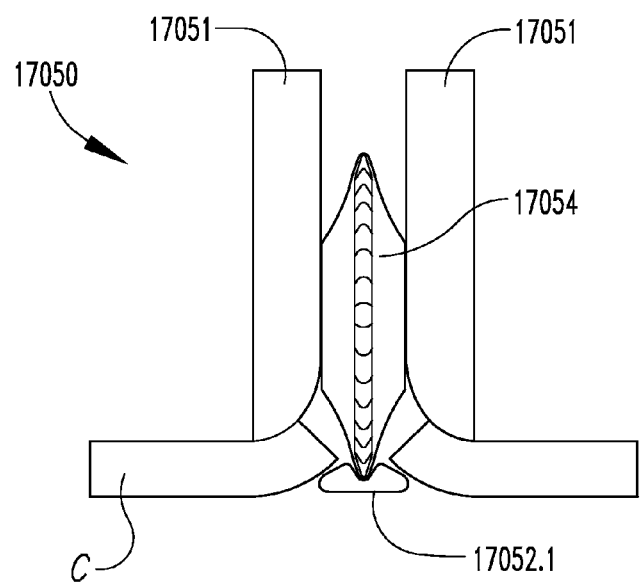
FIG. 60 shows a portion of a cutting assembly according to one embodiment of the present invention.

FIG. 60 shows an end view, close-up schematic representation of a splitting wheel 17054 located between plates 17051. A bottom foot 17052.1 can be mechanically elevated toward the centerline of wheel 17054 and thereby assist in deformation of the portion of the cast C to be cut. As shown in FIG. 60, foot 17052.1 has been elevated and pinches a portion of the cast C between it and the stationary members 17051, such that the portion of the cast C is forced upward toward the splitting wheel 17054.

FIG. 61 shows a cutting assembly 18050 according to another embodiment of the present invention. Device 18050 includes a sharp cutting edge, such as a razor edge 18052.4 extending along a beveled surface of the foremost part of arm 18052.3. In some embodiments, this edge can be replaced, such as a razor blade can be replaced. In some embodiments, the sharp edge extends to the forward most part of foot 18052.3, and thereby begins shearing of the soft cast material prior to splitting of the hard cast material by wheel 18054.

Figure 62A:
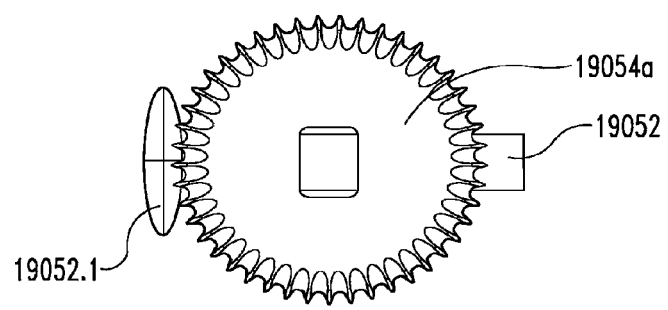
FIG. 62A shows a frontal view of a cutting assembly according to another embodiment of the present invention.
Figure 62B:
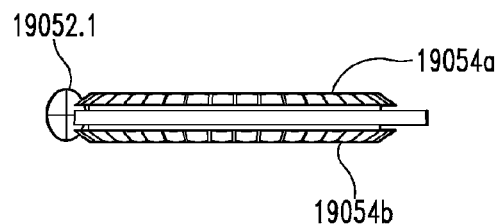
FIG. 62B is an orthogonal view of the apparatus of FIG. 62A.
Figure 62C:
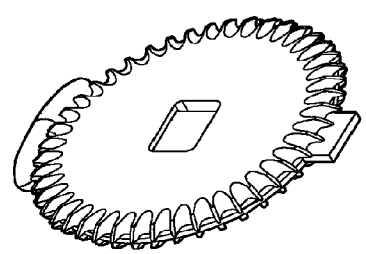
FIG. 62C is a perspective view of the apparatus of FIG. 62A.

FIG. 62 shows various views of a pair of splitting wheels 19054a and 19054b arranged on either side of a centrally located keel 19052. Keel 19052 extends between the splitting wheels, passing around the driven interfaces of the wheels, and extends to a foot 19052.1.

With regards to FIGS. 63-73, those of ordinary skill in the art will appreciate that the numbering system defined at the beginning of the Description of the Preferred Embodiment is only partly in effect. Those element numbers greater than or equal to 20XXX are consistent with the earlier described numbering convention. Otherwise, numbers in the range of four thousand or five thousand refer to elements shown on the drawings. Nonetheless, those of ordinary skill in the art will recognize similarities between the apparatus and methods shown in FIGS. 63-73 with the previous descriptions and figures.

Figure 63A:
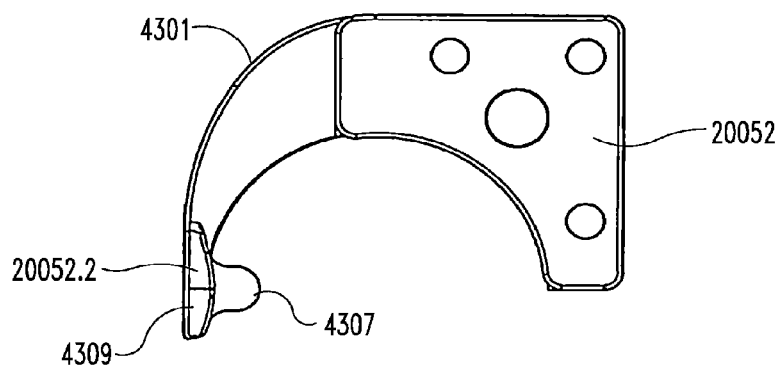
FIG. 63A shows a side elevational view of a keel assembly according to another embodiment of the present invention.
Figure 63B:
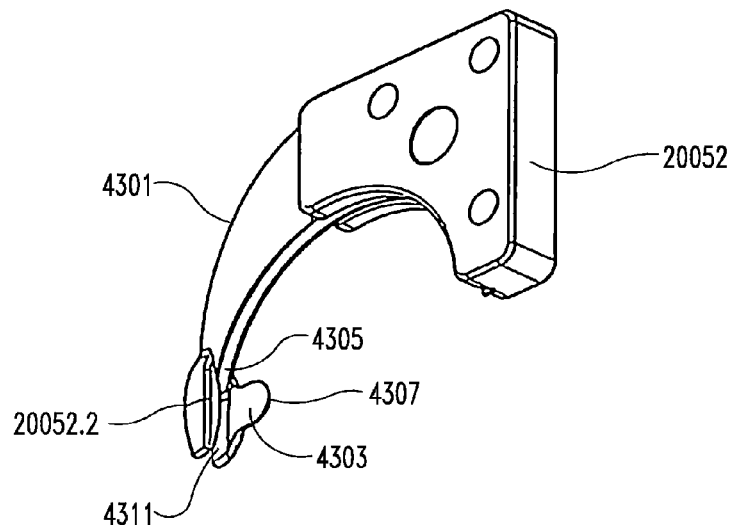
FIG. 63B shows a perspective view of the keel assembly of FIG. 63A.
Figure 64A:
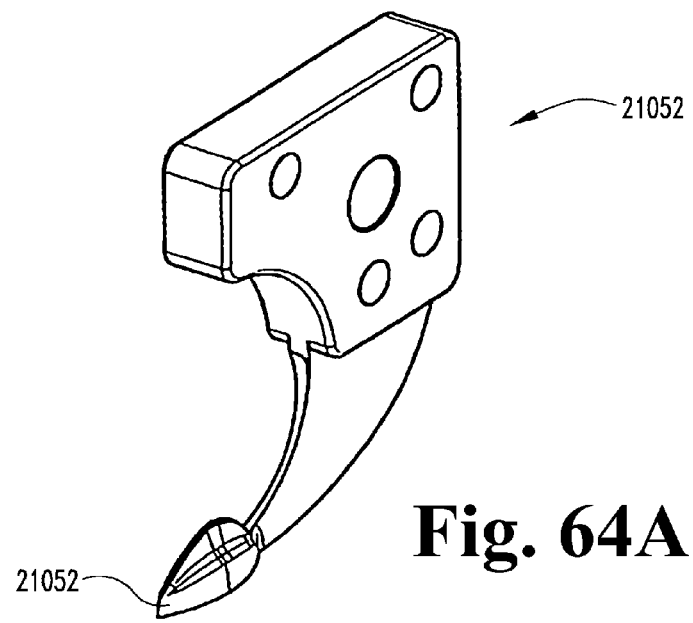
FIG. 64A shows a perspective view of a keel assembly according to another embodiment of the present invention.
Figure 64B:
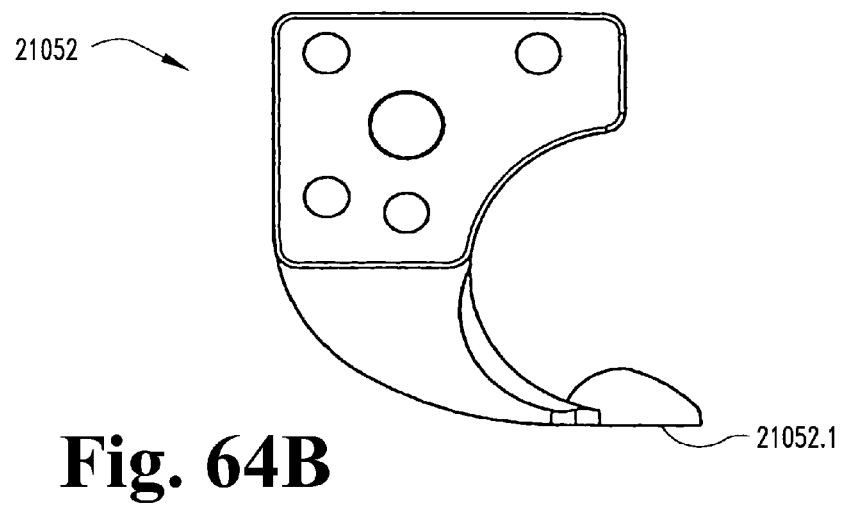
FIG. 64B shows a side elevational view of the keel assembly of FIGS. 64A.

FIGS. 63-67 show various views of alternative keel assemblies. The foot attached to the distal end of the keel 20052 could be shaped in a multiple of configurations depending on the desired function of the cast cutter device. In one variation as depicted in FIG. 63, the foot extends off the keel 4301 with a buttressed flat shearing face 4303 facing the middle of the grooved pathway 4305 where it engages the shearing portion of the cutter wheel. In this variation the foot rises upward in a rounded design 4307 from the foot base 4309 to provide a longer contact with the shearing portion of a wave form cutter wheel and the shearing face of the foot thereby increasing the shear interface articulation length between the two and resulting in a more efficient shearing of the soft cast material. In one variation the shearing wave form may be a separate cutter wheel than the piecing and advancing wheel. In the depicted variation cutter pathway of the foot is open between the foot's inner sides 4311 extending back to the cutter groove located in the keel 4305. In one variation the foot 21052.1 might consist of only having a shearing face side as shown in FIG. 64. By creating a space in the foot between the sides or eliminating the portion of the foot that does not incorporate the shearing plate the debris from cast material accumulating within the cutter pathway is reduced thus lowering the potential for clogging and resistance to the cutter.

Figure 65A:
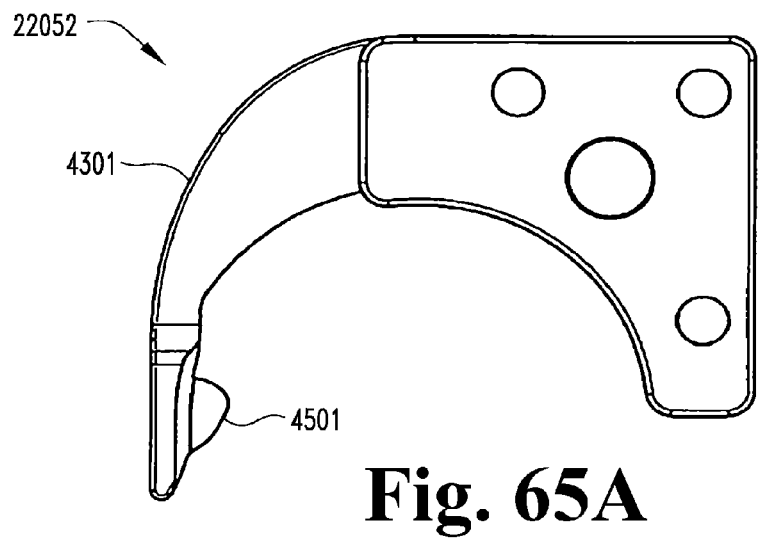
Figure 65B:
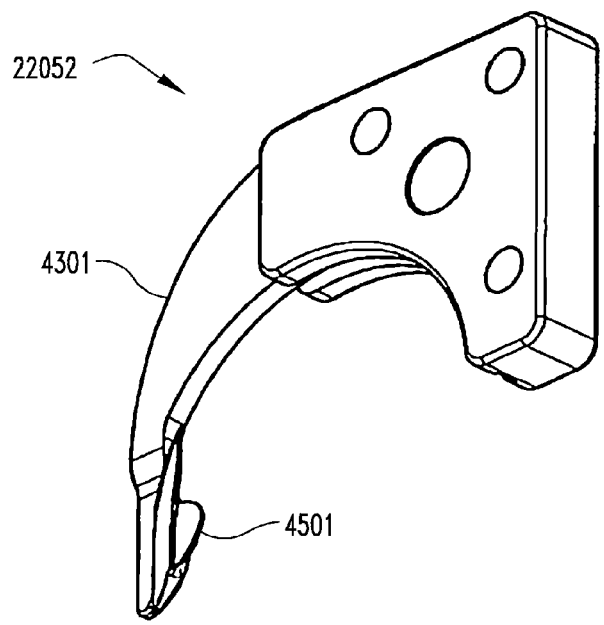

In another variation the heightened shearing face 4501 might extend further out from the keel 22052 as depicted in FIG. 65. The desired foot design could be any combination of foot height and length depending shear interface articulation length desired between the shearing cutter and the foot shearing plate. In one variation there might be a slight angle between the cutter and the foot shearing plate to optimize the interface between the cutter and foot in facilitating a shearing action. In one embodiment the angle might be 3°. In one variation it might be between 2° and 5°. Any angle could be utilized to achieve the desired result. By creating a space in the foot between the sides or eliminating the portion of the foot that does not incorporate the shearing plate the debris from cast material accumulating within the cutter pathway is reduced thus lowering the potential for clogging and resistance to the cutter.

Figure 66A:
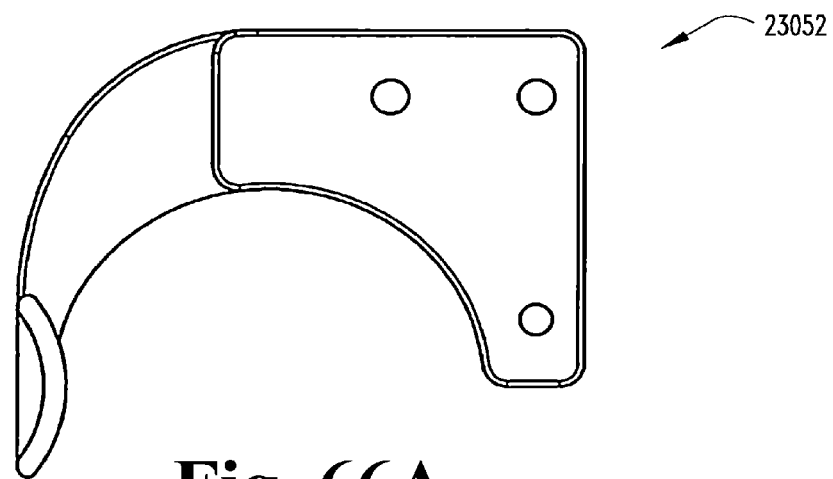
Figure 66B:
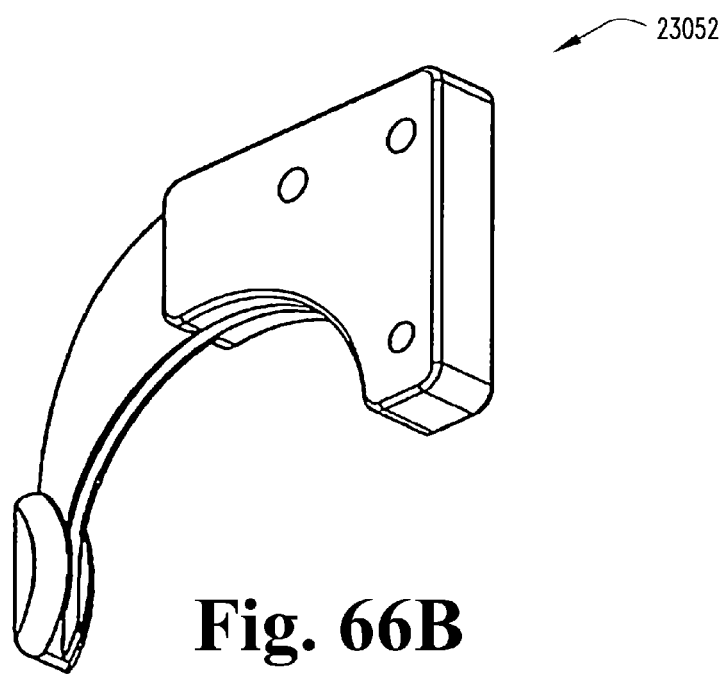
Figure 67A:
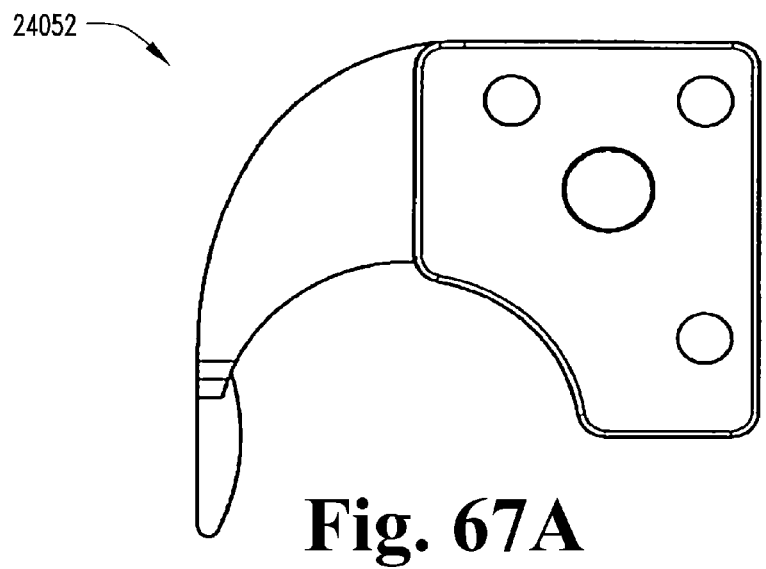
Figure 67B:
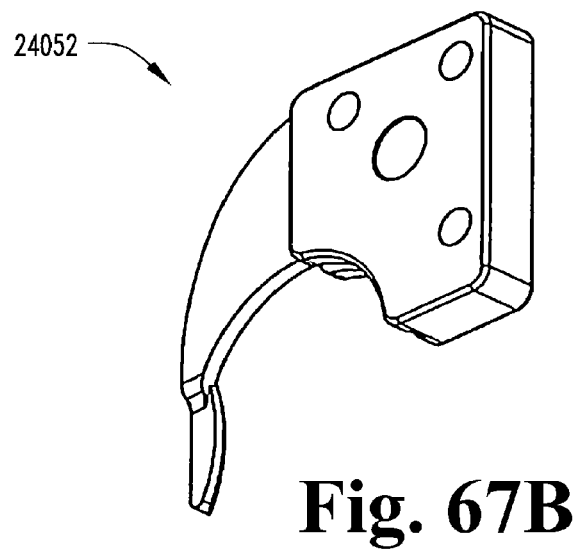

FIG. 66 depicts an alternative foot design 23052 that has a slight bevel from the bottom of the foot's distal end 4601. This bevel might reduce drag and minimize snagging the skin below the cast and providing a smoother pathway for the cast cutter device. FIG. 67 depicts a foot variation 24052 where the distal end of the foot 4701 extends further out from the keel 4301. Any length of foot might be utilized to achieve the desired objective.

Figure 68:
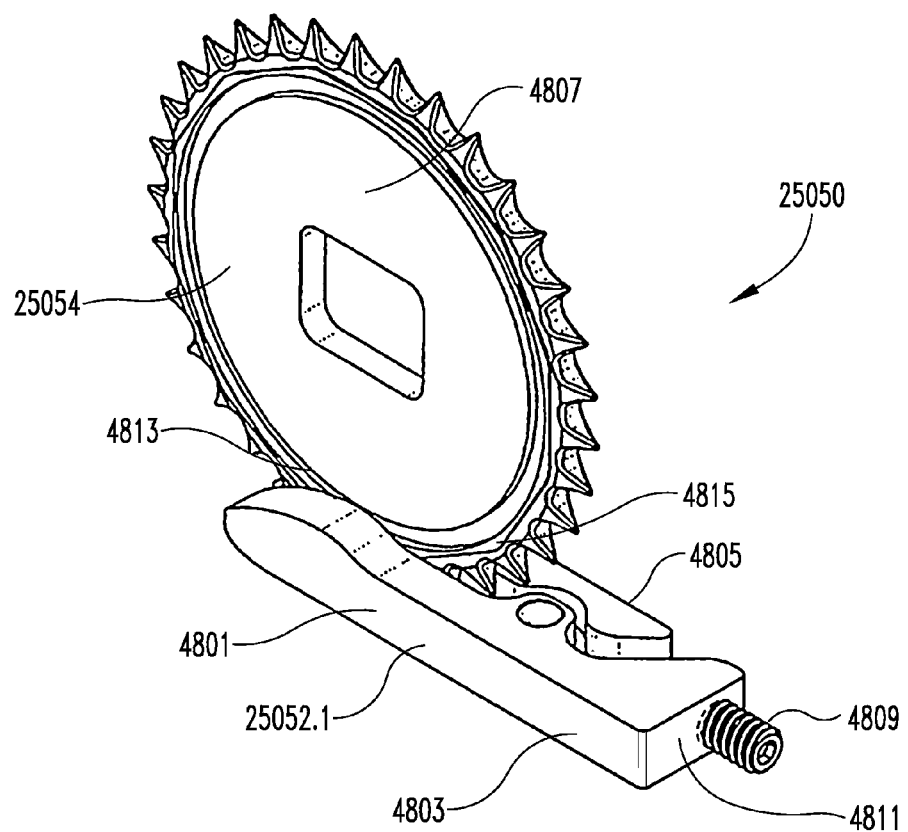

In one variation the foot 25052.1 of the cast removal system 25020 might not be attached to the keel 25052. As depicted in FIG. 68 this floating foot 4801 might be comprised of two halves 4803 and 4805 that are connected together while surrounding the distal edge of the cutter blade 4807. The two halves are joined together over the blade and a set screw 4809 is inserted into the distal end of the foot 4811 and by virtue of rotating the set screw at the distal end of the foot the proximal side of the foot is tightened against the distal sides of the cutter blade 4807. This process allows for the user to adjust the pressure of the shearing face of the foot 4813 against the shearing side 4815 of the cutter blade to facilitate the shearing of soft cast material.

Figure 69:
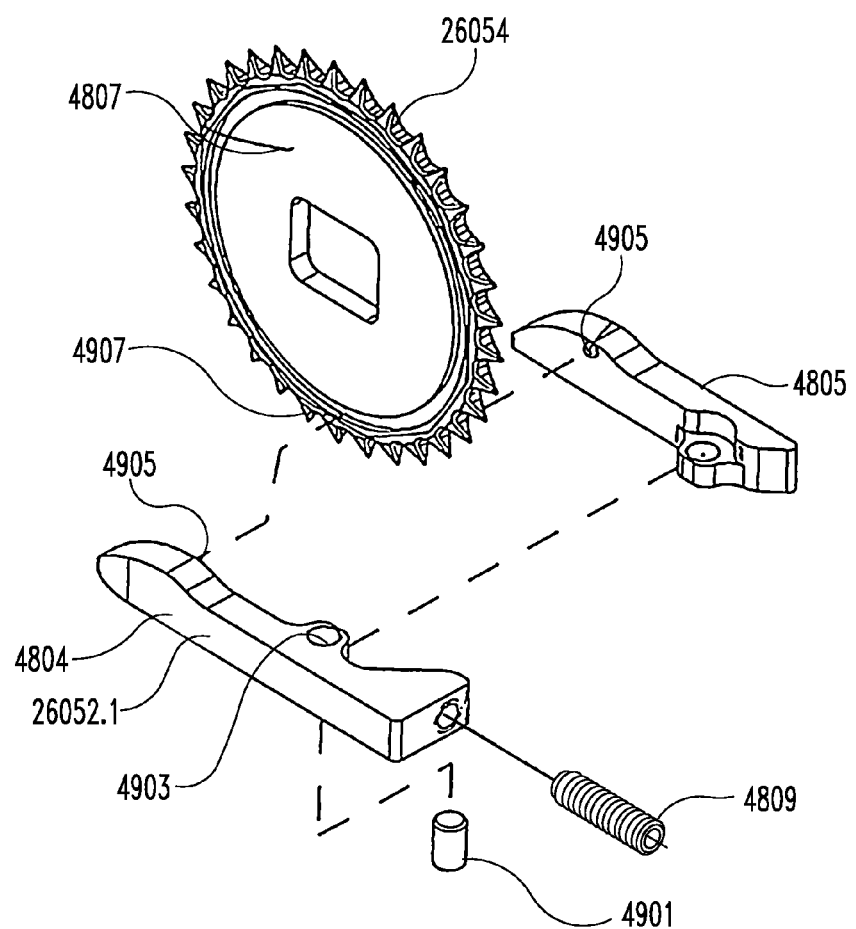

FIG. 69 depicts another embodiment of the floating foot 26052.1. The two foot halves would be connected by a pin 4901 that is inserted into a receiving slot 4903 once the two halves are joined. A set screw 4809 would then be inserted and tightened. The foot would then connect and be secured to the cast cutter blade by small pins 4905 located at the proximal end of the foot halves 4804 and 4805. When the foot halves are connected together they would lock into a grooved pathway 4907 on the cast cutter blade 4807. Once the foot halves are connected and the foot is attached to the cutter blade the foot would remain in a constant location below the cast or material that the user wishes to separate. This embodiment provides the advantage of allowing the splitting and/or shearing of the cast material without a keel reducing drag and requiring less force to operate the cast removal system. It would also allow the cast removal system to have flexibility in turning to achieve more controlled and tighter pathway for cast removal system.

Figure 70A:
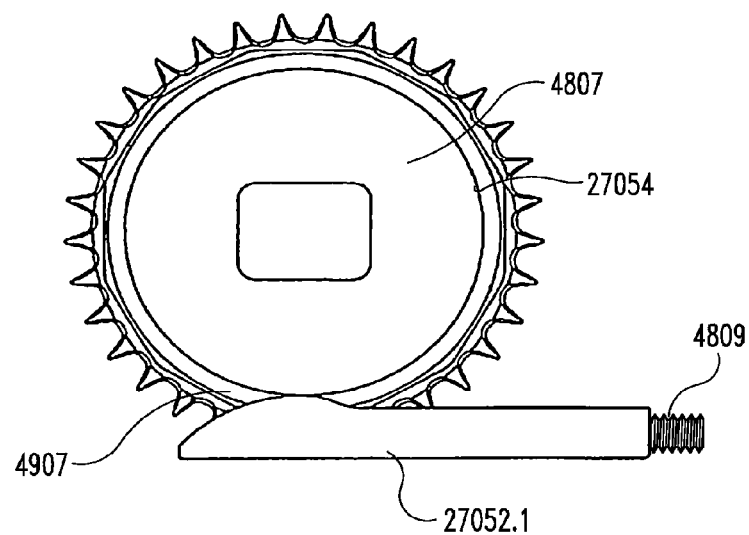
Figure 70B:
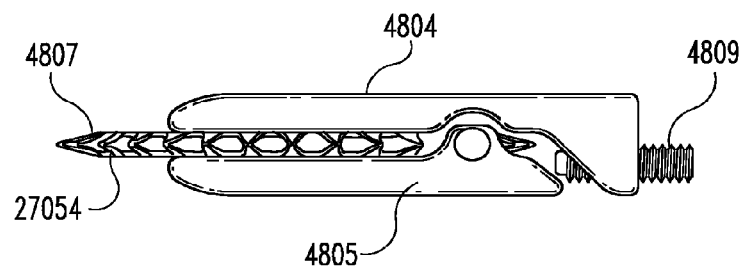

In one variation the floating foot 27052.1 could be removable any point during the cutting of the cast material. In this variation as shown in FIG. 70 the set screw 4809 might have a line 5001 attached that would allow the user to remove the screw 4809 thus separating the foot halves 4804 and 4805 by the release of pressure on the proximally located cast removal connecting pins 4905 and thus releasing them from the grooved pathway 4907 of the cutting wheel 4807. The cast cutter device could then be lifted straight up and away from the cast without any reversal action by the user.

Figure 71A:
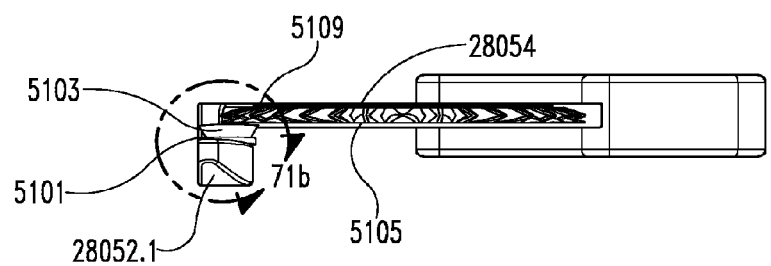
Figure 71B:
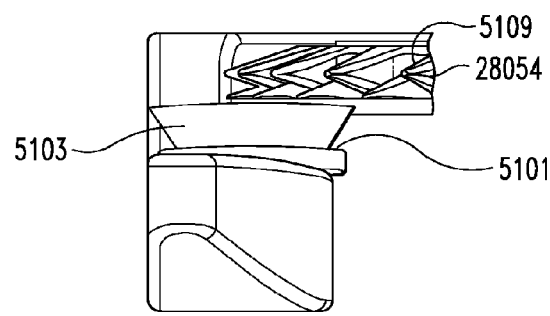

FIG. 71 shows how in one variation of the cast cutter device 28020 the shearing face of the foot 28052.1 might be a passive wheel 5103 located parallel to the cutting wheel 5105 but offset slightly to create a shearing point where the two wheels meet 5109. The use of a passive wheel in the foot to provide an alternative shearing face might reduce the need for the shearing face to force its way through the material as it is being sheared by the shearing face of a cutting blade since the rotation of the passive wheel would reduce binding and facilitate the shearing action. In the preferred embodiment the passive wheel would be 3° offset from the cutting blade. In another variation it might be 4° or more. In one variation it might be 2° or less. It could be any degree of offset that would allow for the optimal shearing of the material to be separated. In some variations it might be smaller or larger depending on the material that might need to be sheared or the outcome to be achieved. In the preferred embodiment the passive wheel might be utilized with a keel and foot apparatus. It might be with a floating foot design. The cutting blade 29054 might have a V shaped edge as shown in FIG. 72. In one variation the blade 29054' might be a half V as shown in the bottom of FIG. 72.

In one variation the cast removal system might have an additional hole cutter located at the distal end of the cast removal system as depicted in FIG. 73. This hole cutter 5301 would be a rotating cutter that would allow for the user to cute a hole into a cast or any material for access to the skin or tissue below the cast without removing the cast.

FIGS. 74 and 75 show a gear train assembly 32040 according to another embodiment of the present invention. An electric motor 32032 drives a spur gear that meshes with a beveled gear, the beveled gear being coupled to a first worm 32041.1. The worm drives the corresponding worm gear, which further rotates a plurality of mating pinion gears to ultimately drive a driving interface 32046.3.

Another aspect of the present invention pertains to an apparatus for cutting a layer of material. Further embodiments include an electric motor having an output speed and an output torque. Still further embodiments include a gear train having a driven member for receiving the output speed and output torque of a motor, a gear train including a first worm gear pair and a second worm gear pair, the first pair providing a speed reduction and torque increase to the second pair, the gear train having a driving member operating at a driving speed lower than the output speed and a driving torque higher than the output torque. Yet other embodiments include a wheel including a plurality of shearing sectors arranged in a first pattern about a first rotational axis, each sector having a sharp edge, the wheel being rotationally driven by the electric motor, wheel being driven by the driving member. Still further embodiments include a foot having a shearing surface adapted and configured for sliding contact with the face of the wheel, and a handle adapted and configured for being held by a human operator, the handle supporting a wheel, a foot, a gear train, and a motor.

Still further aspects of the present invention pertain to an apparatus for cutting a layer of material. Other embodiments include a first wheel including a plurality of shearing sectors arranged in a first pattern about a rotational axis, each sector having a sharp edge, a wheel being adapted and configured for complete rotation about the axis. Still further embodiments include a second wheel including a plurality of teeth arranged in a second pattern about the rotational axis, each tooth being adapted and configured for pressing the surface of the material, a second wheel being adapted and configured for complete rotation about the axis. Yet other embodiments include a structural member for establishing the location of the axis relative to the material, the member having an arm and a foot extending from an end of an arm, the arm extending along a peripheral side of the first wheel, the foot extending under the first wheel, wherein the first wheel and second wheel are coupled together for simultaneous rotation, and rotation of the second wheel moves the material between the foot and the first wheel and rotation of the first wheel cuts the material between the foot and the first wheel.

Another aspect of the present invention pertains to a method for cutting material. Some embodiments include providing an electric motor, a reduction gear train, a foot having shearing surface, and a shearing wheel having a sharp edge. Still other embodiments include a driving the gear train by the electric motor at a first high speed and a first low torque. Yet other embodiments include driving the shearing wheel by the gear train at a second lower speed and a second higher torque; cutting the material by shearing between the edge of the wheel and the shearing surface; and automatically advancing the material past the shearing edge at about the same linear velocity as the edge.

A further aspect of the present invention pertains to a portable apparatus for cutting material. One embodiment includes an electric motor. Further embodiments include a wheel having a sharp edge, the wheel being rotationally driven about a rotational axis by an electric motor. Still further embodiments include a foot located across from a section of the edge of the wheel; and a handle shaped for being held by the hand of a human operator, the handle includes a central axis, a handle supporting the wheel, foot, and motor. Still other embodiments include that the material is cut along a path by the sharp edge, the path being between the foot and the section of the wheel, and the path is generally perpendicular to the central axis.

While the inventions have been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An apparatus for cutting a layer of material, comprising:
an electric motor;
a wheel including a plurality of shearing sectors arranged in a first pattern about a first rotational axis, each said sector having a sharp edge, said wheel having a face, and said wheel being rotationally driven by said electric motor;
a foot having a shearing surface extending from said foot in overlapping relationship with said wheel;
a biasing member biasing the face of said wheel and the shearing surface into sliding contact with one another;
a handle adapted and configured for being held by a human operator, said handle supporting said wheel, said foot, and said motor; and
an electronic controller operably connected to said motor, said controller operating said motor so that the linear velocity of the sharp edge is substantially constant when cutting the material.

2. The apparatus of claim 1 wherein said wheel is a first wheel, which further comprises a second wheel having a plurality of teeth adapted and configured for pressing contact with the surface of the material, said second wheel being rotationally driven by said electric motor, wherein rotation of said second wheel advances the material past the shearing surface.

3. The apparatus of claim 2 wherein the shearing sectors are axially located to face the shearing surface and the teeth are axially located on the other side of the shearing surface.

4. The apparatus of claim 1 which further comprises means for automatically advancing the material past the shearing surface.

5. The apparatus of claim 4 wherein said advancing means is a second wheel having a plurality of teeth.

6. The apparatus of claim 5 wherein the teeth are adapted and configured for penetrating the surface of the material.

7. The apparatus of claim 4 wherein said advancing means is a plurality of teeth extending from said wheel.

8. The apparatus of claim 4 wherein said advancing means comes into frictional contact with the surface of the material.

9. The apparatus of claim 1 wherein said motor has an output speed and an output torque, and which further comprises a gear train having a driven member for receiving the output speed and output torque of said motor, said gear train having a driving member operating at a driving speed lower than the output speed and a driving torque higher than the output torque, said wheel being driven by the driving member, said gear train being supported by said handle.

10. The apparatus of claim 9 wherein said motor and said gear train coact to rotate said wheel in excess of a complete revolution.

11. The apparatus of claim 9 wherein said gear train includes at least one worm gear pair.

12. The apparatus of claim 11 wherein said worm gear pair is a first worm gear pair and which further comprises a second worm gear pair, said first pair driving said second pair.

13. The apparatus of claim 1 wherein said wheel has a flat face that faces toward the shearing surface.

14. The apparatus of claim 1 wherein said wheel is biased toward contact between the face of said wheel and the shearing surface.

15. The apparatus of claim 14 which further comprises a spring for biasing the wheel of said face toward the shearing surface.

16. The apparatus of claim 1 wherein the linear velocity of the sharp edge is less than about two inches per second.

17. The apparatus of claim 1 wherein the linear velocity is a first substantially constant linear velocity, and which further comprises a switch for providing an operator input signal to said controller, said controller interpreting the operator input signal to operate said wheel at the first substantially constant linear velocity.

18. The apparatus of claim 1 which further comprises a battery, said handle having two opposing ends, said battery being supported from one end of said handle and said motor being suspended from the other end of said handle.

19. The apparatus of claim 1 which further comprises a battery, said handle having two opposing ends, said battery being supported from one end of said handle and said wheel being suspended from the other end of said handle.

20. The apparatus of claim 1 wherein said controller interprets the operator input signal to operate said wheel at either the first substantially constant linear velocity or a second substantially constant linear velocity different than the first linear velocity, each of the first linear velocity and the second linear velocity being less than about two inches per second.

21. The apparatus of claim 1 wherein said motor rotates said wheel in excess of a complete revolution.

22. The apparatus of claim 1, wherein the shearing surface and the face of said wheel are substantially flat.

23. The apparatus of claim 1, wherein the shearing surface and the face of said wheel are substantially flat and define planes that are substantially parallel to one another.

24. The apparatus of claim 1, wherein the face of the wheel defines a plane that is approximately perpendicular to the axis around which the wheel rotates.

\* \* \* \* \*